US010894785B2

(12) United States Patent
Vogel et al.

(10) Patent No.: US 10,894,785 B2
(45) Date of Patent: Jan. 19, 2021

(54) PIPERIDINE DERIVATIVES FOR USE IN THE TREATMENT OF PANCREATIC CANCER

(71) Applicants: CENTRE HOSPITALIER UNIVERSITAIRE VAUDOIS CHUV, Lausanne (CH); CONSEJO SUPERIOR DE INVESTIGACIONES CIENTIFICAS (CSIC), Madrid (ES)

(72) Inventors: Pierre Vogel, La Conversion (CH); Michel Duchosal, La Conversion (CH); Nahimana Aimable, Lausanne (CH); Inmaculada Robina, Seville (ES); Faustino Mollinedo, Galapagar (ES); Alessio Nencioni, Genoa (IT)

(73) Assignees: CENTRE HOSPITALIER UNIVERSITAIRE VAUDOIS CHUV; CONSEJO SUPERIOR DE INVESTIGACIONES CIENTIFICAS (CSIC)

( * ) Notice: Subject to any disclaimer, the term of this patent is extended or adjusted under 35 U.S.C. 154(b) by 0 days.

(21) Appl. No.: 16/323,473

(22) PCT Filed: Aug. 4, 2017

(86) PCT No.: PCT/EP2017/069870
§ 371 (c)(1),
(2) Date: Feb. 5, 2019

(87) PCT Pub. No.: WO2018/024907
PCT Pub. Date: Feb. 8, 2018

(65) Prior Publication Data
US 2019/0185452 A1    Jun. 20, 2019

(30) Foreign Application Priority Data
Aug. 5, 2016 (EP) .................................... 16183131

(51) Int. Cl.
| C07D 401/12 | (2006.01) |
| C07D 401/14 | (2006.01) |
| C07D 409/14 | (2006.01) |
| C07D 407/14 | (2006.01) |
| A61P 35/00 | (2006.01) |
| C07D 405/14 | (2006.01) |

(52) U.S. Cl.
CPC ............ C07D 401/12 (2013.01); A61P 35/00 (2018.01); C07D 401/14 (2013.01); C07D 405/14 (2013.01); C07D 407/14 (2013.01); C07D 409/14 (2013.01)

(58) Field of Classification Search
CPC .................................................. C07D 401/12
See application file for complete search history.

(56) References Cited

U.S. PATENT DOCUMENTS 9,187,472 B2    11/2015    Clark

FOREIGN PATENT DOCUMENTS

| DE | 19624659 A1 | 1/1998 |
| WO | 2011121055 A1 | 10/2011 |
| WO | WO2011121055 | * 10/2011 |

OTHER PUBLICATIONS

PCT/EP2017/069870 International Search Report and Written Opinion, dated Oct. 16, 2017, 11 pages.
You, H et al. "Design, synthesis and X-ray crystallographic study of NAmPRTase inhibitors as anti-cancer agents," European Journal of Medicinal Chemistry 46(4), 1153-1164 (2011).

* cited by examiner

*Primary Examiner* — Paul V Ward
(74) *Attorney, Agent, or Firm* — Wolter Van Dyke Davis, PLLC; Robert L. Wolter

(57) ABSTRACT

The present invention relates to novel piperidine derivatives having better cell growth inhibitory activities toward cancer cell cultures and, more particularly, PANC-1 cancer cell cultures than FK866. Accordingly, the present invention relates to compounds of formula I, wherein $Ar_1$ is aryl or heteroaryl, which are optionally substituted by one, two or three substituents selected from lower alkyl; lower alkoxy; formyl; hydroxyl; lower alkyl substituted by lower alkoxy or hydroxyl; A is $C_nH_{2n}$, $C_nH_{2n-2}$ or $C_nH_{2n-4}$, wherein n=4,5, 6,7; B is =N—CN, oxo (=O), thio (=S); D is NH, —CH=CH—; $Ar_2$ is aryl or heteroaryl which are optionally substituted by one, two or three halogen substituents; wherein, if B is oxo (=O), $Ar_1$ and $Ar_2$ are not simultaneously phenyl and pyridine-3-yl; B and D are not simultaneously =N—CN and —CH=CH—, or a pharmaceutically acceptable salt, a racemic mixture or its corresponding enantiomers and/or optical isomers. The compounds of formula I and their pharmaceutically usable addition salts possess valuable pharmacological properties. Specifically, it has been found that the compounds of the present invention, alone or in combination with other therapeutic active compounds, have an activity as chemotherapeutic agents against cancer and, more particularly, pancreatic cancers.

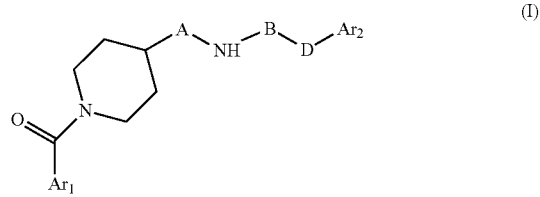

18 Claims, No Drawings

PIPERIDINE DERIVATIVES FOR USE IN THE TREATMENT OF PANCREATIC CANCER

The present invention relates to piperidine derivatives and their use as chemotherapeutic agents against cancers and, more particularly, pancreatic cancers.

Alterations in cell metabolism have emerged as one of the hallmarks of cancer that could possibly lead to new targeted therapeutic approaches (Hanahan D, Weinberg R A. Hallmarks of cancer: the next generation. Cell. 2011; 144(5): 646-74). Among the features distinguishing cancer cells from their normal counterparts there is an upregulated nicotinamide adenine dinucleotide (NAD) biosynthesis, which is needed to face increased proliferation, metabolic processes, as well as NAD consumption by cell signaling proteins and DNA repair enzymes. Thus, depleting NAD synthesis has been proposed as a novel strategy in oncology and the NAD biosynthetic machinery is emerging as a highly promising therapeutic target (Montecucco F, Cea M, Bauer I, Soncini D, Caffa I, Lasiglie D, et al. Nicotinamide phosphoribosyltransferase (NAMPT) inhibitors as therapeutics: rationales, controversies, clinical experience. Current drug targets. 2013; 14(6):637-43). NAD could be synthesized from various precursors that include tryptophan, nicotinic acid (NA), nicotinamide riboside (NR), and nicotinamide (NAM), the latter being widely used in mammalian cells. The enzyme nicotinamide phosphoribosyltransferase (NAMPT) enzyme catalyzes the first reaction of the synthesis of NAD from nicotinamide. NAMPT is a promising therapeutic target for cancers. Mounting evidence indicates that NAMPT is frequently up-regulated in many cancers (Shackelford R E, Mayhall K, Maxwell N M, Kandil E, Coppola D. Nicotinamide phosphoribosyltransferase in malignancy: a review. Genes & cancer. 2013; 4(11-12):447-56.).

Previous clinical studies have demonstrated that most cancer cells are sensitive to (E)-N-[4-(1-benzoylpiperidin-4-yl)butyl]-3-(pyridin-3-yl)acrylamide, also kwon as FK866, a NAMPT inhibitor-mediated cell death, without significant toxicity to animals (Nahimana A, Attinger A, Aubry D, Greaney P, Ireson C, Thougaard A V, Tjornelund J, Dawson K M, Dupuis M, Duchosal M A. The NAD biosynthesis inhibitor FK866 has potent antitumor activity against hematologic malignancies. Blood. 2009 Apr. 2; 113(14):3276-86.). However, the specific cell growth inhibitory activity toward PANC-1 cancer cell cultures of FK866 is relatively low. Furthermore, compound FK866 failed in clinical phase II most probably due to its too short lifetime in vivo and its low water solubility (Goldinger S M, Gobbi Bischof S, Fink-Puches R, Klemke C D, Dréno B, Bagot M, Dummer R. Efficacy and Safety of APO866 in Patients With Refractory or Relapsed Cutaneous T-Cell Lymphoma: A Phase 2 Clinical Trial. JAMA Dermatol. 2016 Mar. 23. doi: 10.1001/jamadermatol.2016.0401.).

The present invention relates to novel piperidine derivatives having better cell growth inhibitory activities toward cancer cell cultures, particularly toward PANC-1 cancer cell cultures, than FK866. Accordingly, the present invention relates to compounds of formula I

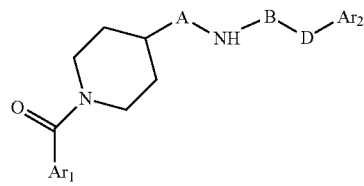

wherein
$Ar_1$ is aryl or heteroaryl, which are optionally substituted by one, two or three substituents selected from lower alkyl; lower alkoxy; formyl; hydroxyl; lower alkyl substituted by lower alkoxy or hydroxyl;
A is $C_nH_{2n}$, $C_nH_{2n-2}$, $C_nH_{2n-4}$, wherein n=4,5,6,7;
B is C=N—CN, oxo (C=O), thio (C=S);
D is NH, C—CH=CH—;
$Ar_2$ is aryl or heteroaryl which are optionally substituted by one, two or three halogen substituents
wherein,
if B is oxo (C=O), $Ar_1$ and $Ar_2$ are not simultaneously phenyl and pyridine-3-yl;
B and D are not simultaneously C=N—CN and C—CH=CH—.
or a pharmaceutically acceptable salt, a racemic mixture or its corresponding enantiomers and/or optical isomers.

The following definitions of the general terms used in the present description apply irrespective of whether the terms in question appear alone or in combination.

As used herein, the term "aryl" denotes a carbocyclic ring system, containing from 6 to 10 carbon atoms forming one or more rings, and wherein at least one ring is aromatic in nature, for example phenyl or naphthyl.

The term "heteroaryl" denotes a carbocyclic ring system, containing from 5 to 10 ring atoms forming one or more rings, wherein at least one carbon atom is replaced by a heteroatom, selected from the group consisting of O, N or S, and wherein at least one ring is aromatic in nature, for example oxazolyl, pyridyl, thiophenyl, quinolinyl, pyrrolyl, furyl, benzoimidazolyl, imidazolyl and the like.

The term "lower alkyl" denotes a saturated, aliphatic hydrocarbon group including a straight or branched carbon chain with 1-4 carbon atoms. Examples for "alkyl" are methyl, ethyl, n-propyl and isopropyl.

The term "lower alkoxy" denotes a group —O—R' wherein R' is lower alkyl as defined above.

The term "lower alkyl substituted by hydroxy" denotes a lower alkyl group, wherein at least one hydrogen atom, preferably one, two or three hydrogen atoms, is replaced by a hydroxy group.

The term "lower alkyl substituted by lower alkoxy" denotes a lower alkyl group, wherein at least one hydrogen atom, preferably one, two or three hydrogen atoms, is replaced by a lower alkoxy group as defined above.

The term "halogen" denotes chlorine, bromine, fluorine or iodine. Preferred halogen is fluorine.

The term "pharmaceutically acceptable salt" or "pharmaceutically acceptable acid addition salt" embraces salts with inorganic and organic acids, such as hydrochloric acid, nitric acid, sulfuric acid, phosphoric acid, citric acid, formic acid, fumaric acid, maleic acid, acetic acid, nrpopionic acid, hexanoic acid, octanoic acid, lauric acid, benzoic acid, cinnamic acid, succinic acid, tartaric acid, malic acid, lactic acid, camphanic acid, methanesulfonic acid, p-toluenesulfonic acid, camphorsulfonic acid and the like.

Preferably, $Ar_1$ is phenyl; thiophen; furan; oxazole; pyrrol; which are optionally substituted by one, two or three substituents selected from lower alkyl; lower alkoxy; formyl; hydroxyl; lower alkyl substituted by one, two or three lower alkoxy or hydroxyl. Preferred compounds are those wherein $Ar_1$ is phenyl; thiophen-2-yl; 2,4-dimethoxyphenyl; 2,6-dimethoxyphenyl; 2,4,6-trimethoxyphenyl; 3-methoxyfuran-2-yl; furan-2-yl; 1,2-oxazole-5-yl; 4-formyl-2,6-dimethoxyphenyl; 4-(dimethoxymethyl)-2,6-dimethoxyphenyl; 5-hydroxy-2-methylfuro-2-yl; 5-formyl-2-methylfuro-3-yl; 4-hydroxymethyl-2,6-dimethoxyphenyl; 4-formyl-2,6-dimethoxyphenyl; 4-formyl-2-methyl-1-propyl-pyrrol-3-yl. Still more preferred are those compounds wherein $Ar_1$ is 2,4-dimethoxyphenyl; 2,6-dimethoxyphenyl; 2,4,6-trimethoxyphenyl.

According to another preferred embodiment of the present invention, $Ar_2$ is pyridine; pyridazin; diazin; which are optionally substituted by one, two or three halogen substituents. The halogen substituent is (are) preferably fluorine. Preferred embodiments are those wherein $Ar_2$ is pyridin-3-yl; 2-fluoropiyridin-3-yl; 4-fluoropyridin-3-yl; 5-fluoropyridin-3-yl; 2,4-difluoropyridin-3-yl; 2,6-difluoropyridin-3-yl; pyridin-4-yl; 2-fluoropyridin-4-yl; 3-fluoropyridin-4-yl; 6-fluoropyridin-4-yl; 2,3-difluoropyridin-4-yl; 2,5-difluoropyridin-4-yl; 3,5-difluropyridin-4-yl; 2,4,5-trifluoropyridin-4-yl; pyridazin-5-yl; 1,2-diazin-4-yl; Still more referred compounds are those wherein $Ar_2$ is 2-fluoropyridin-4-yl; 3-fluoropyridin-4-yl; 6-fluoropyridin-4-yl; 2,3-difluoropyridin-4-yl; 2,5-difluoropyridin-4-yl; 3,5-difluropyridin-4-yl; 2,4,5-trifluoropyridin-4-yl.

According to another preferred embodiment of the present invention, B is C=N—CN

According to another preferred embodiment of the present invention, A is $C_nH_{2n}$, $C_nH_{2n-2}$ or $C_nH_{2n}$ and n is 4 or 5. Preferably A is $C_4H_8$ and, still more preferably, $C_5H_{10}$.

Still according to another preferred embodiment of the present invention, D is NH Still according to another preferred embodiment of the present invention, $Ar_2$ is 2-fluoropyridin-4-yl; 3-fluoropyridin-4-yl; 6-fluoropyridin-4-yl; 2,3-difluoropyridin-4-yl; 2,5-difluoropyridin-4-yl; 3,5-difluropyridin-4-yl; 2,4,5-trifluoropyridin-4-yl.

Still more preferably, the present invention relates to compounds of Formula I wherein
A is $C_4H_8$, $C_5H_{10}$
B is C=N—CN;
D is NH
$Ar_1$ is 2,4-dimethoxyphenyl; 2,6-dimethoxyphenyl; 2,4,6-trimethoxyphenyl;
$Ar_2$ is 2-fluoropyridin-4-yl; 3-fluoropyridin-4-yl; 6-fluoropyridin-4-yl; 2,3-difluoropyridin-4-yl; 2,5-difluoropyridin-4-yl; 3,5-difluropyridin-4-yl; 2,4,5-trifluoropyridin-4-yl.

Preferred compounds according to the present invention are
(E)-3-(2-fluoropyridin-3-yl)-N-4-(1-(thiophene-2-carbonyl)piperidin-4-yl)butyl)acrylamide
(E)-N-(4-1-(2,6-dimethoxybenzoyl)piperidin-4-yl)butyl)-3-(2-fluoropyridin-3-yl)acrylamide
(E)-N-(4-(1-benzoylpiperidin-4-yl)butyl)-3-(2-fluoropyridin-3-yl)acrylamide
(E)-3-(2,6-difluoropyridin-3-yl)-N-(4-1-(2,6-dimethoxybenzoyl)piperidin-4-yl)butyl) acrylamide
(E)-3-(2-fluoropyridin-3-yl)-N-(4-1-(5-(hydroxymethyl-2-methylfuro-3-yl)piperidin-4-yl)butyl) acrylamide
(E)-3-(2-fluoropyridin-3-yl)-N-(4-(1-(5-formyl-2-methylfuro-3-yl)piperidin-4-yl)butyl) acrylamide
(E)-3-(2-fluoropyridin-3-yl)-N-(4-(1-(4-(hydroxymethyl)-2,6-dimethoxybenzoyl))piperidin-4-yl)butyl)acrylamide
(E)-3-(2-fluoropyridin-3-yl)-N-(4-(1-(4-formyl-2,6-dimethoxybenzoyl))piperidin-4-yl)butyl) acrylamide
(E)-3-(2-fluoropyridin-3-yl)-N-(4-(1-(4-formyl-2-methyl-1-propyl-1H-pyrrole-3-carbonyl)piperidin-4-yl)butyl)acrylamide
(E)-N-(4-(1-benzoylpiperidin-4-yl)butyl)-3-(2,6-difluoropyridin-3-yl)acrylamide
(E)-3-(2,6-difluoropyridin-3-yl)-N-4-(1-(thiophene-2-carbonyl)piperidin-4-yl)butyl) acrylamide
(E)-3-(2,6-difluoropyridin-3-yl)-N-4-(1-(furan-2-carbonyl)piperidin-4-yl)butyl)acrylamide
(E)-N-(4-(1-(2,4-Dimethoxybenzoyl)piperidin-4-yl)butyl)-3-(pyridin-3-yl)acrylamide
(E)-N-(4-(1-(2,6-Dimethoxybenzoyl)piperidin-4-yl)butyl)-3-(pyridin-3-yl)acrylamide
(E)-3-(Pyridin-3-yl)-N-(4-(1-(2,4,6-trimethoxybenzoyl)piperidin-4-yl)butyl)acrylamide
(E)-N-(4-(1-(3-Methoxyfuran-2-carbonyl)piperidin-4-yl)butyl)-3-(pyridin-3-yl)acrylamide
(E)-N-(4-(1-(Isoxazole-5-carbonyl)piperidin-4-yl)butyl)-3-(pyridin-3-yl)acrylamide
(E)-N-(4-(1-(4-Formyl-2,6-dimethoxybenzoyl)piperidin-4-yl)butyl)-3-(pyridin-3-yl)acrylamide
(E)-N-((E)-4-(1-Benzoylpiperidin-4-yl)but-2-en-1-yl)-3-(pyridin-3-yl)acrylamide
(E)-N-((E)-4-(1-(2,6-Dimethoxybenzoyl)piperidin-4-yl)but-2-en-1-yl)-3-(pyridin-3-yl)acrylamide
(E)-3-(Pyridin-3-yl)-N-((E)-4-(1-(2,4,6-trimethoxybenzoyl)piperidin-4-yl)but-2-en-1-yl)acrylamide
(E)-N-((E)-4-(1-(Furan-2-carbonyl)piperidin-4-yl)but-2-en-1-yl)-3-(pyridin-3-yl)acrylamide
(E)-3-(Pyridin-3-yl)-N-((E)-4-(1-(thiophene-2-carbonyl)piperidin-4-yl)but-2-en-1-yl)acrylamide
(E)-N-(4-(1-Benzoylpiperidin-4-yl)butyl)-3-(pyridazin-4-yl)acrylamide
(E)-N-(4-(1-(Furan-2-carbonyl)piperidin-4-yl)butyl)-3-(pyridazin-4-yl)acrylamide
(E)-3-(Pyridazin-4-yl)-N-(4-(1-(thiophene-2-carbonyl)piperidin-4-yl)butyl)acrylamide
(E)-N-(4-(1-(2,6-Dimethoxybenzoyl)piperidin-4-yl)butyl)-3-(pyridazin-4-yl)acrylamide
1-(4-(1-Benzoylpiperidin-4-yl)butyl)-3-(pyridin-3-yl)urea
1-(4-(1-(Furan-2-carbonyl)piperidin-4-yl)butyl)-3-(pyridin-3-yl)urea
1-(Pyridin-3-yl)-3-(4-(1-(thiophene-2-carbonyl)piperidin-4-yl)butyl)urea
1-(4-(1-(2,6-Dimethoxybenzoyl)piperidin-4-yl)butyl)-3-(pyridin-3-yl)urea
1-(4-(1-Benzoylpiperidin-4-yl)butyl)-3-(pyridin-4-yl)urea
1-(4-(1-(Furan-2-carbonyl)piperidin-4-yl)butyl)-3-(pyridin-4-yl)urea
1-(Pyridin-4-yl)-3-(4-(1-(thiophene-2-carbonyl)piperidin-4-yl)butyl)urea
1-(4-(1-(2,6-Dimethoxybenzoyl)piperidin-4-yl)butyl)-3-(pyridin-4-yl)urea
(E)-1-(4-(1-Benzoylpiperidin-4-yl)butyl)-2-cyano-3-(pyridin-4-yl)guanidine
(E)-2-Cyano-1-(4-(1-(2,6-dimethoxybenzoyl)piperidin-4-yl)butyl)-3-(pyridin-4-yl)guanidine
(E)-2-Cyano-1-(4-(1-(furan-2-carbonyl)piperidin-4-yl)butyl)-3-(pyridin-4-yl)guanidine
(E)-2-Cyano-1-(pyridin-4-yl)-3-(4-(1-(thiophene-2-carbonyl)piperidin-4-yl)butyl)guanidine (E)-2-cyano-1-(4-(1-(4-(dimethoxymethyl)-2,6-dimethoxybenzoyl)piperidin-4-yl)butyl)-3-(pyridazin-4-yl)guanidine
(E)-2-Cyano-1-(4-(1-(furan-2-carbonyl)piperidin-4-yl)butyl)-3-(pyridazin-4-yl)guanidine
(E)-1-(4-(1-Benzoylpiperidin-4-yl)butyl)-2-cyano-3-(6-fluoropyridin-3-yl)guanidine
(E)-2-Cyano-1-(4-(1-(2,6-dimethoxybenzoyl)piperidin-4-yl)butyl)-3-(6-fluoropyridin-3-yl)guanidine
(E)-2-cyano-1-(4-(1-(4-(dimethoxymethyl)-2,6-dimethoxybenzoyl)piperidin-4-yl)butyl)-3-(6-fluoropyridin-3-yl)guanidine
(E)-2-Cyano-1-(6-fluoropyridin-3-yl)-3-(4-(1-(furan-2-carbonyl)piperidin-4-yl)butyl)guanidine
(E)-2-Cyano-1-(6-fluoropyridin-3-yl)-3-(4-(1-(thiophene-2-carbonyl)piperidin-4-yl)butyl)guanidine
(E)-1-(5-(1-Benzoylpiperidin-4-yl)pentyl)-2-cyano-3-(pyridin-3-yl)guanidine
(E)-2-Cyano-1-(5-(1-(furan-2-carbonyl)piperidin-4-yl)pentyl)-3-(pyridin-3-yl)guanidine
(E)-2-Cyano-1-(pyridin-3-yl)-3-(5-(1-(thiophene-2-carbonyl)piperidin-4-yl)pentyl)guanidine
(E)-1-(5-(1-Benzoylpiperidin-4-yl)pentyl)-2-cyano-3-(pyridin-4-yl)guanidine
(E)-2-Cyano-1-(5-(1-(furan-2-carbonyl)piperidin-4-yl)pentyl)-3-(pyridin-4-yl)guanidine
(E)-2-Cyano-1-(pyridin-4-yl)-3-(5-(1-(thiophene-2-carbonyl)piperidin-4-yl)pentyl)guanidine
(E)-2-Cyano-1-(5-(1-(2,6-dimethoxybenzoyl)piperidin-4-yl)pentyl)-3-(pyridin-4-yl)guanidine
(E)-1-((E)-5-(1-Benzoylpiperidin-4-yl)pent-2-en-1-yl)-2-cyano-3-(pyridin-3-yl)guanidine
(E)-2-Cyano-1-((E)-5-(1-(furan-2-carbonyl)piperidin-4-yl)pent-2-en-1-yl)-3-(pyridin-3-yl)guanidine
(E)-2-Cyano-1-(pyridin-3-yl)-3-((E)-5-(1-(thiophene-2-carbonyl)piperidin-4-yl)pent-2-en-1-yl)guanidine
(E)-2-Cyano-1-((E)-5-(1-(2,6-dimethoxybenzoyl)piperidin-4-yl)pent-2-en-1-yl)-3-(pyridin-3-yl)guanidin
(E)-1-((E)-5-(1-Benzoylpiperidin-4-yl)pent-2-en-1-yl)-2-cyano-3-(pyridin-4-yl)guanidine
(E)-2-Cyano-1-((E)-5-(1-(furan-2-carbonyl)piperidin-4-yl)pent-2-en-1-yl)-3-(pyridin-4-yl)guanidine
(E)-2-Cyano-1-(pyridin-4-yl)-3-((E)-5-(1-(thiophene-2-carbonyl)piperidin-4-yl)pent-2-en-1-yl)guanidine
(E)-2-Cyano-1-((E)-5-(1-(2,6-dimethoxybenzoyl)piperidin-4-yl)pent-2-en-1-yl)-3-(pyridin-4-yl)guanidine
1-(4-(1-Benzoylpiperidin-4-yl)butyl)-3-(pyridin-3-yl)thiourea
1-(4-(1-(Furan-2-carbonyl)piperidin-4-yl)butyl)-3-(pyridin-3-yl)thiourea
1-(Pyridin-3-yl)-3-(4-(1-(thiophene-2-carbonyl)piperidin-4-yl)butyl)thiourea
1-(4-(1-(2,6-Dimethoxybenzoyl)piperidin-4-yl)butyl)-3-(pyridin-3-yl)thiourea.

A further object of the present invention is a compound of formula I for use as therapeutically active substance and, more particularly, for use in the treatment of cancer and, even more particularly, pancreatic cancer.

A further object of the present invention is a pharmaceutical composition comprising a compound of formula I and pharmaceutically acceptable excipients.

A further object of the present invention is the use of a compound of formula I for the manufacture of a medicament for treating cancer and, more particularly, pancreatic cancer.

The new compounds of formula I and their pharmaceutically acceptable salts, can be prepared by methods known in the art, for example, by processes described below, which processes comprise:

a) Reacting a compound of formula 1

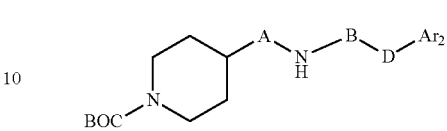

With a compound of formula 2

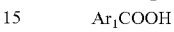

To a compound of formula I

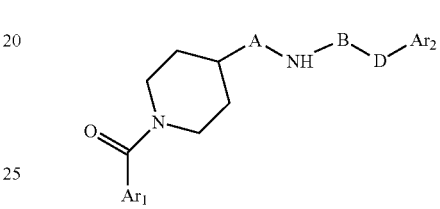

wherein
A is $C_nH_{2n}$, $C_nH_{2n-2}$, $C_nH_{2n-4}$ wherein n=4,5,6,7
B is oxo (C=O)
D is C—CH=CH—
$Ar_1$ and $Ar_2$ are as defined in claim 1 b) Reacting a compound of formula 3

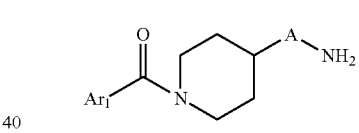

With a compound of formula 4

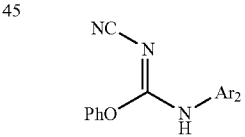

To a compound of formula I

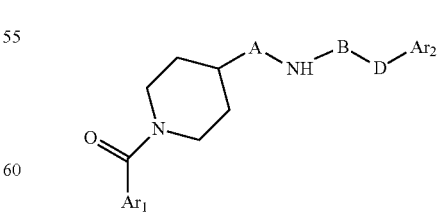

wherein
A is $C_nH_{2n}$, $C_nH_{2n-2}$, $C_nH_{2n-4}$ wherein n=4,5,6,7
B is C=N—CN
D is NH
$Ar_1$ and $Ar_2$ are as defined in claim 1 c) Reacting a compound of formula 3

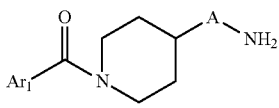

With a compound of formula 5

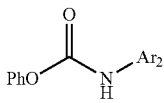

To a compound of formula I

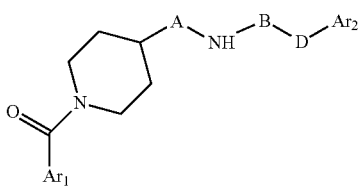

wherein
A is $C_nH_{2n}$, $C_nH_{2n-2}$, $C_nH_{2n-4}$ wherein n=4,5,6,7
B is oxo (C=O)
D is NH
$Ar_1$ and $Ar_2$ are as defined in claim 1 d) Reacting a compound of formula 3

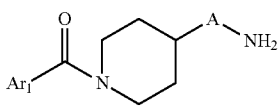

With a compound of formula 6

$Ar_2$—NCS

To a compound of formula I

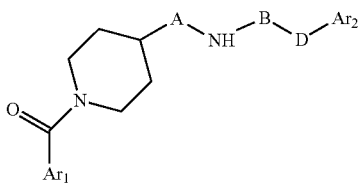

A is $C_nH_{2n}$, $C_nH_{2n-2}$, $C_nH_{2n-4}$ wherein n=4,5,6,7
B is thio (C=S)
D is NH
$Ar_1$ and $Ar_2$ are as defined in claim 1 e) Reacting a compound of formula 7

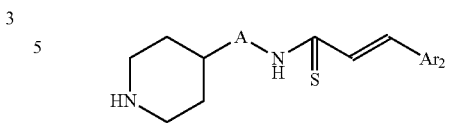

With a compound of formula 2

$Ar_1COOH$

To a compound of formula I

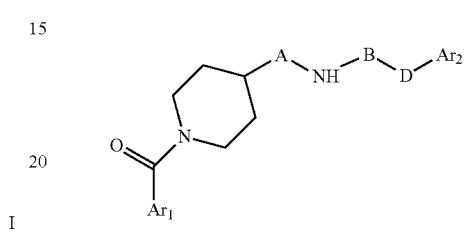

A is $C_nH_{2n}$, $C_nH_{2n-2}$, $C_nH_{2n-4}$ wherein n=4,5,6,7
B is thio (C=S), D is C—CH=CH—
$Ar_1$ and $Ar_2$ are as defined in claim 1

The preparation of compounds of formula I may be carried out in sequential or convergent synthetic routes. Syntheses of the compounds of the invention are shown under "Manufacturing Processes and Examples" below. The skills required for carrying out the reaction and purification of the resulting products are known to those skilled in the art. The substituents and indices used in the following description of the processes have the significance given herein before unless otherwise indicated.

In more detail, the compounds of formula I can be manufactured by the methods given in the examples or by analogous methods. Appropriate reaction conditions for the individual reaction steps are known to a person skilled in the art.

Isolation and purification of the compounds and intermediates described herein can be carried out, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. If needed, racemic mixtures of chiral compounds of formula I can be separated using chiral HPLC.

The compounds of formula I are basic and may be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, lactic acid, malic acid, maleic acid, fumaric acid, tartaric acid, citric acid, benzoic acid, cinnamic acid, mandelic acid, camphanic acid, methanesulfonic acid, ethanesulfonic acid, p-toluenesulfonic acid, camphorsulfonic acid, salicylic acid and the like. Typically, the free base is dissolved in an inert organic solvent such as diethyl ether, ethyl acetate, chloroform, ethanol or methanol and the like and the acid added thereto. The temperature is maintained between 0° C. and 50° C. The resulting salt precipitates spontaneously or may be brought out of solution with a less polar solvent.

The compounds of formula I and their pharmaceutically usable addition salts possess valuable pharmacological properties. Specifically, it has been found that the compounds of the present invention, alone or in combination with other therapeutic active compounds, have an activity as chemotherapeutic agents against cancers and, more particularly, pancreatic cancers. The compounds of formula I and their pharmaceutically usable addition salts have improved water solubility and pharmacologic half life if compared to the benchmark compound FK866.

The compounds of formula I were investigated in accordance with the test given hereinafter.

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragées, hard and soft gelatine capsules, solutions emulsions or suspensions. The administration can, however, also be effected rectally, e.g. in the form of suppositories, or parenterally, e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can moreover contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

The dosage can vary within wide limits and will have to be adjusted to the individual requirements in each particular case. In the case of oral administration, the dosage for adults can vary from about 0.01 mg to about 1000 mg per day of a compound of general formula I or of the corresponding amount of a pharmaceutically acceptable salt thereof. The daily dosage may be administered as single dose or in divided doses and, in addition, the upper limit can also be exceeded when this is found to be appropriate by medical practitioners.

Tablet Formulation (Wet Granulation)

| | | Mg/tablet | | | |
| --- | --- | --- | --- | --- | --- |
| Item | Ingredients | 5 mg | 25 mg | 100 mg | 500 mg |
| 1 | Compound of formula I | 5 | 25 | 100 | 500 |
| 2 | Lactose Anhydrous DTG | 125 | 105 | 30 | 150 |
| 3 | Sta-RX 1500 | 6 | 6 | 6 | 30 |
| 4 | Mycrocristalline Cellulose | 30 | 30 | 30 | 150 |
| 5 | Magnesium Stearate | 1 | 1 | 1 | 1 |
| | Total | 167 | 167 | 167 | 831 |

Manufacturing Procedure
Mix items 1, 2, 3 and 4 and granulate with purified water.
Dry the granules at 50° C.
Pass the granules through suitable milling equipment.
Add item 5 and mix for three minutes; compress on a suitable press.

Capsule Formulation

| | | Mg/capsule | | | |
| --- | --- | --- | --- | --- | --- |
| Item | Ingredients | 5 mg | 25 mg | 100 mg | 500 mg |
| 1 | Compound of formula I | 5 | 25 | 100 | 500 |
| 2 | Hydrous Lactose | 159 | 123 | 148 | — |
| 3 | Corn Starch | 25 | 35 | 40 | 70 |
| 4 | Talc | 10 | 15 | 10 | 25 |
| 5 | Magnesium Stearate | 1 | 2 | 2 | 5 |
| | Total | 200 | 200 | 300 | 600 |

Manufacturing Procedure
Mix items 1, 2 and 3 in a suitable mixer for 30 minutes.
Add items 4 and 5 and mix for 3 minutes.
Fill into a suitable capsule

MANUFACTURING PROCESS AND EXAMPLES

General

All commercially available reagents were purchased from Sigma Aldrich, Fluka or Acros and used without further purification. For reactions requiring anhydrous conditions, dry solvents were bought (Fluka, Aldrich). All reactions were carried out under nitrogen atmosphere in oven-dried glassware with magnetic stirring. Analytical TLC (thin layer chromatography) was performed with silica gel 60 $F_{254}$ aluminum plates (Merck) with visualization by UV light and charring with aqueous $KMnO_4$ solution, ethanolic ninhydrin solution or Pancaldi reagent. Column chromatography was performed with 230-400 mesh, MN Kieselgel 60M silica gel (Merck) and. Infrared spectra were recorded with a Jasco FTIR-410 spectrophotometer. $^1H$ and $^{13}C$ NMR analyses were performed with Bruker AVIII-400 spectrometer at 400 MHz and 100 MHz respectively and Bruker AMX300 spectrometer at 300 MHz and 75.4 MHz respectively at 20° C. (the piperidine of amide show split signals in $^{13}C$ NMR at 20° C.). Chemical shifts are calibrated using residual solvents signals ($CDCl_3$: δ (H)=7.26, δ (C)=77.16; $CD_3CN$: δ (H)=1.94, δ (C)=118.26, 1.32) and reported in ppm. Multiplicities: s=apparent singlet, d=apparent doublet, t=apparent triplet, q=apparent quadruplet, m=multiplet, br=broad. Apparent coupling constant are given in Hz. The assignments were confirmed by COSY and HSQC experiments. Mass spectra (CI and LSI) were recorded on Micromass AutoSpeQ and QTRAP spectrometers. The LSI was performed using thioglycerol as the matrix. HRMS spectra were recorder on Mass Spectral Facility of Institute of Chemical Sciences and Engineering (ISIC), Swiss Federal Institute of Technology, Lausanne (EPFL) and CITIUS (University of Seville), are given in m/z.

Abbreviations:
Boc=(tert-Butoxy)carbonyl;
Dess-Martin reagent=1,1,1-Triacetoxy-1,1-dihydro-1,2-benziodoxol-3(1H)-one
DEAD=diethyl azodicarboxylate
DCM=dichloromethane
DIPEA=di(isopropyl)ethylamine
DIBAL=diisopropylaluminium hydride
DMF=N,N-dimethylformamide
HOBt=N-Hydroxybenzotriazole;
EDCl=1-(3-Dimethylaminopropyl)-3-ethylcarbodiimide hydrochloride
EtOAc=ethyl acetate
LAH=LiAlH$_4$
NMM=N-methylmorpholine;
PE=petroleum ether
PyBOP=benzotriazol-1-yl-oxytripyrrolidinophosphonium hexafluorophosphate
TEA=triethylamine
TFA=trifluoroacetic acid
THF=tetrahydrofuran
TsCl=paratoluenesulfonyl chloride
FC=Flash column chromatography on silica gel, unless noted otherwise.
TLC=thin layer chromatography on silica gel.
MW=molecular weight General Procedure for the Synthesis of FEI 56, FEI 58, FEI 62, FEI 71, FEI 74, FEI 75, FEI95, FEI96, FEI97, FEI98

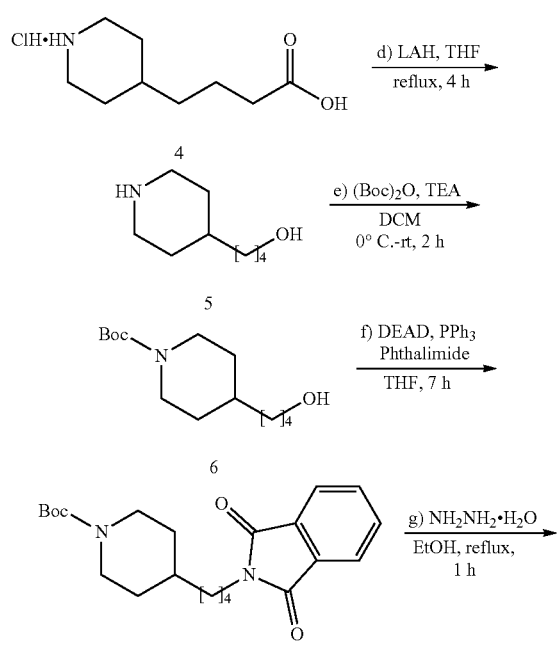

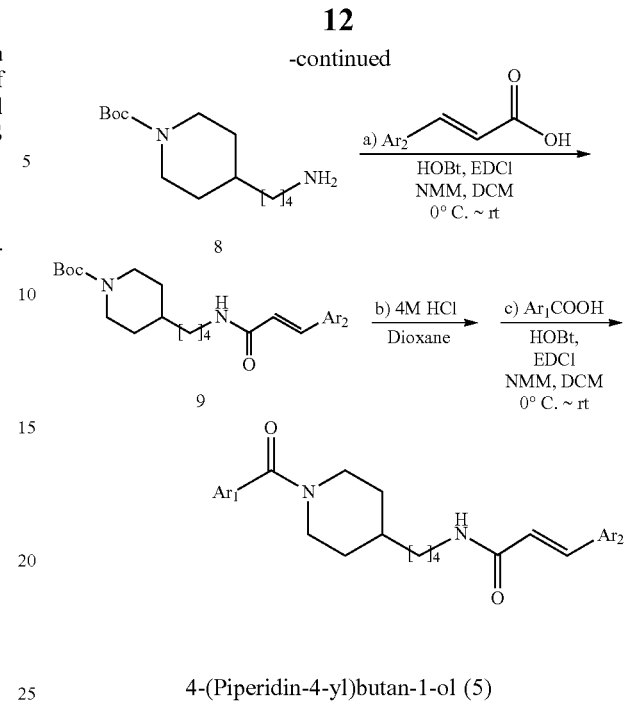

4-(Piperidin-4-yl)butan-1-ol (5)

A suspension of 4-(piperidin-4-yl)butanoic acid hydrochloride (4, 9.0 g, 44 mmol, MW=200.664) in dry THF (150 mL) was cooled in an ice bath. Lithium aluminium hydride (6.6 g, 173 mmol) was added in small portions under vigorous stirring. After the end of the adding stirring was continued at 20° C. for 10 min and the reaction mixture was heated under reflux for 6 h. The reaction mixture was cooled to 0° C., and 30% aq. KOH was added slowly under vigorous stirring until a white solid was precipitated (30 mL). After stirring at 20° C. for 1 h the suspension was filtered on a Cellite bed and the cake was washed with THF (50 mL). After evaporation of the solvent in vacuo, the crude was purified by FC (18/2/80 EtOAc/Et$_3$N/MeOH) to give 6.15 g (88.8%) of 5 (MW=157.258) as yellow oil.

$^1$H NMR (400 MHz, CDCl$_3$): δ=3.61 (t, 2H, J=6.6 Hz), 3.02 (dt, 2H, J=12.3 Hz, 2.6 Hz), 2.56 (t, 2H, J=12.0 Hz), 1.70-1.63 (m, 2H), 1.58-1.50 (m, 2H), 1.42-1.34 (m, 2H), 1.30-1.22 (m, 3H), 1.06 (qd, 2H, J=12.1 Hz, 4.0 Hz).

(1-2) tert-Butyl 4-(4-hydroxybutyl)piperidine-1-carboxylate (6)

A solution of 4-(piperidin-4-yl)butan-1-ol (5, 1.57 g, 10 mmol) and triethylamine (1.50 mL, 10.5 mmol) in CH$_2$Cl$_2$ (30 mL) was cooled to 0° C. Di-tert-butyl dicarbonate (2.30 g, 10.5 mmol) in CH$_2$Cl$_2$ (5 mL) was added dropwise. After the addition, the mixture was stirred at 20° C. for 3 h (monitored by TLC). The mixture was then washed with water (30 mL) and the organic layer concentrated in vacuo. The residue was purified by FC (4/1 PE/EtOAc) to give 6 (2.16 g, 54.7%, MW=253.345) as yellow oil.

$^1$H NMR (400 MHz, CDCl$_3$): δ=4.09 (d, 2H, J=11.9 Hz), 3.67 (t, 2H, J=6.6 Hz), 2.68 (t, 2H, J=12.0 Hz), 1.70-1.63 (m, 2H), 1.61-1.54 (m, 2H), 1.47 (s, 9H), 1.44-1.36 (m, 3H), 1.31-1.25 (m, 2H), 1.09 (qd, 2H, J=12.6 Hz, 4.5 Hz).

(1-3) tert-Butyl 4-(4-(1,3-dioxoisoindolin-2-yl)butyl)piperidine-1-carboxylate (7)

Under N$_2$, phthalimide (0.82 g, 5.52 mmol) and Ph$_3$P (1.45 g, 5.52 mmol) were dissolved in dry THF (10 mL).

This solution was added to a solution of 6 (1.2 g, 4.73 mmol) in dry THF (15 mL). The reaction mixture was stirred at 20° C. for 10 min then cooled to 0° C. Diethyl azodicarboxylate (0.87 mL, 5.52 mmol) was added dropwise at 0° C. Then the cooling bath was removed and the reaction mixture was stirred at 20° C. for 7 h (monitored by TLC). The solvent was evaporated in vacuo, and the residue was purified by FC (1/10 acetone/PE) to give 7 (1.63 g, 89.1%, MW=386.496) as yellow solid.

$^1$H NMR (400 MHz, CDCl$_3$): δ=7.88-7.84 (m, 2H), 7.74-7.71 (m, 2H), 4.15-3.97 (m, 2H), 3.70 (t, 2H, J=7.3 Hz), 2.66 (t, 2H, J=12.3 Hz), 1.72-1.62 (m, 4H), 1.47 (s, 9H), 1.41-1.33 (m, 3H), 1.32-1.26 (m, 2H), 1.07 (qd, 2H, J=12.0 Hz, 4.5 Hz).

tert-Butyl 4-(4-aminobutyl)piperidine-1-carboxylate (8)

Under N$_2$, 7 (1.62 g, 4.19 mmol) and hydrazine hydrate (0.51 mL, 10.3 mmol) were dissolved in dry ethanol (25 mL). The mixture was stirred at 20° C. for 10 min and then heated under reflux (85° C.) for 2 h. During the reaction a white precipitate formed as byproduct. After cooling down to 20° C., the white precipitate was filtered off and washed with additional ethanol (25 mL). Solvent evaporation in vacuo gave a slurry that was dissolved CH$_2$Cl$_2$ (30 mL) and a saturated aqueous solution of K$_2$CO$_3$ (30 mL) was added giving a clear solution. The aqueous layer was extracted with CH$_2$Cl$_2$ (15 mL, 3 times) and the combined organic extracts were washed with brine (30 mL). After drying (MgSO$_4$), the solvent was evaporated in vacuo, and the residue was purified by FC (80/18/2 MeOH/EtOAc/TEA) to give 0.92 g (85.6%) of 8 (MW=256.392) as yellow oil.

$^1$H NMR (400 MHz, CDCl$_3$): δ=4.18-3.95 (m, 2H), 2.78-2.58 (m, 4H), 1.70-1.62 (m, 2H), 1.47 (s, 9H), 1.46-1.40 (m, 2H), 1.39-1.31 (m, 3H), 1.30-1.23 (m, 2H), 1.08 (qd, 2H, J=12.1 Hz, 4.1 Hz).

(E)-N-(4-(Piperidin-4-yl)butyl)-3-(pyridin-3-yl)acrylamide hydrochloride (9a) (for the preparation of FEI 56, FEI 58, FEI 62, FEI 71, FEI 74, FEI 75)

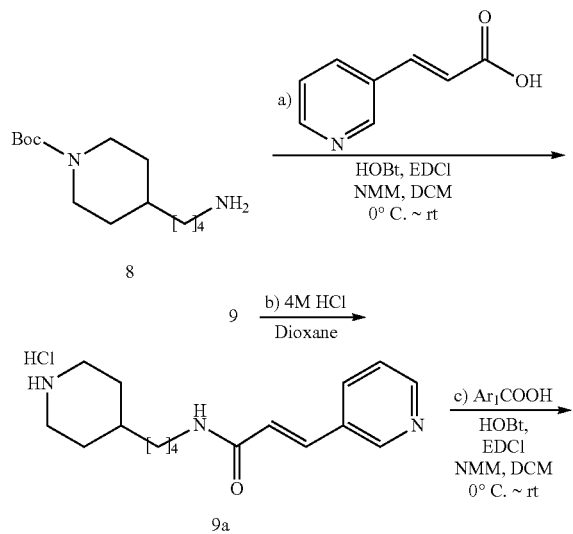

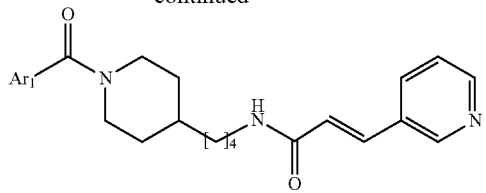

Under N$_2$ atmosphere, HOBt hydrate (0.31 g, ca. 2.0 mmol, MW=125.12+ca. 12% H$_2$O), EDCl (0.33 g ca. 2.1 mmol, MW=155.25) and (E)-3-(3-pyridyl)acrylic acid (0.33 g, 2.2 mmol, MW=149.137) were added sequentially to a cooled (0° C.) solution of 8 (0.515 g. 2 mmol, MW=256.392) in dry CH$_2$Cl$_2$ (7 mL). after stirring at 0° C. for 10 min N-methylmorpholine (0.44 mL) was added drop-wise under stirring at 0° C. The mixture was then allowed to reach room temperature under stirring and stirred until completion of the reaction (monitored by TLC). A saturated aqueous solution of NaHCO$_3$ (15 mL) was added and stirred vigorously for 5 min. The aqueous layer was extracted with CH$_2$Cl$_2$ (5 mL, 3 times). The combined organic extracts and solution were washed with brine (50 mL) and dried (MgSO$_4$). The solvent was evaporated in vacuo and the residue purified by FC (EtOAc) to give acrylamide 9 (0.643 g, 83%, MW=387.513) as a yellow oil that was used directly in the following reaction. Solution of compound 9 (0.39 g, 1 mmol, MW=387.513) in 4M HCl/dioxane solution (1.0 mL) was stirred at 20° C. for 30 min (monitored by TLC). After solvent evaporation in vacuo, salt 9a (0.299 g, 92.3%, MW=323.889) was obtained as a white solid; it was used in the next step without purification.

$^1$H NMR (400 MHz, CD$_3$D): δ=9.15 (d, 1H, J=1.5 Hz), 8.91 (dt, 1H, J=8.3 Hz, 1.6 Hz), 8.86 (d, 1H, J=5.7 Hz), 8.17 (dd, 1H, J=8.2 Hz, 5.8 Hz), 7.67 (d, 1H, J=15.8 Hz), 7.06 (d, 1H, J=15.8 Hz), 3.62 (t, 2H, J=6.1 Hz), 3.45 (t, 2H, J=7.1 Hz), 3.35-3.31 (m, 3H), 3.19-3.09 (m, 2H), 2.09-1.99 (m, 2H), 1.95-1.84 (m, 4H).

Yield: 0.53 g (82%), white solid, $^1$H NMR (400 MHz, CD$_3$OD): δ=9.12 (d, 1H, J=1.6 Hz), 8.90-8.83 (m, 2H), 8.15 (dd, 1H, J=8.2 Hz, 5.8 Hz), 7.67 (d, 1H, J=15.8 Hz), 7.01 (d, 1H, J=15.8 Hz), 3.42-3.34 (m, 4H), 2.99 (td, 2H, J=12.7 Hz, 2.3 Hz), 2.02-1.94 (m, 2H), 1.69-1.58 (m, 3H), 1.50-1.34 (m, 6H).

(E)-N-(4-(1-(2,4-Dimethoxybenzoyl)piperidin-4-yl)butyl)-3-(pyridin-3-yl)acrylamide (FEI-56)

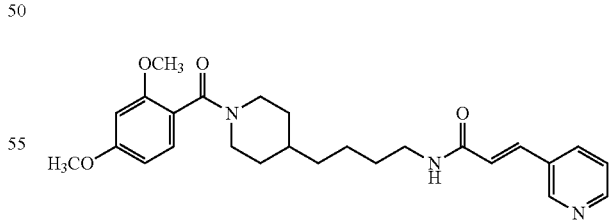

Under N$_2$ Atm., HOBt hydrate (24.3 mg, 0.15 mmol), EDCl (34.5 mg, 0.22 mmol) and 2,4-dimethoxybenzoic acid (35.7 mg, 0.19 mmol, MW=182.179) were sequentially added to a cooled (0° C.) solution of compound 9a (48.8 mg, 0.15 mmol, MW=323.419) in dry CH$_2$Cl$_2$ (2 mL). The reaction mixture was stirred for 10 min and N-methylmorpholine (0.05 mL, 0.45 mmol) was added at 0° C. The resulting mixture was stirred at 20° C. overnight (monitored by TLC). Saturated aqueous of NaHCO$_3$ (5 mL) was added and stirred for 5 min. The aqueous layer was extracted with CH$_2$Cl$_2$ (5 mL, 3 times) and the combined organic extracts were washed with brine (20 mL). After drying (MgSO$_4$) and evaporation of the solvent in vacuo, the residue was purified by FC (EtOAc), giving FEI-56 (47.8 mg 70.5%, MW=451.247) as white foam.

$^1$H NMR (400 MHz, CDCl$_3$): δ=8.63-8.60 (m, 1H), 8.45 (td, 1H, J=4.5 Hz, 1.2 Hz), 7.65-7.60 (m, 1H), 7.49 (d, 1H, J=15.8 Hz), 7.21-7.16 (m, 1H), 7.10-7.02 (m, 1H), 6.85-6.67 (m, 1H), 6.45 (d, 1H, J=15.8 Hz), 6.42-6.37 (m, 1H), 6.36-6.33 (m, 1H), 4.64 (d, 1H, J=12.2 Hz), 3.72-3.66 (m, 6H), 3.41 (d, 1H, J=13.0 Hz), 3.28-3.20 (m, 2H), 2.92-2.73 (m, 1H), 2.67-2.58 (m, 1H), 1.68 (d, 1H, J=12.5 Hz), 1.52-1.33 (m, 4H), 1.28-1.02 (m, 5H), 0.95-0.74 (m, 1H); $^{13}$C NMR (100 MHz, CDCl$_3$): δ=167.7, 165.3, 161.5, 156.7, 150.1, 149.1, 136.5, 134.3, 130.9, 128.7, 123.6, 123.5, 118.8, 104.8, 98.5, 55.5, 53.5, 47.7, 42.0, 39.7, 36.1, 36.0, 32.8, 32.0, 29.7, 24.0; HRMS (ESI) for C$_{26}$H$_{33}$N$_3$O$_4$ [M+H]$^+$ calcd: 452.2549, found: 452.2550.

FEI-58, FEI-62, FEI-71, FEI-74 and FEI 75 were prepared from salt 9a (48.8 mg, 0.15 mmol) and different carboxylic acids (Ar$_1$COOH, 0.18 mmol) according to the same procedure as that used to prepare FEI-56.

(E)-N-(4-(1-(2,6-Dimethoxybenzoyl)piperidin-4-yl)butyl)-3-(pyridin-3-yl)acrylamide (FEI-58)

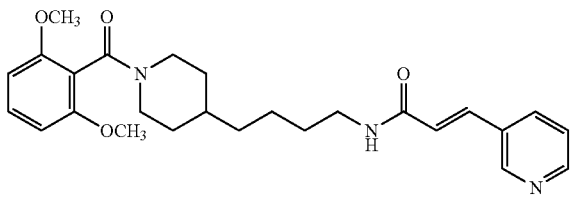 [SMILES: COc1cccc(OC)c1C(=O)N1CCC(CCCCNC(=O)/C=C/c2cccnc2)CC1]

Ar$_1$COOH=2,6-dimethoxybenzoic acid. Yield: 43.6 mg (64.4%, MW=451.247), white foam. $^1$H NMR (400 MHz, CDCl$_3$): δ=8.63-8.59 (m, 1H), 8.48-8.44 (m, 1H), 7.67-7.62 (m, 1H), 7.49 (d, 1H, J=15.8 Hz), 7.21-7.13 (m, 2H), 6.80-6.64 (m, 1H), 6.49-6.43 (m, 3H), 4.69 (d, 1H, J=12.8 Hz), 3.70 (s, 3H), 3.68 (s, 3H), 3.37 (d, 1H, J=13.5 Hz), 3.27-3.20 (m, 2H), 2.88-2.82 (m, 1H), 2.65 (td, 1H, J=12.6 Hz, 2.5 Hz), 1.68 (d, 1H, J=13.1 Hz), 1.50-1.34 (m, 4H), 1.29-1.12 (m, 5H), 1.06-0.96 (m, 1H); $^{13}$C NMR (100 MHz, CDCl$_3$): δ=165.2, 156.4, 150.1, 149.1, 136.5, 136.4, 134.3, 130.9, 130.1, 123.6, 123.5, 114.8, 103.9, 55.8, 46.9, 41.7, 39.8, 36.1, 36.0, 32.8, 31.9, 29.8, 24.0; HRMS (ESI) for C$_{26}$H$_{33}$N$_3$O$_4$ [M+H]$^+$ calcd: 452.2549, found: 452.2545.

(E)-3-(Pyridin-3-yl)-N-(4-(1-(2,4,6-trimethoxybenzoyl)piperidin-4-yl)butyl)acrylamide (FEI-62)

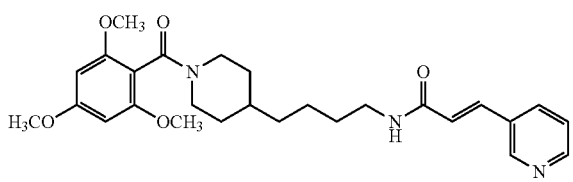 [SMILES: COc1cc(OC)c(C(=O)N2CCC(CCCCNC(=O)/C=C/c3cccnc3)CC2)c(OC)c1]

Ar$_1$COOH=2,4,6-trimethoxybenzoic acid. Yield: 42.3 mg (58.5%, MW=481.2577), white foam. $^1$H NMR (400 MHz, CDCl$_3$): δ=8.64 (d, 1H, J=1.4 Hz), 8.48 (dd, 1H, J=4.7 Hz, 1.2 Hz), 7.6t (dt, 1H, J=7.9 Hz, 1.9 Hz), 7.51 (d, 1H, J=15.7 Hz), 7.22-7.18 (m, 1H), 6.44 (d, 1H, J=15.7 Hz), 6.40-6.35 (m, 1H), 6.03-6.01 (m, 2H), 4.69 (d, 1H, J=13.0 Hz), 3.72 (s, 3H), 3.68 (d, 6H, J=6.6 Hz), 3.42 (d, 1H, J=13.2 Hz), 3.24 (dd, 2H, J=13.4 Hz, 7.1 Hz), 2.89-2.79 (m, 1H), 2.64 (td, 1H, J=12.5 Hz, 2.3 Hz), 1.68 (d, 1H, J=12.5 Hz), 1.51-1.43 (m, 3H), 1.34-1.25 (m, 2H), 1.23-1.16 (m, 3H), 1.13-0.96 (m, 2H); $^{13}$C NMR (100 MHz, CDCl$_3$): δ=165.2, 161.8, 157.4, 150.2, 149.2, 136.7, 134.3, 130.9, 123.6, 123.3, 121.0, 107.9, 90.6, 55.8, 55.7, 55.4, 47.0, 41.8, 39.7, 36.2 (2C), 32.9, 31.9, 29.8, 24.0; HRMS (ESI) for C$_{27}$H$_{35}$N$_3$O$_5$ [M+H]$^+$ calcd: 482.2655, found: 482.2652.

(E)-N-(4-(1-(3-Methoxyfuran-2-carbonyl)piperidin-4-yl)butyl)-3-(pyridin-3-yl)acrylamide (FEI-71)

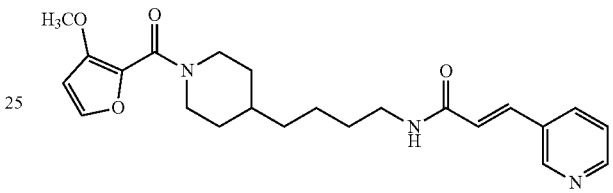

Ar$_1$COOH=3-methoxyfuran-2-carboxylic acid. Yield: 40 mg (64.8%, MW=411.2158), white foam. $^1$H NMR (400 MHz, CDCl$_3$): δ=8.74-8.63 (m, 1H), 8.55-8.47 (m, 1H), 7.70 (d, 1H, J=7.8 Hz), 7.53 (d, 1H, J=15.8 Hz), 7.27 (d, 1H, J=1.9 Hz), 7.25-7.21 (m, 1H), 6.47 (d, 1H, J=15.8 Hz), 6.27 (d, 1H, J=1.9 Hz), 6.25 (brs, 1H, N—H), 4.52-4.27 (m, 1H), 4.09-3.86 (m, 1H), 3.77 (s, 3H), 3.32 (q, 2H, J=6.0 Hz), 2.99-2.59 (m, 2H), 1.69-1.61 (m, 2H), 1.53-1.46 (m, 2H), 1.35-1.27 (m, 2H), 1.24-1.18 (m, 3H), 1.11 (qd, 2H, J=12.3 Hz, 3.8 Hz); $^{13}$C NMR (100 MHz, CDCl$_3$): δ=165.2, 159.8, 150.2, 149.6, 149.0, 143.2, 136.9, 134.3, 131.0, 123.8, 123.6, 123.2, 102.0, 58.7, 47.3, 43.1, 39.8, 36.1, 36.0, 33.0, 31.9, 29.8, 24.0; HRMS (ESI) for C$_{23}$H$_{29}$N$_3$O$_4$ [M+H]$^+$ calcd: 412.2236, found: 412.2239.

(E)-N-(4-(1-(Isoxazole-5-carbonyl)piperidin-4-yl)butyl)-3-(pyridin-3-yl)acrylamide (FEI-74)

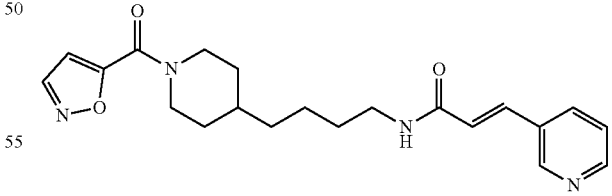

Ar$_1$COOH=1,2-oxazole-5 carboxylic acid. Yield: 46.5 mg (81.1%, MW=382.2005), white foam. $^1$H NMR (400 MHz, CDCl$_3$): δ=8.67 (s, 1H), 8.50 (d, 1H, J=4.1 Hz), 8.23 (d, 1H, J=1.7 Hz), 7.71 (d, 1H, J=8.0 Hz), 7.55 ((d, 1H, J=15.7 Hz), 7.24 (dd, 1H, J=7.7 Hz, 4.9 Hz), 6.64 (d, 1H, J=1.7 Hz), 6.42 (d, 1H, J=15.7 Hz), 5.92 (brs, 1H, N—H), 4.56 (d, 1H, J=13.3 Hz), 4.01 (d, 1H, J=13.3 Hz), 3.33 (q, 2H, J=6.4 Hz), 3.03 (t, 1H, J=12.0 Hz), 2.70 (td, 1H, J=12.7 Hz, 2.0 Hz), 1.73 (t, 2H, J=17.2 Hz), 1.54-1.47 (m, 3H), 1.37-1.29 (m, 2H), 1.27-1.22 (m, 2H), 1.18-1.11 (m, 2H); $^{13}$C NMR (100 MHz, CDCl$_3$): δ=167.1, 164.1, 156.9, 150.3, 150.1, 149.1, 137.3, 134.4, 130.7, 123.7, 122.9, 106.8, 47.0, 43.2, 39.7, 36.0, 35.9, 32.9, 31.8, 29.9, 23.9; HRMS (ESI) for C$_{21}$H$_{26}$N$_4$O$_3$ [M+H]$^+$ calcd: 382.2083, found: 382.2073.

(E)-N-(4-(1-(4-Formyl-2,6-dimethoxybenzoyl)piperidin-4-yl)butyl)-3-(pyridin-3-yl)acrylamide (FEI-75)

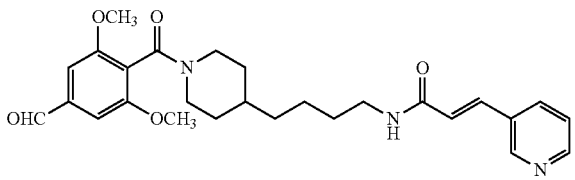 [SMILES: COc1cc(C=O)cc(OC)c1C(=O)N1CCC(CCCCNC(=O)/C=C/c2cccnc2)CC1]

Ar$_1$COOH=4-formyl-2,6-dimethoxybenzoic acid. Yield: 38.4 mg (53.4%, MW=479.2420), white foam. $^1$H NMR (400 MHz, CDCl$_3$): δ=9.86 (s, 1H), 8.65 (s, 1H), 8.49 (dd, 1H, J=4.7 Hz, 1.1 Hz), 7.69 (d, 1H, J=7.8 Hz), 7.53 (d, 1H, J=15.6 Hz), 7.22 (dd, 1H, J=7.7 Hz, 4.9 Hz), 7.00 (d, 2H, J=3.3 Hz), 6.40 (d, 1H, J=15.6 Hz), 5.96 (brs, 1H, N—H), 4.69 (d, 1H, J=13.0 Hz), 3.81 (s, 3H), 3.79 (s, 3H), 3.34-3.26 (m, 3H), 3.28 (td, 1H, J=13.0 Hz, 2.4 Hz), 2.68 (td, 1H, J=12.8 Hz, 2.4 Hz), 1.77-1.68 (m, 2H), 1.53-1.44 (m, 3H), 1.35-1.26 (m, 2H), 1.24-1.19 (m, 2H), 1.16-0.97 (m, 2H); $^{13}$C NMR (100 MHz, CDCl$_3$): δ=191.4, 165.2, 163.8, 157.3, 150.2, 149.1, 137.9, 137.2, 134.4, 130.7, 123.7, 122.9, 120.8, 105.3, 56.1, 46.9, 41.7, 39.7, 36.1, 36.0, 32.8, 31.8, 29.8, 24.0; HRMS (ESI) for C$_{27}$H$_{33}$N$_3$O$_5$ [M+H]$^+$ calcd: 480.2498, found: 480.2500.

(E)-N-(4-(Piperidin-4-yl)butyl)-3-(pyridazin-4-yl) acrylamide hydrochloride (9d) (for the preparation of FEI 95, FEI 96, FEI 97, FEI 98)

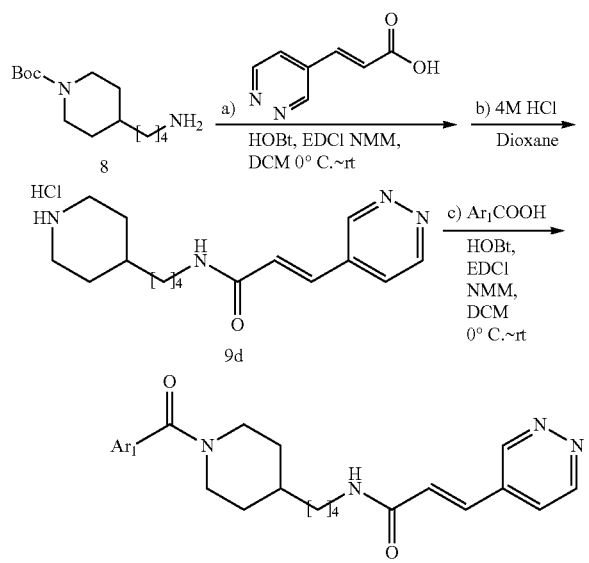

Salt 9d was prepared from amine 8 (0.26 g, 1.0 mmol) and (E)-3-(pyridazin-4-yl)acrylic acid (0.18 g, 1.2 mmol) according to the same procedure as that used to prepare 9a (2 steps).

Yield: 0.25 g (77%, MW=323.874), white solid. $^1$H NMR (400 MHz, CD$_3$OD): δ=9.44-9.41 (m, 1H), 9.28 (dd, 1H, J=5.4 Hz, 0.7 Hz), 7.85 (dd, 1H, J=5.3 Hz, 2.2 Hz), 7.42 (d, 1H, J=16.0 Hz), 7.01 (d, 1H, J=16.0 Hz), 3.28-3.15 (m, 4H), 2.88-2.75 (m, 2H), 1.84-1.72 (m, 2H), 1.54-1.40 (m, 3H), 1.36-1.18 (m, 6H).

FEI 95-98 were prepared from salt 9d (48.6 mg, 0.15 mmol) and different carboxylic acids Ar$_1$COOH (0.18 mmol) according to the same procedure as that used to prepare FEI-56.

(E)-N-(4-(1-Benzoylpiperidin-4-yl)butyl)-3-(pyridazin-4-yl)acrylamide (FEI-95)

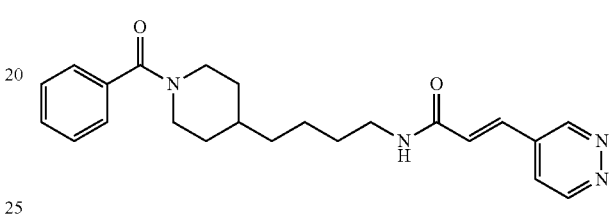

Ar$_1$COOH=benzoic acid. Yield: 47.8 mg (81.2%, MW=392.2212), white foam. $^1$H NMR (400 MHz, CDCl$_3$): δ=9.19 (s, 1H), 9.10 (d, 1H, J=4.9 Hz), 7.43 (d, 1H, J=15.8 Hz), 7.36 (dd, 1H, J=5.1 Hz, 1.7 Hz), 7.33-7.28 (m, 5H), 7.10-6.97 (m, 1H, N—H), 6.80 (dd, 1H, J=15.8 Hz, 4.6 Hz), 4.66-4.54 (m, 1H), 3.71-3.57 (m, 1H), 3.28 (q, 2H, J=6.8 Hz), 2.90 (t, 1H, J=10.4 Hz), 2.67 (t, 1H, J=9.8 Hz), 1.76-1.51 (m, 2H), 1.51-1.41 (m, 3H), 1.34-1.25 (m, 2H), 1.23-1.18 (m, 2H), 1.14-0.98 (m, 2H); $^{13}$C NMR (100 MHz, CDCl$_3$): δ=170.4, 164.2, 151.7, 149.3, 136.3, 133.8, 133.5, 129.6, 128.5, 128.4, 126.7, 124.0, 48.1, 42.6, 39.8, 36.1, 36.0, 32.9, 31.0, 29.6, 24.0; HRMS (ESI) for C$_{23}$H$_{28}$N$_4$O$_2$ [M+H]$^+$ calcd: 393.2285, found: 393.2283.

(E)-N-(4-(1-(Furan-2-carbonyl)piperidin-4-yl)butyl)-3-(pyridazin-4-yl)acrylamide (FEI-96)

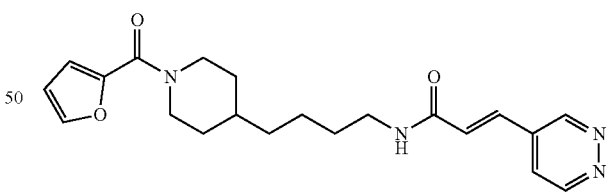

Ar$_1$COOH=furan-2-carboxylic acid. Yield: 45.6 mg (79.5%, MW=382.2005), white foam. $^1$H NMR (400 MHz, CDCl$_3$): δ=9.24 (s, 1H), 9.13 (s, 1H), 7.46 (d, 1H, J=15.8 Hz), 7.43-7.38 (m, 2H), 6.91-6.86 (m, 1H, N—H), 6.85-6.80 (m, 2H), 6.41-6.38 (m, 1H), 4.55-4.27 (m, 2H), 3.33 (q, 2H, J=6.7 Hz), 3.08-2.52 (m, 2H), 1.69 (d, 2H, J=12.8 Hz), 1.55-1.44 (m, 3H), 1.36-1.28 (m, 2H), 1.25-1.20 (m, 2H), 1.12 (qd, 2H, J=12.2 Hz, 3.3 Hz); $^{13}$C NMR (100 MHz, CDCl$_3$): δ=164.2, 159.3, 151.9, 149.3, 148.8, 143.6, 134.1, 133.4, 128.6, 124.0, 115.6, 111.1, 46.7, 43.4, 39.8, 36.1, 36.0, 32.9, 31.0, 29.6, 24.0; HRMS (ESI) for C$_{21}$H$_{26}$N$_4$O$_3$ [M+H]$^+$ calcd: 383.20777, found: 383.20768.

19

(E)-3-(Pyridazin-4-yl)-N-(4-(1-(thiophene-2-carbonyl)piperidin-4-yl)butyl)acrylamide (FEI-97)

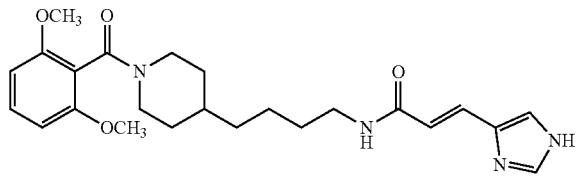 [SMILES: COc1cccc(OC)c1C(=O)N1CCC(CCCCNC(=O)/C=C/c2c[nH]cn2)CC1]

Ar$_1$COOH=thiophene-2-carboxylic acid. Yield: 45.8 mg (76.7%, MW=398.1776), white foam. $^1$H NMR (400 MHz, CDCl$_3$): δ=9.22 (s, 1H), 9.12 (s, 1H), 7.46 (d, 1H, J=15.7 Hz), 7.41-7.37 (m, 1H), 7.36 (dt, 1H, J=5.0 Hz, 1.1 Hz), 7.19 (t, 1H, J=3.6 Hz), 6.96 (t, 1H, J=4.1 Hz), 6.77 (d, 1H, J=15.7 Hz), 6.74-6.71 (m, 1H, N—H), 4.49-4.13 (m, 2H), 3.32 (q, 2H, J=6.4 Hz), 2.96-2.79 (m, 2H), 1.68 (d, 2H, J=12.6 Hz), 1.54-1.42 (m, 3H), 1.36-1.28 (m, 2H), 1.26-1.20 (m, 2H), 1.11 (qd, 2H, J=12.2 Hz, 3.7 Hz); $^{13}$C NMR (100 MHz, CDCl$_3$): δ=164.1, 163.5, 151.8, 149.3, 137.3, 134.2, 133.4, 128.5, 128.3, 126.7, 124.0, 124.0, 46.7, 43.4, 39.8, 36.1, 36.0, 32.9, 31.0, 29.7, 24.0; HRMS (ESI) for C$_{21}$H$_{26}$N$_4$O$_2$S [M+H]$^+$ calcd: 399.18492, found: 399.18484.

20

(E)-N-(4-(1-(2,6-Dimethoxybenzoyl)piperidin-4-yl)butyl)-3-(pyridazin-4-yl)acrylamide (FEI-98)

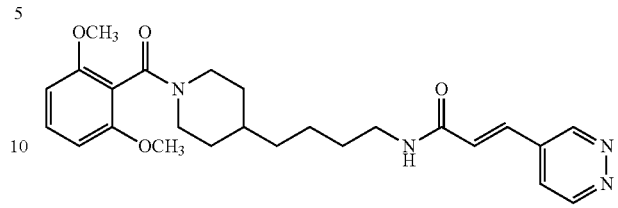

Ar$_1$COOH=2,6-dimethoxybenzoic acid. Yield: 44.3 mg (65.3%, MW=452.2424), white foam. $^1$H NMR (400 MHz, CDCl$_3$): δ=9.15 (s, 1H), 9.08 (d, 1H, J=5.3 Hz), 7.40 (d, 1H, J=15.8 Hz), 7.34 (dd, 1H, J=5.3 Hz, 2.3 Hz), 7.21-7.12 (m, 2H), 6.79 (d, 1H, J=15.8 Hz), 6.47 (d, 2H, J=8.4 Hz), 4.70 (d, 1H, J=13.2 Hz), 3.70 (s, 3H), 3.69 (s, 3H), 3.38 (d, 1H, J=13.5 Hz), 3.24 (q, 2H, J=6.2 Hz), 2.86 (td, 1H, J=12.7 Hz, 2.3 Hz), 2.67 (td, 1H, J=12.8 Hz, 2.7 Hz), 1.71 (d, 1H, J=12.6 Hz), 1.50-1.36 (m, 4H), 1.32-1.23 (m, 2H), 1.22-1.15 (m, 2H), 1.13-1.0 (m, 2H); $^{13}$C NMR (100 MHz, CDCl$_3$): δ=165.4, 164.3, 156.6, 151.6, 149.3, 133.6, 133.5, 130.2, 128.9, 123.9, 114.7, 103.9, 55.8, 47.0, 41.8, 39.8, 36.1, 36.0, 32.9, 31.9, 29.6, 24.0; HRMS (ESI) for C$_{25}$H$_{32}$N$_4$O$_4$ [M+H]$^+$ calcd: 453.24963, found: 453.24959.

General Procedure for the Synthesis of FK-866 Analogues FEI 80, 81, 82, 83, 85

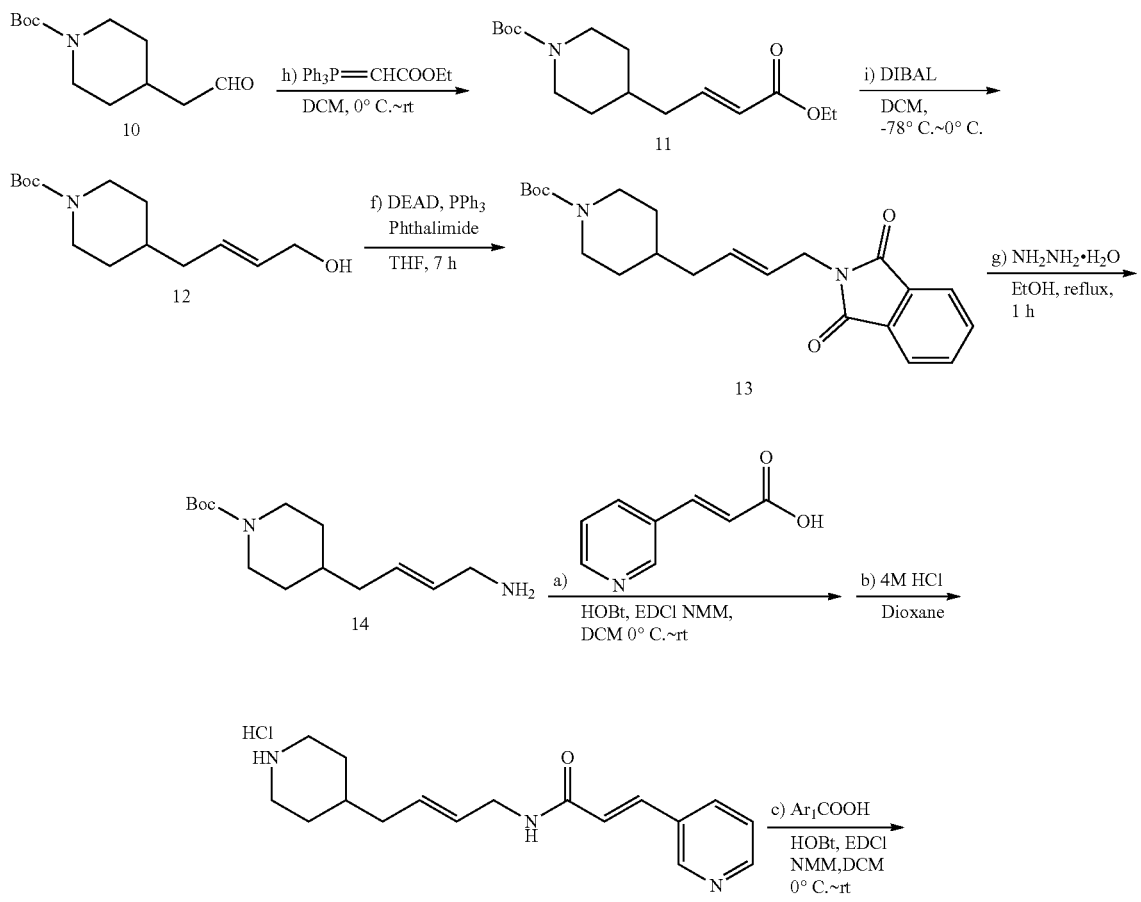

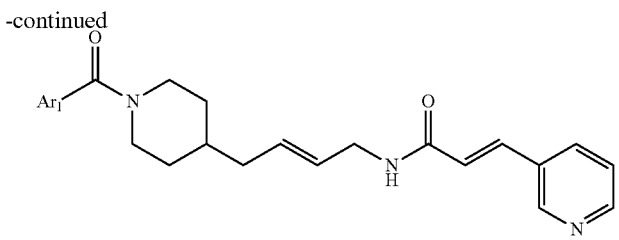

tert-Butyl (E)-4-(4-ethoxy-4-oxobut-2-en-1-yl)piperidine-1-carboxylate (11)

tert-Butyl 4-(2-oxoethyl)piperidine-1-carboxylate (10, 1.14 g, 5.0 mmol, MW=227.317, Aldrich or Fluochem, CAS 142374-19-4) was dissolved in $CH_2Cl_2$ (20 mL), (carbethoxymethylene)triphenylphosphorane (3.14 g, 9.0 mmol) was added in small portions under vigorous stirring at 0° C. The mixture stirred at 20° C. for 3 h, then concentrated, the residue was purified by FC (5/1 PE/EtOAc) to give 1.39 g (93.3%) of 11 (MW=297.399) as colorless oil. $^1$H NMR (400 MHz, $CDCl_3$): δ=6.94 (dt, 1H, J=15.6 Hz, 7.7 Hz), 5.84 (dt, 1H, J=15.6 Hz, 1.4 Hz), 4.20 (q, 2H, J=7.0 Hz), 4.16-4.01 (m, 2H), 2.69 (t, 2H, J=11.4 Hz), 2.17 (t, 2H, J=7.5 Hz), 1.73-1.64 (m, 2H), 1.62-1.54 (m, 1H), 1.47 (s, 9H), 1.31 (t, 3H, J=7.4 Hz), 1.15 (qd, 2H, J=11.8 Hz, 3.0 Hz).

tert-Butyl (E)-4-(4-hydroxybut-2-en-1-yl)piperidine-1-carboxylate (12)

1M DIBAL in $CH_2Cl_2$ (10 mL) added slowly to ester 11 (1.39 g, 4.68 mmol) in $CH_2Cl_2$ (10 mL) under nitrogen atmosphere at −78° C. over 20 min. The mixture keep stirred at −78° C. for 40 min (monitored by TLC), and methanol (2.0 mL) was added drop-wise to quench DIBAL. The cold solution was further stirred for 10 min before pouring into saturated sodium, potassium tartrate salt solution (30 mL). The mixture was vigorously stirred at 20° C. for 3 h until it turned clear. The organic phase was collected and dried, concentrated to give 1.17 g (97.9%) of alcohol 12 (MW=255.361) as colorless oil, which was used in the next step without purification. $^1$H NMR (400 MHz, $CDCl_3$): δ=5.70-5.65 (m, 2H), 4.18-4.01 (m, 4H), 2.69 (t, 2H, J=12.6 Hz), 2.02 (t, 2H, J=5.6 Hz), 1.72-1.62 (m, 3H), 1.47 (s, 9H), 1.11 (qd, 2H, J=12.2 Hz, 3.9 Hz).

tert-Butyl (E)-4-(4-(1,3-dioxoisoindolin-2-yl)but-2-en-1-yl)piperidine-1-carboxylate (13)

Compound 13 (MW=384.508) was prepared from 12 (0.75 g, 2.94 mmol) according to the same procedure as that used to prepare 7, yield: 0.98 g (86.7%), white solid. $^1$H NMR (400 MHz, $CDCl_3$): δ=7.87 (dd, 2H, J=5.5 Hz, 3.1 Hz), 7.74 (dd, 2H, J=5.5 Hz, 3.0 Hz), 5.77-5.67 (m, 1H), 5.58-5.49 (m, 1H), 4.26 (dd, 2H, J=6.2 Hz, 0.7 Hz), 4.17-3.95 (m, 2H), 2.67 (t, 2H, J=10.6 Hz), 1.98 (t, 2H, J=7.0 Hz), 1.67-1.61 (m, 2H), 1.49-1.41 (m, 1H), 1.47 (s, 9H), 1.06 (qd, 2H, J=12.0 Hz, 3.0 Hz).

tert-Butyl (E)-4-(4-aminobut-2-en-1-yl)piperidine-1-carboxylate (14)

Primary amine 14 (MW=254.376) was prepared from 13 (0.8 g, 2.08 mmol) according to the same procedure as that used to prepare 8, yield: 0.45 g (85%), yellow oil. It was used directly in the next step without purification.

(E)-N-((E)-4-(Piperidin-4-yl)but-2-en-1-yl)-3-(pyridin-3-yl)acrylamide hydrochloride (15)

Salt 15 (MW=321.872) was prepared from amine 14 (0.45 g, 1.76 mmol) and (E)-3-(pyridin-3-yl)acrylic acid (0.31 g, 2.10 mmol) according to the same procedure as that used to prepare 9a (2 steps). Yield: 0.48 g (84.7%), white solid. $^1$H NMR (400 MHz, $CD_3OD$): δ=9.01 (d, 1H, J=1.6 Hz), 8.77 (dt, 1H, J=8.2 Hz, 1.4 Hz), 8.74 (d, 1H, J=5.6 Hz), 8.04 (dd, 1H, J=8.2 Hz, 5.8 Hz), 7.56 (d, 1H, J=15.8 Hz), 6.92 (d, 1H, J=15.8 Hz), 5.63-5.44 (m, 2H), 3.81 (d, 2H, J=5.6 Hz), 3.28 (dt, 2H, J=12.6 Hz, 1.8 Hz), 2.87 (td, 2H, J=12.6 Hz, 2.5 Hz), 1.99 (t, 2H, J=6.3 Hz), 1.89-1.81 (m, 2H), 1.65-1.53 (m, 1H), 1.37-1.23 (m, 2H).

FEI 80, 81, 82, 83, 85 were prepared from salt 15 (48.2 mg, 0.15 mmol) and different carboxylic acids $Ar_1COOH$ (0.2 mmol) using the same procedure as that applied for the preparation of FEI-56.

(E)-N-((E)-4-(1-Benzoylpiperidin-4-yl)but-2-en-1-yl)-3-(pyridin-3-yl)acrylamide (FEI-80)

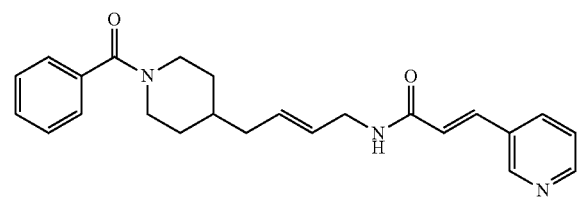 [SMILES: O=C(/C=C/c1cccnc1)NC/C=C/CC1CCN(C(=O)c2ccccc2)CC1]

$Ar_1COOH$=benzoic acid, Yield: 48.5 mg (83%, MW=389.2103), white foam. $^1$H NMR (400 MHz, $CDCl_3$): δ=8.74-8.60 (m, 1H), 8.53-8.44 (m, 1H), 7.68 (d, 1H, J=7.8 Hz), 7.53 (d, 1H, J=15.8 Hz), 7.34-7.28 (m, 5H), 7.25-7.21 (m, 1H), 6.44 (d, 1H, J=15.8 Hz), 6.27-6.22 (m, 1H, N—H), 5.58-5.40 (m, 2H), 4.67-4.57 (m, 1H), 3.87 (t, 2H, J=5.6 Hz), 3.72-3.59 (m, 1H), 2.95-2.80 (m, 1H), 2.72-2.61 (m, 1H), 1.94 (t, 2H, J=6.8 Hz), 1.76-1.66 (m, 1H), 1.58-1.45 (m, 2H), 1.25-1.04 (m, 2H); $^{13}$C NMR (100 MHz, $CDCl_3$): δ=170.3, 165.0, 150.2, 149.0, 137.2, 136.3, 134.4, 130.8, 129.8, 129.5, 128.4, 127.7, 126.8, 123.8, 122.9, 48.0, 42.4, 41.6, 39.1, 36.2, 32.5, 31.6; HRMS (ESI) for $C_{24}H_{27}N_3O_2$ [M+H]$^+$ calcd: 390.2181, found: 390.2186.

(E)-N-((E)-4-(1-(2,6-Dimethoxybenzoyl)piperidin-4-yl)but-2-en-1-yl)-3-(pyridin-3-yl)acrylamide (FEI-81)

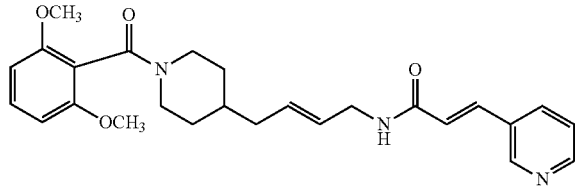 [SMILES: COc1cccc(OC)c1C(=O)N1CCC(C/C=C/CNC(=O)/C=C/c2cccnc2)CC1]

Ar$_1$COOH=2,6-dimethoxybenzoic acid. Yield: 40.8 mg (60.5%, MW=449.2315), white foam. $^1$H NMR (400 MHz, CDCl$_3$): δ=8.75-8.70 (m, 1H), 8.59-8.55 (m, 1H), 7.76 (d, 1H, J=7.4 Hz), 7.62 (d, 1H, J=15.7 Hz), 7.32-7.23 (m, 2H), 6.57-6.51 (m, 3H), 6.34 (brs, 1H, N—H), 5.63 (dt, 1H, J=15.7 Hz, 6.7 Hz), 5.52 (dt, 1H, J=15.0 Hz, 5.5 Hz), 4.79 (d, 1H, J=12.5 Hz), 3.95 (t, 2H, J=5.3 Hz), 3.79 (d, 6H, J=7.9 Hz), 3.47 (d, 1H, J=12.5 Hz), 2.90 (t, 1H, J=12.0 Hz), 2.75 (t, 1H, J=12.3 Hz), 2.0 (t, 2H, J=5.9 Hz), 1.81-1.74 (m, 1H), 1.60-1.52 (m, 2H), 1.34-1.11 (m, 2H); $^{13}$C NMR (100 MHz, CDCl$_3$): δ=165.2, 156.6, 150.3, 149.2, 137.2, 134.3, 131.0, 130.8, 130.1, 127.5, 124.7, 123.7, 123.0, 114.9, 103.9, 55.8, 46.9, 41.6, 41.5, 39.2, 36.3, 32.5, 31.6; HRMS (ESI) for C$_{26}$H$_{31}$N$_3$O$_4$ [M+H]$^+$ calcd: 450.2393, found: 450.2388.

(E)-3-(Pyridin-3-yl)-N-((E)-4-(1-(2,4,6-trimethoxybenzoyl)piperidin-4-yl)but-2-en-1-yl)acrylamide (FEI-82)

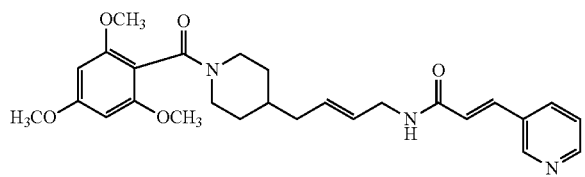 [SMILES: COc1cc(OC)c(C(=O)N2CCC(C/C=C/CNC(=O)/C=C/c3cccnc3)CC2)c(OC)c1]

Ar$_1$COOH=2,4,6-trimethoxybenzoic acid. Yield: 42.2 mg (58.7%, MW=479.2420), white foam. $^1$H NMR (400 MHz, CDCl$_3$): δ=8.74-8.69 (m, 1H), 8.56 (d, 1H, J=3.6 Hz), 7.75 (d, 1H, J=7.5 Hz), 7.61 (d, 1H, J=15.6 Hz), 7.33-7.26 (m, 1H), 6.54 (d, 1H, J=15.6 Hz), 6.45 (brs, 1H, N—H), 6.14-6.09 (m, 2H), 5.62 (dt, 1H, J=15.1 Hz, 6.4 Hz), 5.52 (dt, 1H, J=15.2 Hz, 5.2 Hz), 4.76 (d, 1H, J=12.5 Hz), 3.94 (t, 2H, J=4.7 Hz), 3.80 (s, 3H), 3.76 (d, 6H, J=7.8 Hz), 3.51 (d, 1H, J=12.6 Hz), 2.92 (t, 1H, J=11.8 Hz), 2.73 (t, 1H, J=12.0 Hz), 1.99 (t, 2H, J=6.0 Hz), 1.79-1.72 (m, 1H), 1.60-1.50 (m, 2H), 1.25-1.09 (m, 2H); $^{13}$C NMR (100 MHz, CDCl$_3$): δ=165.3, 165.0, 161.8, 157.7, 157.5, 150.2, 149.2, 137.0, 134.3, 130.9, 130.8, 127.5, 123.6, 123.1, 90.6, 55.8, 55.4, 46.9, 41.6, 41.5, 39.2, 36.3, 32.5, 31.6; HRMS (ESI) for C$_{27}$H$_{33}$N$_3$O$_5$ [M+H]$^+$ calcd: 480.2498, found: 480.2491.

(E)-N-((E)-4-(1-(Furan-2-carbonyl)piperidin-4-yl)but-2-en-1-yl)-3-(pyridin-3-yl)acrylamide (FEI-83)

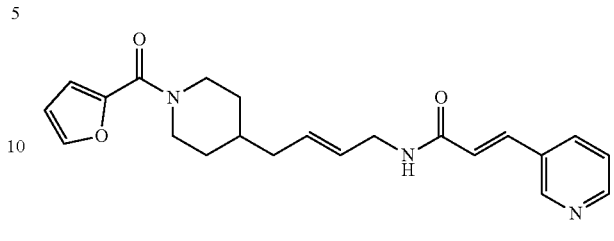

Ar$_1$COOH=furan-2-carboxylic acid. Yield: 45.7 mg (80.3%, MW=379.1896), white foam. $^1$H NMR (400 MHz, CDCl$_3$): δ=8.78-8.71 (m, 1H), 8.61-8.55 (m, 1H), 7.78 (d, 1H, J=7.6 Hz), 7.64 (d, 1H, J=15.8 Hz), 7.48 (s, 1H), 7.34-7.29 (m, 1H), 6.94 (d, 1H, J=3.2 Hz), 6.54 (d, 1H, J=15.8 Hz), 6.49-6.45 (m, 1H), 6.27-6.17 (m, 1H, N—H), 5.64 (dt, 1H, J=15.3 Hz, 6.9 Hz), 5.54 (dt, 1H, J=15.3 Hz, 5.8 Hz), 4.60-4.42 (m, 2H), 3.99 (t, 2H, J=5.3 Hz), 3.13-2.60 (m, 2H), 2.03 (t, 2H, J=6.6 Hz), 1.76 (d, 2H, J=12.6 Hz), 1.33-1.18 (m, 3H); $^{13}$C NMR (100 MHz, CDCl$_3$): δ=164.9, 159.2, 150.3, 149.0, 148.1, 143.5, 137.3, 134.4, 130.9, 130.8, 127.7, 123.0, 122.8, 115.7, 111.1, 47.1, 42.4, 41.6, 39.1, 36.2, 32.4, 32.0; HRMS (ESI) for C$_{22}$H$_{25}$N$_3$O$_3$ [M+H]$^+$ calcd: 380.1974, found: 380.1973.

(E)-N-((E)-4-(1-(Furan-3-carbonyl)piperidin-4-yl)but-2-en-1-yl)-3-(pyridin-3-yl)acrylamide (FEI-84)

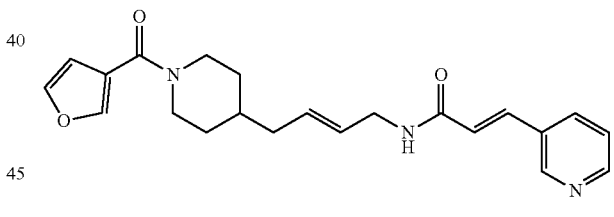

Ar$_1$COOH=furan-3-carboxylic acid. Yield: 44.3 mg (77.9%, MW=379.1896), white foam. $^1$H NMR (400 MHz, CDCl$_3$): δ=8.71-8.61 (m, 1H), 8.52-8.46 (m, 1H), 7.70 (d, 1H, J=7.6 Hz), 7.69 (s, 1H), 7.55 (d, 1H, J=15.7 Hz), 7.34 (s, 1H), 7.25-7.21 (m, 1H), 6.45 (s, 1H), 6.44 (d, 1H, J=15.7 Hz), 6.23-6.16 (m, 1H, N—H), 5.56 (dt, 1H, J=15.2 Hz, 6.8 Hz), 5.46 (dt, 1H, J=15.4 Hz, 5.7 Hz), 4.65-4.36 (m, 1H), 4.16-4.94 (m, 1H), 3.90 (t, 2H, J=5.1 Hz), 3.04-2.56 (m, 2H), 1.95 (t, 2H, J=6.4 Hz), 1.66 (d, 2H, J=12.0 Hz), 1.56-1.47 (m, 1H), 1.13-1.01 (m, 2H); $^{13}$C NMR (100 MHz, CDCl$_3$): δ=164.9, 163.7, 150.3, 149.1, 143.1, 142.6, 137.4, 134.4, 130.8, 130.7, 127.7, 123.7, 122.6, 121.3, 110.1, 47.5, 42.5, 41.6, 39.0, 36.2, 32.4, 31.7; HRMS (ESI) for C$_{22}$H$_{25}$N$_3$O$_3$ [M+H]$^+$ calcd: 380.1974, found: 380.1972.

(E)-3-(Pyridin-3-yl)-N-((E)-4-(1-(thiophene-2-carbonyl)piperidin-4-yl)but-2-en-1-yl)acrylamide (FEI-85)

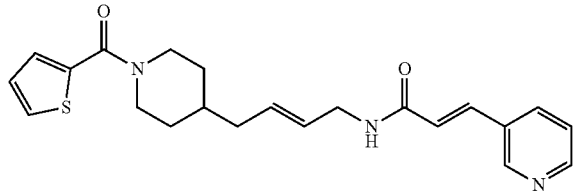 [SMILES: O=C(/C=C/c1cccnc1)NC/C=C/CC1CCN(C(=O)c2cccs2)CC1]

Ar₁COOH=thiophene-2-carboxylic acid. Yield: 44.6 mg (75.2%, MW=395.1667), white foam. ¹H NMR (400 MHz, CDCl₃): δ=8.68-8.62 (m, 1H), 8.48 (dd, 1H, J=4.6 Hz, 1.1 Hz), 7.68 (dt, 1H, J=7.9 Hz, 1.7 Hz), 7.54 (d, 1H, J=15.7 Hz), 7.35 (dd, 1H, J=5.0 Hz, 1.1 Hz), 7.21 (dd, 1H, J=7.9 Hz, 4.8 Hz), 7.18 (dd, 1H, J=3.6 Hz, 1.0 Hz), 6.95 (dd, 1H, J=5.0 Hz, 3.7 Hz), 6.47 (d, 1H, J=15.7 Hz), 6.40-6.35 (m, 1H, N—H), 5.55 (dt, 1H, J=15.2 Hz, 7.1 Hz), 5.45 (dt, 1H, J=15.5 Hz, 5.7 Hz), 4.45-4.22 (m, 2H), 3.89 (t, 2H, J=5.7 Hz), 2.91-2.74 (m, 2H), 1.95 (t, 2H, J=6.7 Hz), 1.67 (d, 2H, J=12.6 Hz), 1.58-1.48 (m, 1H), 1.17-1.06 (m, 2H); ¹³C NMR (100 MHz, CDCl₃): δ=164.9, 163.5, 150.3, 149.1, 137.4, 137.2, 134.4, 130.7, 130.6, 128.5, 128.3, 127.8, 126.6, 123.7, 123.0, 47.5, 42.5, 41.6, 39.0, 36.1, 32.4, 32.0; HRMS (ESI) for $C_{22}H_{25}N_3O_2S$ [M+H]⁺ calcd: 396.1746, found: 396.1746.

General Procedure for the Synthesis of FEI 154, FEI 155, FEI 158, FEI 159, FEI 162, FEI 164, FEI 166, FEI 167, FEI 168, FEI 170, FEI 171

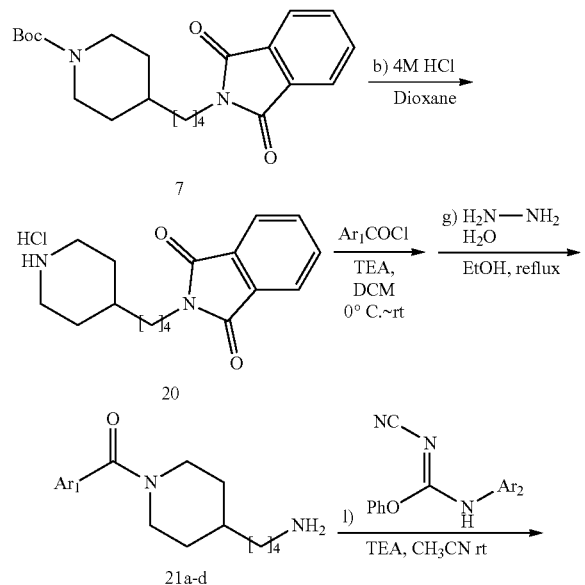

Ar₁ = Ph, 21a
    = Fur-2-yl, 21b
    = Thiophen-2-yl, 21c
    = 2,6-(CH₃O)₂C₆H₃, 21d
    = 4-(MeO)₂CH-2,6-(MeO)₂C₆H₂: 21e

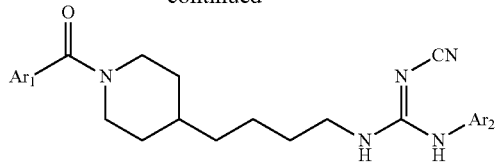

2-(4-(Piperidin-4-yl)butyl)isoindoline-1,3-dione hydrochloride (20)

Salt 20 was prepared from tert-butyl 4-(4-(1,3-dioxoisoindolin-2-yl)butyl)piperidine-1-carboxylate (7, 4.3 g, 11.1 mmol, MW=386.496) according to the same procedure as that used to prepare 9a from 9. (hydrolysis in HCl/dioxane). Yield: 3.4 g (94.5%, MW=323.838), white solid. ¹H NMR (400 MHz, CDCl₃): δ=7.90-7.84 (m, 2H), 7.77-7.72 (m, 2H), 3.70 (t, 2H, J=7.1 Hz), 3.59-3.36 (m, 2H), 3.04-2.74 (m, 2H), 1.99-1.83 (m, 2H), 1.71-1.56 (m, 6H), 1.42-1.33 (m, 3H).

(3-2a)(4-(4-Aminobutyl)piperidin-1-yl)(phenyl)methanone (21a)

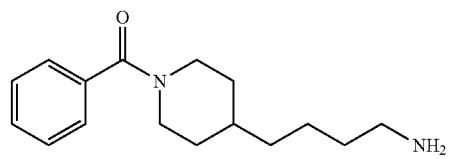 [SMILES: NCCCCC1CCN(C(=O)c2ccccc2)CC1]

A solution of piperidine salt 20 (0.65 g, 2.0 mmol) in CH₂Cl₂ (10 mL) was cooled to 0° C. Et₃N (0.9 mL, ca. 6 mmol) and benzoyl chloride (0.281 g, 2.0 mmol, Ar₁COCl) were added portion-wise in succession under stirring. at 0° C. The mixture was allowed to reach 20° C. and was stirred at this temperature for 3 h. A saturated aqueous solution of NaHCO₃ (30 mL) was added and the mixture stirred vigorously at 20° C. for 10 min. The aqueous layer was extracted with CH₂Cl₂ (20 mL, 3 times). The combined organic layers were washed with brine (50 mL) and dried (MgSO₄). Solvent evaporation in vacuo gave a crude benzamide that was added under N₂ atmosphere to a stirred solution of hydrazine hydrate (0.25 mL, ca. 5 mmol) in ethanol (10 mL) at 20° C. After stirring at 20° C. 10 min the mixture was heated under reflux for 2 h. After cooling to 20° C., the white precipitate was filtered off and washed with ethanol (15 mL). The ethanolic solutions were combined and the solvent evaporated in vacuo. The residue was taken in CH₂Cl₂ (20 mL) and a saturated aqueous solution of K₂CO₃ (20 mL). Vigorous stirring for 10 min gave two clear phases. The aqueous phase was extracted with CH₂Cl₂ (10 mL, 3 times). The combined organic phases were washed with brine (30 mL) and dried (MgSO₄). After solvent evaporation in vacuo the residue was purified by FC (80/18/2 MeOH/EtOAc/Et₃N). Yield (two steps): 0.48 g (92%, MW=260.382), yellow oil. ¹H NMR (400 MHz, CDCl₃): δ=7.44-7.37 (m, 5H), 4.80-4.66 (m, 1H), 3.83-3.68 (m, 1H), 2.98 (t, 1H, J=12.4 Hz), 2.83-2.66 (m, 3H), 1.90-1.78 (m, 1H), 1.69-1.51 (m, 4H), 1.42-1.25 (m, 4H), 1.23-1.05 (m, 2H).

(4-(4-Aminobutyl)piperidin-1-yl)(furan-2-yl)methanone (21b)

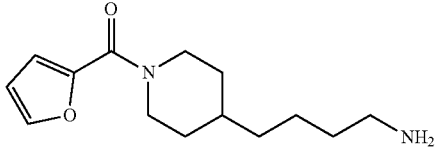 [SMILES: NCCCCC1CCN(C(=O)c2ccco2)CC1]

Amide 21b was prepared from amine 20 (0.65 g, 2.0 mmol) and 2-furoyl chloride (0.26 g, 2.0 mmol) according to the same procedure as that used to prepare 21a.

Yield: 0.43 g (86%, two steps), yellow oil. The spectral data for this compound are the same as those described for compound 41c further below.

(4-(4-Aminobutyl)piperidin-1-yl)(thiophen-2-yl)methanone (21c)

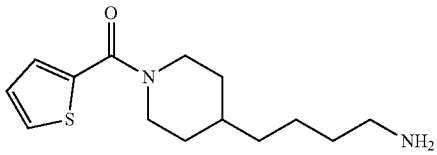

Amide 21c was prepared from amine 20 (0.65 g, 2.0 mmol) and thiophene-2-carbonyl chloride (0.29 g, 2.0 mmol) according to the same procedure as that used to prepare 21a.

Yield: 0.43 g (81%, two steps), yellow oil. The spectral data for this compound are the same as those described for compound 41b further below.

(3-2d)(4-(4-Aminobutyl)piperidin-1-yl)(2,6-dimethoxyphenyl)methanone (21d)

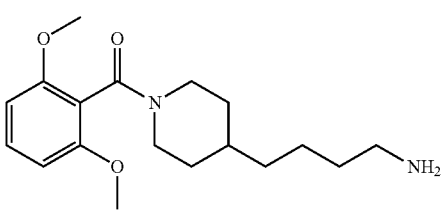 [SMILES: COc1cccc(OC)c1C(=O)N1CCC(CCCCN)CC1]

Amide 21d was prepared from amine 20 (0.64 g, 2.0 mmol) and 2,6-dimethoxybenzoyl chloride (0.4 g, 2.0 mmol) according to the same procedure as that used to prepare 21a.

Yield: 0.45 g (70.3%, two steps), yellow oil. The spectral data for this compound are the same as those described for compound 41d further below.

(E)-1-(4-(1-Benzoylpiperidin-4-yl)butyl)-2-cyano-3-(pyridin-4-yl)guanidine (FEI-154)

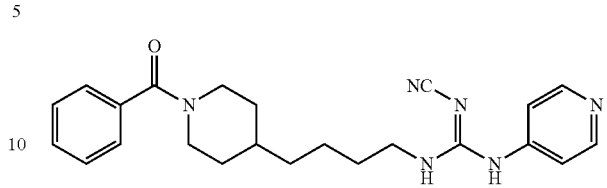

Step 1): A solution of amine 21a (48.0 mg, 0.15 mmol), phenyl (Z)—N'-cyano-N-(pyridin-3-yl)carbamimidate (35.7 mg, 0.15 mmol) and triethylamine (20.8 □L, 0.15 mmol) in acetonitrile (2 mL) was stirred at 20° C. for 36 h (monitored by TLC). After the end of the reaction, the volatiles were evaporated completely under reduced pressure. The residue was purified by FC (EtOAc/MeOH=5/1) to give 38.6 mg (55%) of FEI-154 as white foam. Yield: 37.5 mg (61.8%, MW=404.518), white foam. $^1$H NMR (400 MHz, CDCl$_3$): $\delta$=8.36-8.32 (m, 2H), 7.36-7.29 (m, 3H), 7.28-7.25 (m, 2H), 7.14-7.08 (m, 2H), 6.02 (t, 1H, J=5.2 Hz), 4.57 (d, 1H, J=8.3 Hz), 3.65 (d, 1H, J=10.6 Hz), 3.30 (q, 2H, J=6.2 Hz), 2.91 (t, 1H, J=11.4 Hz), 2.68 (t, 1H, J=11.4 Hz), 1.74-1.68 (m, 1H), 1.56-1.42 (m, 4H), 1.29-1.18 (m, 4H), 1.12-0.99 (m, 2H); $^{13}$C NMR (100 MHz, CDCl$_3$): $\delta$=170.5, 157.5, 150.2, 145.2, 136.0, 129.8, 128.6, 126.7, 116.9, 115.5, 48.2, 42.7, 42.5, 36.1, 35.9, 33.0, 31.8, 29.5, 23.7; HRMS (ESI) for $C_{23}H_{28}N_6O$ [M+H]$^+$ calcd: 405.2403, found: 405.2405.

(E)-2-Cyano-1-(4-(1-(2,6-dimethoxybenzoyl)piperidin-4-yl)butyl)-3-(pyridin-4-yl)guanidine (FEI-155)

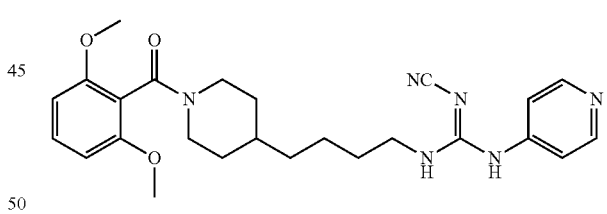

Obtained from amine 21d (48.0 mg, 0.15 mmol) and phenyl (Z)—N'-cyano-N-(pyridin-4-yl)carbamimidate (35.7 mg, 0.15 mmol) according to the same procedure as that used to prepare FEI-154. Yield: 39.8 mg (57%, MW=464.57), white foam. $^1$H NMR (400 MHz, CDCl$_3$): $\delta$=8.38-8.32 (m, 2H), 7.30 (t, 1H, J=8.5 Hz), 7.25-7.19 (m, 2H), 6.59 (dd, 2H, J=8.3 Hz, 6.5 Hz), 4.71 (d, 1H, J=13.0 Hz), 3.79 (s, 3H), 3.76 (s, 3H) 3.48-3.40 (m, 3H), 2.98 (dt, 1H, J=12.6 Hz, 2.0 Hz), 2.78 (dt, 1H, J=12.8 Hz, 2.7 Hz), 1.85 (d, 1H, J=12.8 Hz), 1.63-1.53 (m, 4H), 1.42-1.27 (m, 4H), 1.15 (qd, 2H, J=13.2 Hz, 3.3 Hz); $^{13}$C NMR (100 MHz, CDCl$_3$): $\delta$=165.6, 157.2, 156.4, 149.7, 145.9, 130.5, 116.6, 115.0, 114.0, 103.9, 55.7, 47.1, 42.5, 42.4, 41.8, 35.9, 32.8, 31.8, 29.5, 23.7; HRMS (ESI) for $C_{25}H_{32}N_6O_3$ [M+H]$^+$ calcd: 465.2614, found: 465.2608.

(E)-2-Cyano-1-(4-(1-(furan-2-carbonyl)piperidin-4-yl)butyl)-3-(pyridin-4-yl)guanidine (FEI-158)

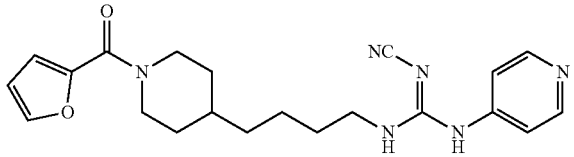

Obtained from amine 21b (37.5 mg, 0.15 mmol) and phenyl (Z)—N'-cyano-N-(pyridin-4-yl)carbamimidate (35.7 mg, 0.15 mmol) according to the same procedure as that used to prepare FEI-154. Yield: 37.7 mg (63.7%, MW=394.479), white foam. $^1$H NMR (400 MHz, CDCl$_3$): δ=8.57-8.47 (m, 2H), 7.52-7.48 (m, 1H), 7.28-7.24 (m, 2H), 6.96-6.90 (m, 1H), 6.53-6.47 (m, 1H), 5.91-5.81 (m, 1H), 4.62-4.40 (m, 2H), 3.48-3.38 (m, 2H), 3.15-2.67 (m, 2H), 1.83-1.75 (m, 2H), 1.67-1.52 (m, 3H), 1.44-1.28 (m, 4H), 1.25-1.13 (m, 2H); $^{13}$C NMR (100 MHz, CDCl$_3$): δ=159.3, 157.5, 157.4, 150.5, 147.7, 145.1, 143.8, 116.9, 115.8, 115.6, 111.2, 47.0, 42.5, 41.8, 36.0, 35.8, 32.7, 31.9, 29.5, 23.7; HRMS (ESI) for C$_{21}$H$_{26}$N$_6$O$_2$ [M+H]$^+$ calcd: 395.2195, found: 395.2189.

(E)-2-Cyano-1-(pyridin-4-yl)-3-(4-(1-(thiophene-2-carbonyl)piperidin-4-yl)butyl)guanidine (FEI-159)

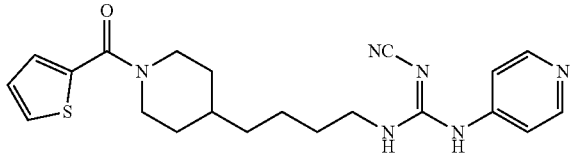 [SMILES: N#C/N=C(\NCCCCC1CCN(C(=O)c2ccco2)CC1)Nc1ccncc1]

Obtained from amine 21c (40 mg, 0.15 mmol) and phenyl (Z)—N'-cyano-N-(pyridin-4-yl)carbamimidate (35.7 mg, 0.15 mmol) according to the same procedure as that used to prepare FEI-154. Yield: 38.2 mg (62%, MW=410.54), white foam. $^1$H NMR (400 MHz, CDCl$_3$): δ=8.40-8.28 (m, 2H), 7.38 (d, 1H, J=5.1 Hz), 7.21 (s, 1H), 7.18 (d, 2H, J=3.2 Hz), 6.97 (dd, 1H, J=4.8 Hz, 3.8 Hz), 4.41-4.20 (m, 2H), 3.34 (t, 2H, J=7.1 Hz), 2.94-2.78 (m, 2H), 1.71-1.64 (m, 2H), 1.57-1.44 (m, 3H), 1.34-1.19 (m, 4H), 1.10 (qd, 2H, J=12.3 Hz, 3.5 Hz); $^{13}$C NMR (100 MHz, CDCl$_3$): δ=163.7, 157.2, 149.9, 145.7, 137.0, 128.7, 128.5, 126.8, 116.9, 115.3, 46.3, 42.5, 42.4, 36.0, 35.8, 32.7, 31.9, 29.4, 23.7; HRMS (ESI) for C$_{21}$H$_{26}$N$_6$OS [M+H]$^+$ calcd: 411.1967, found: 411.1962.

(E)-2-cyano-1-(4-(1-(4-(dimethoxymethyl)-2,6-dimethoxybenzoyl)piperidin-4-yl)butyl)-3-(pyridazin-4-yl)guanidine (FEI-162)

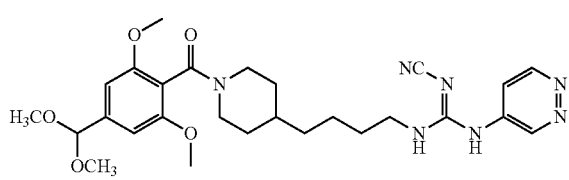 [SMILES: COc1cc(C(OC)OC)cc(OC)c1C(=O)N1CCC(CCCCN/C(=N\C#N)Nc2ccnnc2)CC1]

(4-(4-Aminobutyl)piperidin-1-yl)(4-dimethoxymethyl-2,6-dimethoxyphenyl)methanone (21e) was prepared from 4-(dimethoxymethyl)-2,6-dimethoxybenzoic acid (61.5 mg, 0.24 mmol) and piperidine salt 20 (81 mg, 0.25 mmol) according to the same procedure (2 steps) as that applied for the preparation of 21a. The crude primary amine so-obtained was then mixed with phenyl (Z)—N'-cyano-N-(pyridazin-4-yl)carbamimidate (47.8 mg, 0.2 mmol) and Et$_3$N (34 □L. 0.24 mmol) in acetonitrile (2 mL). The mixture was stirred at 20° C. for 48 h (monitoring by TLC). The solvent was evaporated in vacuo and the residue purified by FC (5/1 EtOAc/MeOH). Yield (3 steps): 37.4 mg (27.7%, MW=539.637), white foam. $^1$H NMR (400 MHz, CDCl$_3$): δ=8.89-8.68 (m, 2H), 7.91-7.71 (m, 1H), 7.0 (d, 1H, J=7.2 Hz), 6.58 (d, 2H, J=8.1 Hz), 5.21 (s, 1H), 4.67 (d, 1H, J=12.0 Hz), 3.85-3.77 (m, 2H), 3.71 (s, 3H), 3.70 (s, 3H), 3.40 (d, 1H, J=12.9 Hz), 3.26 (s, 6H), 2.92 (t, 1H, J=12.8 Hz), 2.74 (t, 1H, J=12.2 Hz), 1.78 (d, 1H, J=11.0 Hz), 1.61-1.41 (m, 4H), 1.40-1.04 (m, 6H); $^{13}$C NMR (100 MHz, CDCl$_3$): δ=165.9, 156.9, 156.3, 141.8, 138.3, 119.8, 115.9, 114.6, 113.4, 105.3, 102.8, 102.5, 56.2, 55.9, 53.2, 47.3, 42.7, 41.9, 35.9, 32.9, 31.7, 29.7, 23.6; HRMS (ESI) for C$_{27}$H$_{37}$N$_7$O$_5$ [M+H]$^+$ calcd: 539.2856, found: 539.2854.

(E)-2-Cyano-1-(4-(1-(furan-2-carbonyl)piperidin-4-yl)butyl)-3-(pyridazin-4-yl)guanidine (FEI-164)

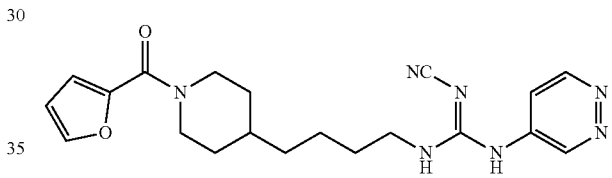

Obtained from amine 21b (37.5 mg, 0.15 mmol) and phenyl (Z)—N'-cyano-N-(pyridazin-4-yl)carbamimidate (35.9 mg, 0.15 mmol) according to the same procedure as that used to prepare FEI-162. Yield: 33.7 mg (56.8%, MW=395.467), white foam. $^1$H NMR (400 MHz, CDCl$_3$): δ=9.19-9.04 (m, 1H), 8.99-8.85 (m, 1H), 8.08-7.93 (m, 1H), 7.51-7.48 (m, 1H), 6.92 (d, 1H, J=3.4 Hz), 6.50 (dd, 1H, J=3.3 Hz, 1.7 Hz), 4.60-4.37 (m, 2H), 3.71-3.57 (m, 2H), 3.21-2.67 (m, 2H), 1.77 (d, 2H, J=12.2 Hz), 1.73-1.65 (m, 2H), 1.62-1.50 (m, 1H), 1.46-1.38 (m 2H), 1.36-1.29 (m 2H), 1.25-1.13 (m 2H); $^{13}$C NMR (100 MHz, CDCl$_3$): δ=159.3, 150.8, 147.5, 144.4, 143.9, 139.7, 129.7, 121.3, 115.8, 115.1, 111.3, 47.0, 43.6, 42.8, 36.0, 35.9, 32.6, 31.9, 29.7, 23.6; HRMS (ESI) for C$_2$H$_{25}$N$_7$O$_2$ [M+H]$^+$ calcd: 396.2148, found: 396.2142.

(E)-1-(4-(1-Benzoylpiperidin-4-yl)butyl)-2-cyano-3-(6-fluoropyridin-3-yl)guanidine (FEI-166)

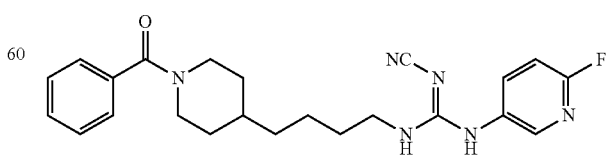

Obtained from amine 21a (40.0 mg, 0.15 mmol) and phenyl (Z)—N'-cyano-N-(6-fluoropyridin-3-yl)carbamimidate (38.4 mg, 0.15 mmol) according to the same procedure as that used to prepare FEI-162. Yield: 36.3 mg (57.3%, MW=422.508), white foam. $^1$H NMR (400 MHz, CDCl$_3$): δ=8.27-8.20 (m, 1H), 7.98 (s, 1H), 7.67 (t, 1H, J=6.5 Hz), 7.35-7.28 (m, 3H), 7.27-7.22 (m, 2H), 6.83 (dd, 1H, J=8.5 Hz, 2.7 Hz), 5.55 (brs, 1H, N—H), 4.63-4.50 (m, 1H), 3.64 (d, 1H, J=10.8 Hz), 3.21 (q, 2H, J=6.1 Hz), 2.89 (t, 1H, J=12.6 Hz), 2.66 (t, 1H, J=12.2 Hz), 1.77-1.68 (m, 1H), 1.61-1.50 (m, 1H), 1.58-1.39 (m, 3H), 1.28-1.14 (m, 4H), 1.13-0.95 (m, 2H); $^{13}$C NMR (100 MHz, CDCl$_3$): δ=170.4, 162.4 (J$_{C-F}$=239.8 Hz), 158.7, 143.7, 138.4, 136.1, 131.2, 129.7, 128.5, 126.7, 117.7, 110.3 (J$_{C-F}$=39.3 Hz), 48.1, 42.5, 42.2, 36.0, 35.9, 32.9, 31.8, 29.5, 23.7; HRMS (ESI) for C$_{23}$H$_{27}$FN$_6$O [M+H]$^+$ calcd: 423.2309, found: 423.2296.

(E)-2-Cyano-1-(4-(1-(2,6-dimethoxybenzoyl)piperidin-4-yl)butyl)-3-(6-fluoropyridin-3-yl)guanidine (FEI-167)

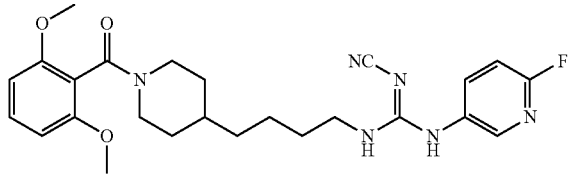 [SMILES: COc1cccc(OC)c1C(=O)N1CCC(CCCCN/C(=N\C#N)Nc2ccc(F)nc2)CC1]

Obtained from amine 21d (48.0 mg, 0.15 mmol) and phenyl (Z)—N'-cyano-N-(6-fluoropyridin-3-yl)carbamimidate (38.4 mg, 0.15 mmol) according to the same procedure as that used to prepare FEI-162. Yield: 38.5 mg (53.2%, MW=482.56), white foam. $^1$H NMR (400 MHz, CDCl$_3$): δ=8.44 (brs, 1H), 7.84 (s, 1H), 7.66 (td, 1H, J=6.5 Hz, 2.6 Hz), 7.16 (t, 1H, J=8.7 Hz), 6.74 (dd, 1H, J=8.6 Hz, 2.8 Hz), 6.43 (dd, 2H, J=11.2 Hz, 8.6 Hz), 5.65 (brs, 1H, N—H), 4.65 (d, 1H, J=13.1 Hz), 3.70 (s, 3H), 3.65 (s, 3H), 3.37 (d, 1H, J=13.1 Hz), 3.29 (q, 2H, J=6.2 Hz), 2.87 (t, 1H, J=11.2 Hz), 2.69 (t, 1H, J=12.4 Hz), 1.75 (d, 1H, J=12.4 Hz), 1.65-1.57 (m, 1H), 1.53-1.40 (m, 4H), 1.34-1.17 (m, 3H), 1.06 (qd, 2H, J=12.0 Hz, 3.5 Hz); $^{13}$C NMR (100 MHz, CDCl$_3$): δ=165.6, 161.8 (J$_{C-F}$=238.9 Hz), 158.4, 156.4, 142.7, 137.1, 131.7, 130.6, 117.5, 113.9, 109.5 (J$_{C-F}$=39.5 Hz), 103.9, 55.8, 47.1, 42.3, 41.8, 36.0, 35.9, 33.0, 31.7, 29.7, 23.8; HRMS (ESI) for C$_{25}$H$_{31}$FN$_6$O$_3$ [M+H]$^+$ calcd: 483.2520, found: 483.2515.

(E)-2-cyano-1-(4-(1-(4-(dimethoxymethyl)-2,6-dimethoxybenzoyl)piperidin-4-yl)butyl)-3-(6-fluoropyridin-3-yl)guanidine (FEI-168)

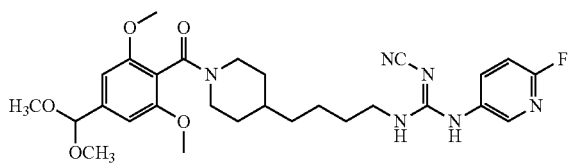 [SMILES: COc1cc(C(OC)OC)cc(OC)c1C(=O)N1CCC(CCCCN/C(=N\C#N)Nc2ccc(F)nc2)CC1]

Prepared from (4-(4-Aminobutyl)piperidin-1-yl)(4-dimethoxymethyl-2,6-dimethoxyphenyl)methanone (21e) and phenyl (Z)-phenyl N'-cyano-N-(6-fluoropyridin-3-yl)carbamimidate (51.2 mg, 0.2 mmol) according to the same procedure as that used to prepare FEI-162. Yield (3 steps): 38.9 mg (34.9%, MW=556.639), white foam. $^1$H NMR (400 MHz, CDCl$_3$): δ=8.39-8.29 (m, 1H), 7.89 (s, 1H), 7.68 (t, 1H, J=6.3 Hz), 6.76 (dd, 1H, J=8.3 Hz, 2.3 Hz), 6.56 (d, 2H, J=11.2 Hz), 5.54 (brs, 1H), 4.65 (d, 1H, J=12.7 Hz), 3.72 (s, 3H), 3.68 (s, 3H), 3.41-3.32 (m, 3H), 3.28 (s, 6H), 2.86 (t, 1H, J=12.0 Hz), 2.68 (t, 1H, J=12.6 Hz), 1.74 (d, 1H, J=12.6 Hz), 1.54-1.38 (m, 4H), 1.29-1.16 (m, 4H), 1.11-0.96 (m, 2H); $^{13}$C NMR (100 MHz, CDCl$_3$): δ=165.4, 162.0, 159.6, 158.4, 156.4, 142.9, 141.3, 137.3, 131.6, 114.0, 109.7, 102.0, 102.3, 55.9, 53.2, 47.0, 42.3, 41.8, 36.1, 35.9, 34.1, 32.9, 31.7, 29.7, 23.8, 22.4; HRMS (ESI) for C$_{28}$H$_{37}$FN$_6$O$_5$ [M+H]$^+$ calcd: 556.2809, found: 556.2813.

(E)-2-Cyano-1-(6-fluoropyridin-3-yl)-3-(4-(1-(furan-2-carbonyl)piperidin-4-yl)butyl)guanidine (FEI-170)

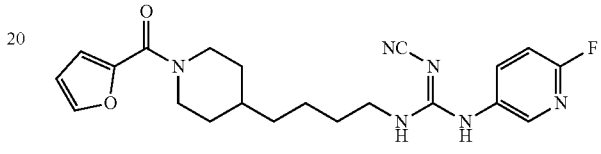

Obtained from amine 21b (37.5 mg, 0.15 mmol) and phenyl (Z)—N'-cyano-N-(6-fluoropyridin-3-yl)carbamimidate (38.4 mg, 0.15 mmol) according to the same procedure as that used to prepare FEI-162. Yield: 33.5 mg (54.1%, MW=412.469), white foam. $^1$H NMR (400 MHz, CDCl$_3$): δ=8.16 (brs, 1H), 7.81 (t, 1H, J=6.5 Hz), 7.68-7.61 (m, 1H), 7.49 (s, 1H), 7.03 (dd, 1H, J=8.6 Hz, 3.0 Hz), 6.93 (d, 1H, J=3.4 Hz), 6.49 (q, 1H, J=3.2 Hz), 5.10 (brs, 1H, N—H), 4.62-4.41 (m, 2H), 3.34 (q, 2H, J=6.2 Hz), 3.13-2.67 (m, 2H), 1.78 (d, 2H, J=12.7 Hz), 1.59-1.51 (m, 3H), 1.39-1.25 (m, 4H), 1.21 (qd, 2H, J=12.4 Hz, 3.3 Hz); $^{13}$C NMR (100 MHz, CDCl$_3$): δ=159.2, 158.7, 147.8, 146.2, 144.2, 143.2, 142.6, 138.5, 131.0, 115.7, 111.2, 110.5, 46.8, 42.4, 42.2, 36.0, 35.9, 32.7, 32.1, 29.5, 23.7; HRMS (ESI) for C$_{21}$H$_{25}$FN$_6$O$_2$ [M+H]$^+$ calcd: 413.2101, found: 413.2094.

(E)-2-Cyano-1-(6-fluoropyridin-3-yl)-3-(4-(1-(thiophene-2-carbonyl)piperidin-4-yl)butyl)guanidine (FEI-171)

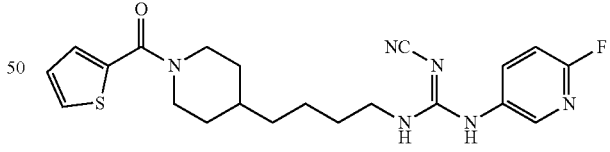

Obtained from amine 21c (40.0 mg, 0.15 mmol) and phenyl (Z)—N'-cyano-N-(6-fluoropyridin-3-yl)carbamimidate (38.4 mg, 0.15 mmol) according to the same procedure as that used to prepare FEI-162. Yield: 36.9 mg (57.4%, MW=428.53), white foam. $^1$H NMR (400 MHz, CDCl$_3$): δ=8.01 (s, 1H), 7.75 (t, 1H, J=5.6 Hz), 7.37 (dd, 1H, J=5.0 Hz, 0.9 Hz), 7.19 (dd, 1H, J=3.5 Hz, 0.8 Hz), 6.97 (dd, 1H, J=4.9 Hz, 3.7 Hz), 6.90 (dd, 1H, J=8.7 Hz, 3.0 Hz), 4.42-4.16 (m, 2H), 3.23 (t, 2H, J=7.2 Hz), 2.96-2.71 (m, 2H), 1.68 (d, 2H, J=12.0 Hz), 1.54-1.41 (m, 3H), 1.32-1.19 (m, 4H), 1.11 (qd, 2H, J=12.3 Hz, 3.6 Hz); $^{13}$C NMR (100 MHz, CDCl$_3$): δ=163.7, 162.4 (J$_{C-F}$=240.0 Hz), 158.6, 158.4, 143.5, 138.4, 138.0, 137.0, 128.6, 126.7, 117.6, 110.3

($J_{C-F}$=40.0 Hz), 46.3, 42.2, 42.0, 36.0, 35.9, 32.8, 31.7, 29.4, 23.7; HRMS (ESI) for $C_{21}H_{25}FN_6OS$ [M+H]$^+$ calcd: 429.1873, found: 429.1872.

General Procedure for the Synthesis of FEI 186-188, FEI 190-201

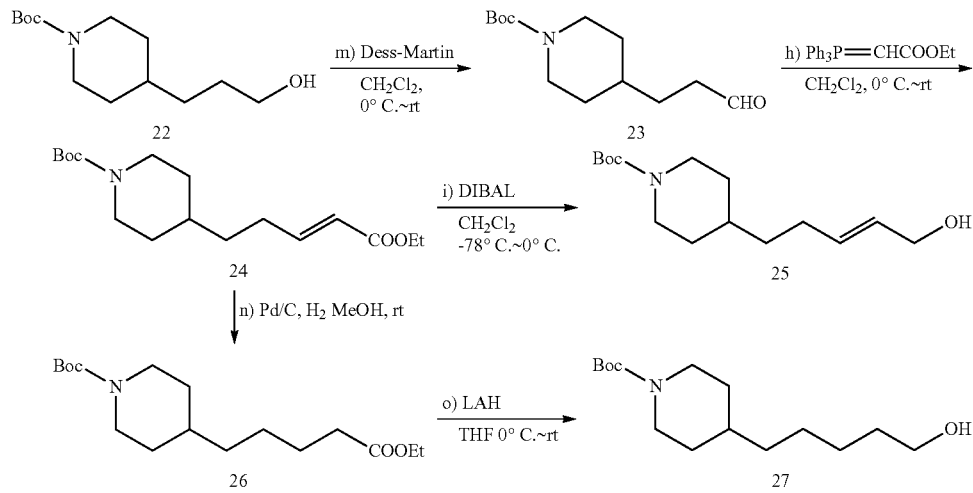

tert-Butyl 4-(3-oxopropyl)piperidine-1-carboxylate (23)

A solution of tert-butyl 4-(3-hydroxypropyl)piperidine-1-carboxylate (22, 1.00 g, 4.11 mmol) in $CH_2Cl_2$ (20 mL) was cooled to 0° C. Under stirring 1,1,1-triacetoxy-1,1-dihydro-1,2-benziodoxol-3(1H)-one (Dess-Martin Reagent, 2.27 g, 5.34 mmol) was added portion-wise, then the mixture was stirred at 20° C. for 4 h. After filtration, the filtrate was washed with a saturated aqueous solution of $NaHCO_3$ (20 mL), and then further washed with brine (20 mL) and dried ($MgSO_4$). The solvent was evaporated in vacuo, and the resulting residue was purified by FC (8/1 PE/EtOAc) to give 0.85 g (86%) of 23, colorless oil, that was used directly in the next step.

tert-Butyl(E)-4-(5-ethoxy-5-oxopent-3-en-1-yl)piperidine-1-carboxylate (24)

Compound 24 was prepared from 23 (0.7 g, 2.9 mmol) and (carbethoxymethylene)triphenylphosphorane (1.21 g, 3.5 mmol) according to the same procedure as that used to prepare 11.

Yield: 0.83 g (92.2%), colorless oil. $^1$H NMR (400 MHz, CDCl$_3$): δ=6.97 (dt, 1H, J=15.7 Hz, 6.8 Hz), 5.84 (dt, 1H, J=15.6 Hz, 1.4 Hz), 4.21 (q, 2H, J=7.3 Hz), 4.16-4.03 (m, 2H), 2.68 (t, 2H, J=10.9 Hz), 2.25 (q, 2H, J=6.8 Hz), 1.71-1.63 (m, 2H), 1.47 (s, 9H), 1.46-1.37 (m, 3H), 1.31 (t, 3H, J=7.1 Hz), 1.11 (qd, 2H, J=10.7 Hz, 4.0 Hz).

tert-Butyl (E)-4-(5-hydroxypent-3-en-1-yl)piperidine-1-carboxylate (25)

Compound 25 was prepared from 24 (0.74 g, 2.38 mmol) according to the same procedure as that used to prepare compound 12.

Yield: 0.56 g (87.5%), colorless oil. $^1$H NMR (400 MHz, CDCl$_3$): δ=5.76-5.62 (m, 2H), 4.12 (t, 2H, J=5.3 Hz), 4.09-3.99 (m, 1H, O-H), 2.69 (t, 2H, J=13.0 Hz), 2.10 (dd, 2H, J=14.1 Hz, 6.6 Hz), 1.75-1.62 (m, 2H), 1.47 (s, 9H), 1.45-1.30 (m, 4H), 1.31-1.25 (m, 1H), 1.10 (qd, 2H, J=11.8 Hz, 3.9 Hz).

tert-Butyl 4-(5-ethoxy-5-oxopentyl)piperidine-1-carboxylate (26)

Compound 24 (0.6 g, 1.93 mmol) was dissolved in methanol (5 mL), then Pd/C (21.3 mg, 0.2 mol) was added. The reaction mixture stirred under $H_2$ atmosphere at 20° C. overnight. The suspension was filtered on a Cellite bed and the cake was washed with MeOH (15 mL). After evaporation of the solvent in vacuo, 0.54 g (89.4%) of 26 was obtained as yellow oil, which was used directly in the next step without further purification.

$^1$H NMR (400 MHz, CDCl$_3$): δ=4.15 (q, 2H, J=7.0 Hz), 4.12-4.02 (m, 2H), 2.68 (t, 2H, J=12.5 Hz), 2.32 (t, 2H, J=7.6 Hz), 1.71-1.55 (m, 6H), 1.47 (s, 9H), 1.42-1.32 (m, 3H), 1.27 (t, 3H, J=6.3 Hz), 1.08 (qd, 2H, J=11.9 Hz, 4.1 Hz).

tert-Butyl 4-(5-hydroxypentyl)piperidine-1-carboxylate (27)

To a solution of compound 26 (0.54 g, 1.72 mmol) in THF (5 mL) was added lithium aluminium hydride (0.2 g, 5.16 mmol) in small portions at 0° C. and under stirring. Then the mixture was stirred at 20° C. overnight (monitored by TLC). After the end of the reaction, the mixture was cooled to 0° C., and 30% aqueous KOH (5 mL) was added slowly under vigorous stirring. After further stirring at 20° C. for 1 h, the suspension was filtered on a Cellite bed and the cake was washed with THF (15 mL). Evaporation of the solvent in vacuo; the crude was purified by FC (3/1 PE/EtOAc) to give 0.37 g (78.7%) of 27 as yellow oil.

$^1$H NMR (400 MHz, CDCl$_3$): δ=4.18-3.95 (m, 2H), 2.81-2.59 (m, 4H), 1.70-1.62 (m, 2H), 1.47 (s, 9H), 1.38-1.29 (m, 6H), 1.30-1.21 (m, 3H), 1.08 (qd, 2H, J=12.1 Hz, 4.0 Hz).

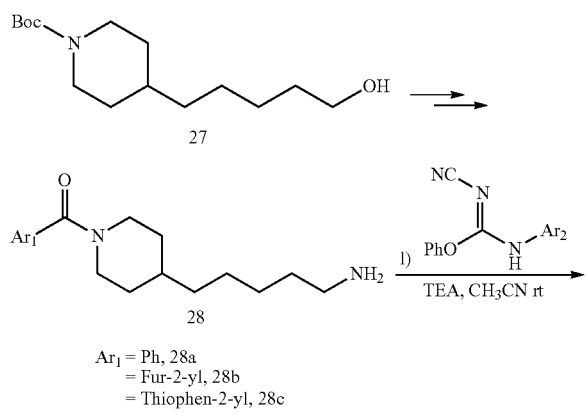

27

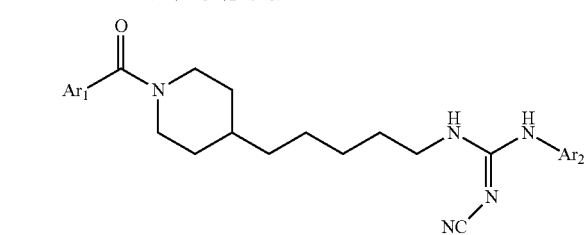

28

Ar₁ = Ph, 28a
= Fur-2-yl, 28b
= Thiophen-2-yl, 28c
= 2,6-(CH₃O)₂C₆H₃, 28d

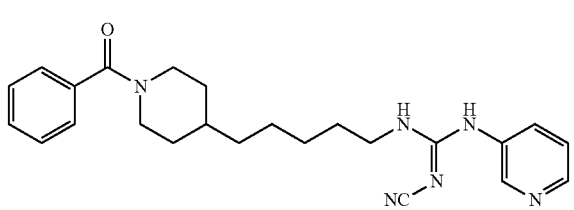 [SMILES: N#C/N=C(\NCCCCCC1CCN(C(=O)c2ccccc2)CC1)Nc1cccnc1]

Compound 28a-d were prepared from 27 (0.27 g, 1.0 mmol) following the same procedure as that used to prepare 21a-d. The crude 21a-d were used directly in the next step. Yield: 45~55% (4 steps).

(E)-1-(5-(1-Benzoylpiperidin-4-yl)pentyl)-2-cyano-3-(pyridin-3-yl)guanidine (FEI-186)

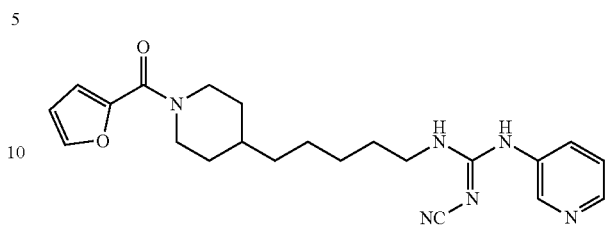

Obtained from amine 28a (41.2 mg, 0.15 mmol) and phenyl (Z)—N'-cyano-N-(pyridin-3-yl)carbamimidate (35.7 mg, 0.15 mmol) according to the same procedure as that used to prepare FEI-154. Yield: 34.2 mg (54.5%, MW=405.2052), white foam. $^1$H NMR (400 MHz, CDCl₃): δ=8.64-8.42 (m, 2H), 8.11-8.01 (m, 1H), 7.69 (d, 1H, J=7.7 Hz), 7.44-7.34 (m, 5H), 5.33 (brs, 1H, N—H), 4.69 (d, 1H, J=11.8 Hz), 3.74 (d, 1H, J=11.4 Hz), 3.31 (q, 2H, J=6.4 Hz), 2.98 (t, 1H, J=12.4 Hz), 2.76 (t, 1H, J=12.8 Hz), 1.85-1.71 (m, 2H), 1.67-1.46 (m, 4H), 1.37-1.24 (m, 5H), 1.20-1.05 (m, 2H); $^{13}$C NMR (100 MHz, CDCl₃): δ=170.3, 158.5, 147.1, 145.8, 136.2, 133.4, 132.2, 129.6, 128.5, 126.7, 124.0, 117.6, 48.2, 42.6, 42.3, 36.2, 36.0, 33.0, 32.0, 29.3, 26.8, 26.2; HRMS (ESI) for C₂₄H₃₀N₆O [M+H]⁺ calcd: 419.2559, found: 419.2554.

(E)-2-Cyano-1-(5-(1-(furan-2-carbonyl)piperidin-4-yl)pentyl)-3-(pyridin-3-yl)guanidine (FEI-187)

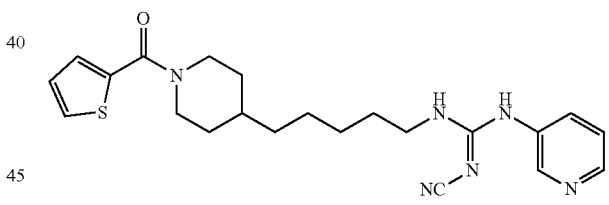

Obtained from amine 28b (39.6 mg, 0.15 mmol) and phenyl (Z)—N'-cyano-N-(pyridin-3-yl)carbamimidate (35.7 mg, 0.15 mmol) according to the same procedure as that used to prepare FEI-154. Yield: 32.6 mg (53.2%), white foam. $^1$H NMR (400 MHz, CDCl₃): δ=8.66-8.40 (m, 2H), 8.22-8.09 (m, 1H), 7.71 (d, 1H, J=7.2 Hz), 7.49-7.47 (m, 1H), 7.37 (brs, 1H, N—H), 6.94-6.90 (m, 1H), 6.49-6.46 (m, 1H), 5.42 (brs, 1H, N—H), 4.61-4.36 (m, 2H), 3.33 (q, 2H, J=6.5 Hz), 3.15-2.68 (m, 2H), 1.82-1.72 (m, 2H), 1.62-1.50 (m, 3H), 1.37-1.25 (m, 6H), 1.23-1.13 (m, 2H); $^{13}$C NMR (100 MHz, CDCl₃): δ=159.2, 158.5, 147.9, 147.2, 145.8, 143.6, 133.4, 132.2, 124.2, 117.7, 115.6, 111.2, 47.0, 43.4, 42.2, 36.2, 36.0, 33.0, 32.1, 29.3, 26.9, 26.2; HRMS (ESI) for C₂₂H₂₈N₆O₂ [M+H]⁺ calcd: 409.2352, found: 409.2348.

(E)-2-Cyano-1-(pyridin-3-yl)-3-(5-(1-(thiophene-2-carbonyl)piperidin-4-yl)pentyl)guanidine (FEI-188)

Obtained from amine 28c (42.2 mg, 0.15 mmol) and phenyl (Z)—N'-cyano-N-(pyridin-3-yl)carbamimidate (35.7 mg, 0.15 mmol) according to the same procedure as that used to prepare FEI-154. Yield: 33.5 mg (52.6%), white foam. $^1$H NMR (400 MHz, CDCl₃): δ=8.65-8.39 (m, 2H), 8.14-8.01 (m, 1H), 7.70 (d, 1H, J=6.6 Hz), 7.44 (d, 1H, J=4.9 Hz), 7.37 (brs, 1H, N—H), 7.27 (d, 1H, J=3.3 Hz), 7.05 (t, 1H, J=4.0 Hz), 5.37 (brs, 1H, N—H), 4.54-4.27 (m, 2H), 3.33 (q, 2H, J=6.2 Hz), 3.03-2.82 (m, 2H), 1.82-1.71 (m, 2H), 1.60-1.50 (m, 3H), 1.37-1.24 (m, 6H), 1.19 (qd, 2H, J=12.3 Hz, 3.4 Hz); $^{13}$C NMR (100 MHz, CDCl₃): δ=163.5, 158.5, 147.1, 145.8, 137.3, 133.4, 132.2, 128.5, 128.3, 126.7, 124.2, 117.7, 47.1, 44.6, 42.2, 36.2, 36.0, 33.0, 32.1, 29.3, 26.9, 26.2; HRMS (ESI) for C₂₂H₂₈N₆OS [M+H]⁺ calcd: 425.2123, found: 425.2126

(E)-1-(5-(1-Benzoylpiperidin-4-yl)pentyl)-2-cyano-3-(pyridin-4-yl)guanidine (FEI-190)

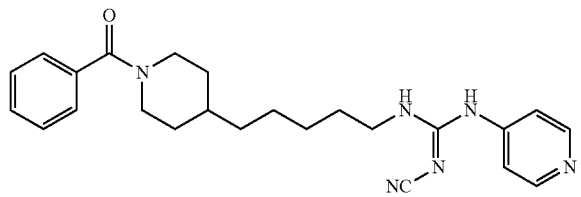 [SMILES: N#C/N=C(\NCCCCCC1CCN(C(=O)c2ccccc2)CC1)Nc1ccncc1]

Obtained from amine 28a (41.2 mg, 0.15 mmol) and phenyl (Z)—N'-cyano-N-(pyridin-4-yl)carbamimidate (35.7 mg, 0.15 mmol) according to the same procedure as that used to prepare FEI-154. Yield: 35.4 mg (56.4%), white foam. $^1$H NMR (400 MHz, CDCl$_3$): δ=8.42-8.21 (m, 2H), 7.37-7.30 (m, 3H), 7.29-7.26 (m, 2H), 7.16-7.04 (m, 2H), 5.97 (m, 1H, N—H), 4.58 (d, 1H, J=12.4 Hz), 3.66 (d, 1H, J=12.4 Hz), 3.31 (q, 2H, J=6.4 Hz), 2.92 (t, 1H, J=12.8 Hz), 2.68 (t, 1H, J=12.6 Hz), 1.78-1.69 (m, 1H), 1.58-1.42 (m, 4H), 1.28-1.17 (m, 6H), 1.14-0.98 (m, 2H); $^{13}$C NMR (100 MHz, CDCl$_3$): δ=170.5, 157.4, 150.6, 144.9, 136.1, 129.7, 128.6, 126.7, 116.8, 115.5, 48.2, 42.7, 42.5, 36.2, 36.0, 33.0, 32.0, 29.3, 26.9, 26.2; HRMS (ESI) for C$_{24}$H$_{30}$N$_6$O [M+H]$^+$ calcd: 419.2559, found: 419.2556.

(E)-2-Cyano-1-(5-(1-(furan-2-carbonyl)piperidin-4-yl)pentyl)-3-(pyridin-4-yl)guanidine (FEI-191)

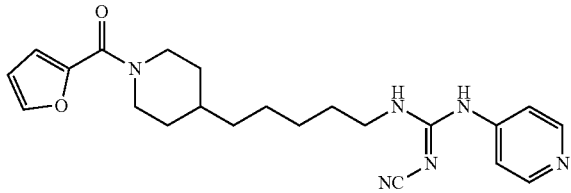 [SMILES: N#C/N=C(\NCCCCCC1CCN(C(=O)c2ccco2)CC1)Nc1ccncc1]

Obtained from amine 28b (39.6 mg, 0.15 mmol) and phenyl (Z)—N'-cyano-N-(pyridin-4-yl)carbamimidate (35.7 mg, 0.15 mmol) according to the same procedure as that used to prepare FEI-154. Yield: 34.5 mg (56.3%), white foam. $^1$H NMR (400 MHz, CDCl$_3$): δ=8.47-8.23 (m, 2H), 7.42-7.37 (m, 1H), 7.22-7.12 (m, 2H), 6.81 (d, 1H, J=3.4 Hz), 6.40 (q, 1H, J=1.8 Hz), 6.10-6.05 (m, 1H, N—H), 4.52-4.27 (m, 2H), 3.34 (q, 2H, J=6.7 Hz), 3.12-2.54 (m, 2H), 1.74-1.65 (m, 2H), 1.56-1.42 (m, 3H), 1.30-1.16 (m, 6H), 1.09 (qd, 2H, J=12.8 Hz, 2.4 Hz); $^{13}$C NMR (100 MHz, CDCl$_3$): δ=159.3, 157.5, 150.5, 147.7, 145.2, 143.8, 117.0, 115.7, 115.6, 111.3, 47.2, 43.4, 42.6, 36.2, 36.0, 32.8, 32.3, 29.3, 26.9, 26.2; HRMS (ESI) for C$_{22}$H$_{28}$N$_6$O$_2$ [M+H]$^+$ calcd: 409.2352, found: 409.2348.

(E)-2-Cyano-1-(pyridin-4-yl)-3-(5-(1-(thiophene-2-carbonyl)piperidin-4-yl)pentyl)guanidine (FEI-192)

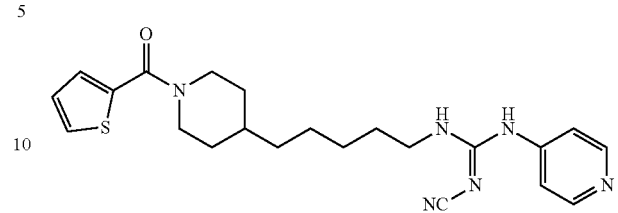

Obtained from amine 28c (42.2 mg, 0.15 mmol) and phenyl (Z)—N'-cyano-N-(pyridin-4-yl)carbamimidate (35.7 mg, 0.15 mmol) according to the same procedure as that used to prepare FEI-150. Yield: 35.8 mg (56.3%), white foam. $^1$H NMR (400 MHz, CDCl$_3$): δ=8.60-8.31 (m, 2H), 7.44 (dd, 1H, J=11.5 Hz, 5.2 Hz), 7.30-7.18 (m, 3H), 7.07-7.01 (m, 1H), 6.09-5.99 (m, 1H, N—H), 4.50-4.27 (m, 2H), 3.39 (q, 2H, J=5.8 Hz), 3.02-2.82 (m, 2H), 1.80-1.70 (m, 2H), 1.64-1.49 (m, 3H), 1.38-1.24 (m, 6H), 1.16 (qd, 2H, J=11.8 Hz, 3.5 Hz); $^{13}$C NMR (100 MHz, CDCl$_3$): δ=163.5, 157.5, 150.6, 145.0, 137.1, 128.6, 128.4, 126.8, 116.8, 115.6, 47.7, 42.7, 42.5, 36.2, 36.0, 32.7, 32.3, 29.2, 26.8, 26.2; HRMS (ESI) for C$_{22}$H$_{28}$N$_6$OS [M+H]$^+$ calcd: 425.2123, found: 425.2127.

(E)-2-Cyano-1-(5-(1-(2,6-dimethoxybenzoyl)piperidin-4-yl)pentyl)-3-(pyridin-4-yl)guanidine (FEI-193)

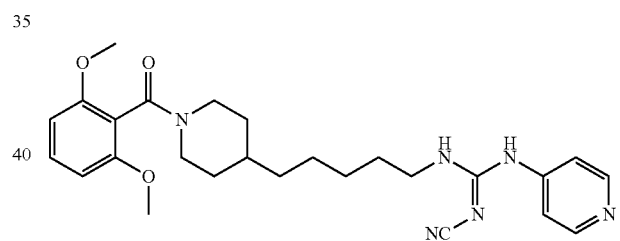

Obtained from amine 28d (50.1 mg, 0.15 mmol) and phenyl (Z)—N'-cyano-N-(pyridin-4-yl)carbamimidate (35.7 mg, 0.15 mmol) according to the same procedure as that used to prepare FEI-154. Yield: 38.7 mg (54%), white foam. $^1$H NMR (400 MHz, CDCl$_3$): δ=8.41-8.05 (m, 2H), 7.22-7.18 (m, 1H), 7.12-6.94 (m, 2H), 6.46 (d, 2H, J=8.3 Hz), 6.18 (brs, 1H, N—H), 4.65 (d, 1H, J=13.2 Hz), 3.69 (s, 3H), 3.67 (s, 3H), 3.48-3.35 (m, 3H), 2.91 (t, 1H, J=12.8 Hz), 2.72 (t, 1H, J=12.5 Hz), 1.81-1.71 (m, 1H), 1.57-1.38 (m, 4H), 1.33-1.18 (m, 6H), 1.14-1.02 (m, 2H); $^{13}$C NMR (100 MHz, CDCl$_3$): δ=165.8, 157.0, 156.3, 150.0, 145.4, 130.8, 116.8, 114.7, 113.8, 104.0, 55.8, 47.2, 42.7, 42.0, 36.4, 36.2, 33.0, 32.0, 29.6, 27.0, 26.5; HRMS (ESI) for C$_{26}$H$_{34}$N$_6$O$_3$ [M+H]$^+$ calcd: 479.2771, found: 479.2768.

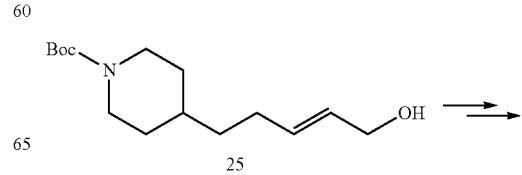

-continued

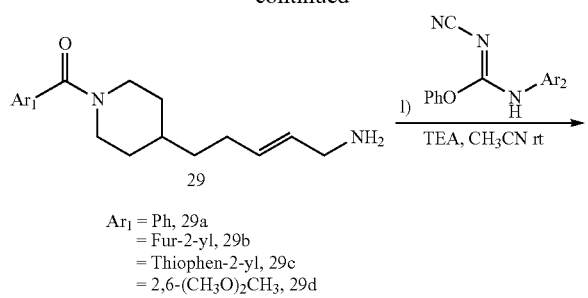

Ar₁ = Ph, 29a
= Fur-2-yl, 29b
= Thiophen-2-yl, 29c
= 2,6-(CH₃O)₂CH₃, 29d

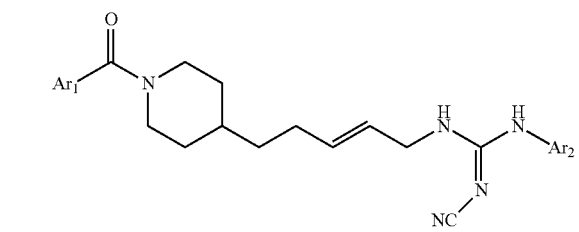

Compound 29a-d were prepared from 25 (0.53 g, 1.97 mmol) following the same procedure as that used to prepare 21, and used directly in the next step. Yield: 45-55% (4 steps).

(E)-1-((E)-5-(1-Benzoylpiperidin-4-yl)pent-2-en-1-yl)-2-cyano-3-(pyridin-3-yl)guanidine (FEI-194)

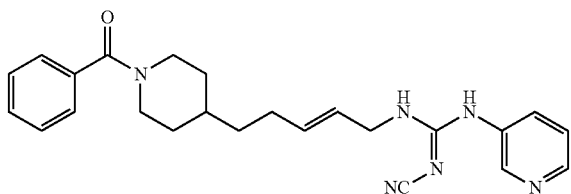 [SMILES: N#C/N=C(\NC/C=C/CCC1CCN(C(=O)c2ccccc2)CC1)Nc1cccnc1]

Obtained from amine 29a (54.4 mg, 0.2 mmol) and phenyl (Z)—N'-cyano-N-(pyridin-3-yl)carbamimidate (47.6 mg, 0.2 mmol) according to the same procedure as that used to prepare FEI-154. Yield: 42.5 mg (51%, MW=416,2325), white foam. $^1$H NMR (400 MHz, CDCl₃): δ=8.53-8.45 (m, 2H), 8.41-8.37 (m, 1H, N—H), 7.72 (d, 1H, J=7.8 Hz), 7.43-7.34 (m, 6H), 5.92-5.76 (m, 1H, N—H), 5.66 (dt, 1H, J=15.3 Hz, 6.2 Hz), 5.46 (dt, 1H, J=15.3 Hz, 6.0 Hz), 4.67 (d, 1H, J=11.2 Hz), 3.89 (t, 2H, J=5.5 Hz), 3.73 (d, 1H, J=11.6 Hz). 2.98 (t, 1H, J=12.8 Hz), 2.75 (t, 1H, J=12.9 Hz), 1.86-1.74 (m, 1H), 1.68-1.59 (m, 1H), 1.58-1.48 (m, 2H), 1.40-1.32 (m, 3H), 1.24-1.07 (m, 2H); $^{13}$C NMR (100 MHz, CDCl₃): δ=170.3, 158.5, 147.0, 145.5, 136.2, 124.6, 133.4, 131.9, 129.6, 128.5, 126.7, 124.8, 124.1, 117.6, 48.1, 44.1, 42.5, 35.6 (2C), 32.8, 31.8, 29.2; HRMS (ESI) for C₂₄H₂₈N₆O [M+H]⁺ calcd: 417.2403, found: 417.2401.

(E)-2-Cyano-1-((E)-5-(1-(furan-2-carbonyl)piperidin-4-yl)pent-2-en-1-yl)-3-(pyridin-3-yl)guanidine (FEI-195)

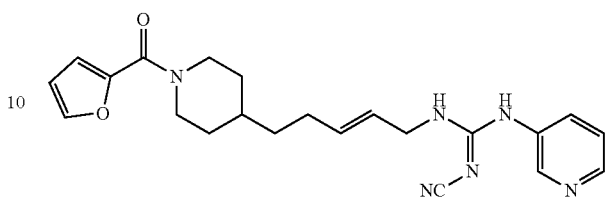

Obtained from amine 29b (52.4 mg, 0.2 mmol) and phenyl (Z)—N'-cyano-N-(pyridin-3-yl)carbamimidate (47.6 mg, 0.2 mmol) according to the same procedure as that used to prepare FEI-154. Yield: 43.4 mg (53.4%, MW=406.2117), white foam. $^1$H NMR (400 MHz, CDCl₃): δ=8.58-8.31 (m, 2H), 8.27-8.09 (m, 1H, N—H), 7.65 (d, 1H, J=8.1 Hz), 7.41-7.38 (m, 1H), 7.28-7.22 (m, 1H), 6.83 (d, 1H, J=3.5 Hz), 6.39 (dd, 1H, J=3.5 Hz, 1.8 Hz), 5.81-5.67 (m, 1H, N—H), 5.59 (dt, 1H, J=15.3 Hz, 6.4 Hz), 5.40 (dt, 1H, J=15.4 Hz, 6.0 Hz), 4.49-4.29 (m, 2H), 3.83 (t, 2H, J=5.6 Hz), 3.10-2.56 (m, 2H), 1.73-1.64 (m, 2H), 1.52-1.41 (m, 2H), 1.31-1.22 (m, 3H), 1.11 (qd, 2H, J=12.0 Hz, 3.7 Hz); $^{13}$C NMR (100 MHz, CDCl₃): δ=159.2, 158.5, 147.9, 147.2, 145.7, 143.6, 134.7, 133.4, 132.1, 124.8, 124.1, 117.5, 115.7, 111.2, 46.8, 44.1, 42.3, 35.6, 35.4, 32.7, 32.0, 29.2; HRMS (ESI) for C₂₂H₂₆N₆O₂ [M+H]⁺ calcd: 407.2195, found: 407.2193.

(E)-2-Cyano-1-(pyridin-3-yl)-3-((E)-5-(1-(thiophene-2-carbonyl)piperidin-4-yl)pent-2-en-1-yl)guanidine (FEI-196)

Obtained from amine 29c (55.6 mg, 0.2 mmol) and phenyl (Z)—N'-cyano-N-(pyridin-3-yl)carbamimidate (47.6 mg, 0.2 mmol) according to the same procedure as that used to prepare FEI-154. Yield: 43.7 mg (51.8%, MW=422.1889), white foam. $^1$H NMR (400 MHz, CDCl₃): δ=8.49-8.30 (m, 2H), 8.20-8.00 (m, 1H, N—H), 7.64 (d, 1H, J=7.8 Hz), 7.35 (dd, 1H, J=5.0 Hz, 0.9 Hz), 7.28-7.22 (m, 1H), 7.17 (dd, 1H, J=3.6 Hz, 1.0 Hz), 6.96 (dd, 1H, J=5.0 Hz, 3.6 Hz), 5.77-5.62 (m, 1H, N—H), 5.60 (dt, 1H, J=15.4 Hz, 6.3 Hz), 5.40 (dt, 1H, J=15.4 Hz, 5.8 Hz), 4.43-4.20 (m, 2H), 3.82 (t, 2H, J=5.6 Hz), 2.93-2.73 (m, 2H), 1.72-1.63 (m, 2H), 1.53-1.42 (m, 2H), 1.32-1.24 (m, 3H), 1.11 (qd, 2H, J=12.2 Hz, 3.9 Hz); $^{13}$C NMR (100 MHz, CDCl₃): δ=163.5, 158.5, 147.3, 145.6, 137.3, 134.7, 133.3, 132.1, 128.5, 128.3, 126.7, 124.8, 124.1, 117.5, 46.6, 44.8, 44.1, 35.6, 35.5, 32.5, 32.2, 29.2; HRMS (ESI) for C₂₂H₂₆N₆OS [M+H]⁺ calcd: 423.1967, found: 423.1972.

(E)-2-Cyano-1-((E)-5-(1-(2,6-dimethoxybenzoyl)piperidin-4-yl)pent-2-en-1-yl)-3-(pyridin-3-yl)guanidine (FEI-197)

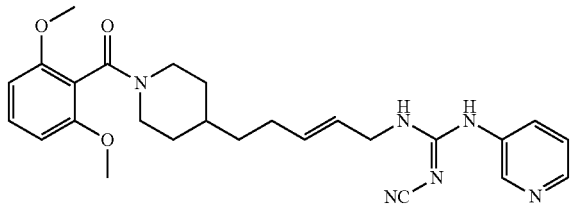 [SMILES: COc1cccc(OC)c1C(=O)N1CCC(CC/C=C/CN/C(=N\C#N)Nc2cccnc2)CC1]

Obtained from amine 29d (66.4 mg, 0.2 mmol) and phenyl (Z)—N'-cyano-N-(pyridin-3-yl)carbamimidate (47.6 mg, 0.2 mmol) according to the same procedure as that used to prepare FEI-154. Yield: 44.6 mg (46.8%, MW=476.2536), white foam. $^1$H NMR (400 MHz, CDCl$_3$): δ=8.37-8.25 (m, 2H), 8.20-8.13 (m, 1H, N—H), 7.64 (d, 1H, J=8.4 Hz), 7.19-7.13 (m, 1H), 7.17 (t, 1H, J=8.8 Hz), 6.46 (dd, 2H, J=8.4 Hz, 3.4 Hz), 5.69-5.63 (m, 1H, N—H), 5.61 (dt, 1H, J=15.4 Hz, 7.0 Hz), 5.39 (dt, 1H, J=15.4 Hz, 6.0 Hz), 4.66 (d, 1H, J=12.7 Hz), 3.85 (t, 2H, J=5.4 Hz), 3.70 (s, 3H), 3.68 (s, 3H), 3.38 (d, 1H, J=13.3 Hz), 2.86 (t, 1H, J=13.3 Hz), 2.67 (t, 1H, J=12.7 Hz), 1.74-1.66 (m, 1H), 1.54-1.48 (m, 1H), 1.45-1.36 (m, 2H), 1.31-1.22 (m, 3H), 1.06 (qd, 2H, J=11.8 Hz, 4.1 Hz); $^{13}$C NMR (100 MHz, CDCl$_3$): δ=165.5, 158.1, 156.5, 146.5, 144.7, 134.8, 133.5, 130.9, 130.3, 124.6, 123.8, 117.2, 114.4, 104.0, 55.9, 47.0, 44.2, 41.8, 35.7, 35.6, 32.7, 31.8, 29.3; HRMS (ESI) for C$_{26}$H$_{32}$N$_6$O$_3$ [M+H]$^+$ calcd: 477.2614, found: 477.2608.

(E)-1-((E)-5-(1-Benzoylpiperidin-4-yl)pent-2-en-1-yl)-2-cyano-3-(pyridin-4-yl)guanidine (FEI-198)

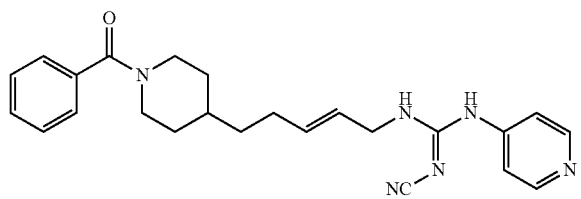 [SMILES: N#C/N=C(\NC/C=C/CCC1CCN(C(=O)c2ccccc2)CC1)Nc1ccncc1]

Obtained from amine 29a (54.4 mg, 0.2 mmol) and phenyl (Z)—N'-cyano-N-(pyridin-4-yl)carbamimidate (47.6 mg, 0.2 mmol) according to the same procedure as that used to prepare FEI-154. Yield: 43.2 mg (52%, MW=416.2325), white foam. $^1$H NMR (400 MHz, CDCl$_3$): δ=8.50-8.21 (m, 2H), 7.35-7.31 (m, 3H), 7.29-7.26 (m, 2H), 7.16-7.04 (m, 2H), 6.14 (brs, 1H, N—H), 5.65 (dt, 1H, J=15.4 Hz, 6.6 Hz), 5.41 (dt, 1H, J=15.4 Hz, 6.1 Hz), 4.65-4.50 (m, 1H), 3.87 (t, 2H, J=5.4 Hz), 3.72-3.59 (m, 1H), 2.91 (t, 1H, J=12.8 Hz), 2.67 (t, 1H, J=12.9 Hz), 1.78-1.54 (m, 2H), 1.52-1.43 (m, 2H), 1.32-1.25 (m, 3H), 1.15-0.98 (m, 2H); $^{13}$C NMR (100 MHz, CDCl$_3$): δ=170.5, 157.6, 150.6, 144.8, 136.1, 135.2, 129.7, 128.6, 126.7, 124.5, 116.7, 115.4, 48.1, 44.4, 42.5, 35.7, 35.6, 32.8, 31.8, 29.3; HRMS (ESI) for C$_{24}$H$_{28}$N$_6$O [M+H]$^+$ calcd: 417.2403, found: 417.2404.

(E)-2-Cyano-1-((E)-5-(1-(furan-2-carbonyl)piperidin-4-yl)pent-2-en-1-yl)-3-(pyridin-4-yl)guanidine (FEI-199)

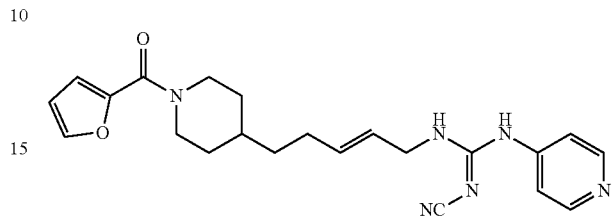

Obtained from amine 29b (52.4 mg, 0.2 mmol) and phenyl (Z)—N'-cyano-N-(pyridin-4-yl)carbamimidate (47.6 mg, 0.2 mmol) according to the same procedure as that used to prepare FEI-154. Yield: 45.7 mg (56.3%, MW=406.2117), white foam. $^1$H NMR (400 MHz, CDCl$_3$): δ=8.48-8.30 (m, 2H), 7.43-7.38 (m, 1H), 7.19-7.10 (m, 2H), 6.83 (d, 1H, J=3.5 Hz), 6.40 (dd, 1H, J=3.3 Hz, 1.7 Hz), 6.09 (brs, 1H, N—H), 5.67 (dt, 1H, J=15.5 Hz, 6.4 Hz), 5.44 (dt, 1H, J=15.5 Hz, 6.0 Hz), 4.50-4.28 (m, 2H), 3.90 (t, 2H, J=5.6 Hz), 3.16-2.48 (m, 2H), 1.75-1.65 (m, 2H), 1.58-1.43 (m, 2H), 1.34-1.25 (m, 3H), 1.13 (qd, 2H, J=12.2 Hz, 3.0 Hz); $^{13}$C NMR (100 MHz, CDCl$_3$): δ=159.3, 157.7, 150.8, 147.8, 144.7, 143.7, 135.3, 124.5, 116.8, 115.8, 115.5, 111.2, 46.9, 44.4, 43.3, 35.6, 35.5, 32.8, 31.8, 29.3; HRMS (ESI) for C$_{22}$H$_{26}$N$_6$O$_2$ [M+H]$^+$ calcd: 407.2195, found: 407.2195.

(E)-2-Cyano-1-(pyridin-4-yl)-3-((E)-5-(1-(thiophene-2-carbonyl)piperidin-4-yl)pent-2-en-1-yl)guanidine (FEI-200)

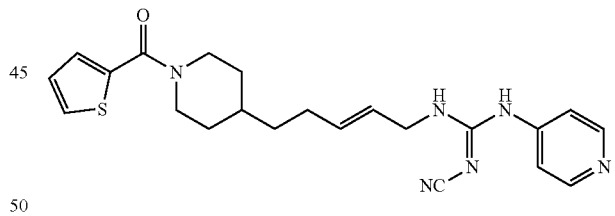

Obtained from amine 29c (55.6 mg, 0.2 mmol) and phenyl (Z)—N'-cyano-N-(pyridin-4-yl)carbamimidate (47.6 mg, 0.2 mmol) according to the same procedure as that used to prepare FEI-154. Yield: 44.5 mg (52.7%, MW=422.1889), white foam. $^1$H NMR (400 MHz, CDCl$_3$): δ=8.47-8.28 (m, 2H), 7.36 (dd, 1H, J=5.1 Hz, 0.9 Hz), 7.18 (dd, 1H, J=3.5 Hz, 0.9 Hz), 7.17-7.08 (m, 2H), 6.97 (dd, 1H, J=4.8 Hz, 3.7 Hz), 6.18 (brs, 1H, N—H), 5.67 (dt, 1H, J=15.2 Hz, 6.4 Hz), 5.43 (dt, 1H, J=15.4 Hz, 5.8 Hz), 4.44-4.16 (m, 2H), 3.89 (t, 2H, J=5.4 Hz), 2.96-2.70 (m, 2H), 1.72-1.63 (m, 2H), 1.56-1.40 (m, 2H), 1.34-1.23 (m, 3H), 1.11 (qd, 2H, J=12.3 Hz, 3.6 Hz); $^{13}$C NMR (100 MHz, CDCl$_3$): δ=163.6, 157.7, 150.7, 144.8, 137.1, 135.1, 128.6, 128.5, 126.8, 124.6, 116.9, 115.5, 47.1, 44.4, 43.9, 35.6, 35.5, 32.8, 31.8, 29.3; HRMS (ESI) for C$_{22}$H$_{26}$N$_6$OS [M+H]$^+$ calcd: 423.1967, found: 423.1964.

(E)-2-Cyano-1-((E)-5-(1-(2,6-dimethoxybenzoyl)piperidin-4-yl)pent-2-en-1-yl)-3-(pyridin-4-yl)guanidine (FEI-201)

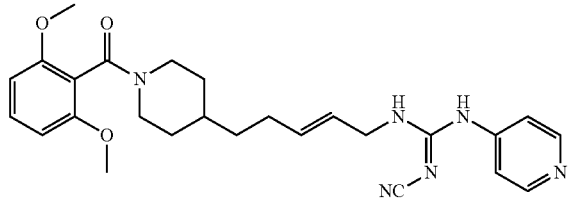 [SMILES: COc1cccc(OC)c1C(=O)N1CCC(CC/C=C/CN/C(=N\C#N)Nc2ccncc2)CC1]

Obtained from amine 29d (66.4 mg, 0.2 mmol) and phenyl (Z)—N'-cyano-N-(pyridin-4-yl)carbamimidate (47.6 mg, 0.2 mmol) according to the same procedure as that used to prepare FEI-154. Yield: 46.4 mg (48.7%, MW=476.2536), white foam. $^1$H NMR (400 MHz, CDCl$_3$): δ=8.35-8.13 (m, 2H), 7.19 (t, 1H, J=8.6 Hz), 7.11-6.96 (m, 2H), 6.46 (d, 2H, J=8.4 Hz), 6.13 (brs, 1H, N—H), 5.68 (dt, 1H, J=15.4 Hz, 6.4 Hz), 5.44 (dt, 1H, J=15.3 Hz, 6.0 Hz), 4.65 (d, 1H, J=12.6 Hz), 3.99 (t, 2H, J=5.6 Hz), 3.68 (s, 3H), 3.67 (s, 3H), 3.41 (d, 1H, J=13.2 Hz), 2.90 (t, 1H, J=12.1 Hz), 2.71 (t, 1H, J=12.2 Hz), 1.80-1.69 (m, 1H), 1.58-1.50 (m, 1H), 1.50-1.37 (m, 2H), 1.35-1.25 (m, 3H), 1.09 (m, 2H); $^{13}$C NMR (100 MHz, CDCl$_3$): δ=156.8, 157.0, 156.4, 150.2, 145.2, 135.0, 130.7, 124.5, 116.7, 114.7, 113.8, 103.8, 55.9, 47.1, 44.6, 41.9, 35.6, 35.5, 32.8, 31.9, 29.4; HRMS (ESI) for C$_{26}$H$_{32}$N$_6$O$_3$ [M+H]$^+$ calcd: 477.2614, found: 477.2608.

General Procedure for the Synthesis of FEI 202-209

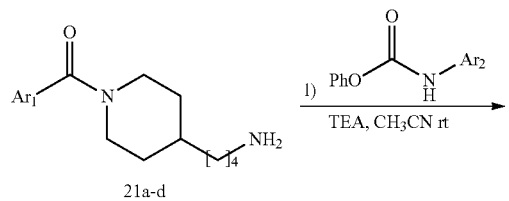

Ar$_1$ = Ph, 21a
  = Fur-2-yl, 21b
  = Thiophen-2-yl, 21c
  = 2,6-(CH$_3$O)$_2$CH$_3$, 21d

1-(4-(1-Benzoylpiperidin-4-yl)butyl)-3-(pyridin-3-yl)urea (FEI-202)

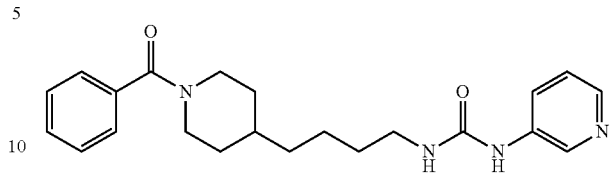

Obtained from amine 21a (39.0 mg, 0.15 mmol) and phenyl pyridin-3-ylcarbamate (32.2 mg, 0.15 mmol) according to the same procedure as that used to prepare FEI-154. Yield: 37.8 mg (66.3%, MW=380.2212), white foam. $^1$H NMR (400 MHz, CDCl$_3$): δ=8.27-8.18 (m, 2H), 8.17 (s, 1H), 8.0 (d, 1H, J=8.4 Hz), 7.48-7.36 (m, 5H), 7.18 (brs, 1H, N—H), 5.87 (t, 1H, J=5.2 Hz, N—H), 4.69 (d, 1H, J=11.6 Hz), 3.75 (d, 1H, J=12.0 Hz), 3.19 (q, 2H, J=6.1 Hz), 3.0 (t, 1H, J=12.1 Hz), 2.78 (t, 1H, J=11.6 Hz), 1.88-1.75 (m, 1H), 1.68-1.57 (m, 1H), 1.56-1.39 (m, 3H), 1.36-1.23 (m, 4H), 1.22-1.05 (m, 2H); $^{13}$C NMR (100 MHz, CDCl$_3$): δ=170.6, 156.1, 142.7, 139.9, 137.0, 135.9, 129.9, 128.7, 126.6, 125.7, 123.7, 48.3, 42.7, 39.8, 36.0 (2C), 33.0, 31.8, 30.2, 23.9; HRMS (ESI) for C$_{22}$H$_{28}$N$_4$O$_2$ [M+H]$^+$ calcd: 381.2291, found: 381.2295.

1-(4-(1-(Furan-2-carbonyl)piperidin-4-yl)butyl)-3-(pyridin-3-yl)urea (FEI-203)

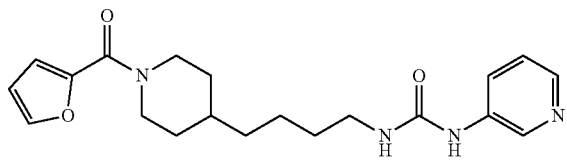 [SMILES: O=C(NCCCCC1CCN(C(=O)c2ccco2)CC1)Nc1cccnc1]

Obtained from amine 21b (37.5 mg, 0.15 mmol) and phenyl pyridin-3-ylcarbamate (32.2 mg, 0.15 mmol) according to the same procedure as that used to prepare FEI-154. Yield: 47.0 mg (84.6%, MW=370.2005), white foam. $^1$H NMR (400 MHz, CDCl$_3$): δ=8.34 (brs, 1H), 8.21 (brs, 1H), 8.10 (d, 1H, J=8.1 Hz), 8.04 (s, 1H), 7.51 (d, 1H, J=0.7 Hz), 7.22 (brs, 1H, N—H), 6.94 (d, 1H, J=3.4 Hz), 6.50 (dd, 1H, J=3.2 Hz, 1.7 Hz), 5.84 (t, 1H, J=5.1 Hz, N—H), 4.70-4.34 (m, 2H), 3.27 (q, 2H, J=5.8 Hz), 3.20-2.97 (m, 1H), 2.94-2.65 (m, 1H), 1.82-1.70 (m, 2H), 1.61-1.46 (m, 3H), 1.40-1.25 (m, 4H), 1.25-1.12 (m, 2H); $^{13}$C NMR (100 MHz, CDCl$_3$): δ=159.5, 156.1, 147.5, 144.0, 142.8, 140.0, 137.1, 125.8, 123.8, 115.9, 111.3, 47.2, 43.6, 39.9, 36.1, 36.0, 32.9, 31.9, 30.2, 23.8; HRMS (ESI) for C$_2$H$_{26}$N$_4$O$_3$ [M+H]$^+$ calcd: 371.2083, found: 371.2085.

1-(Pyridin-3-yl)-3-(4-(1-(thiophene-2-carbonyl)piperidin-4-yl)butyl)urea (FEI-204)

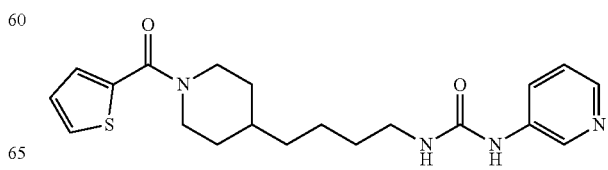

Obtained from amine 21c (40.0 mg, 0.15 mmol) and phenyl pyridin-3-ylcarbamate (32.2 mg, 0.15 mmol) according to the same procedure as that used to prepare FEI-154. Yield: 46.0 mg (87.9%, MW=386.1776), white foam. $^1$H NMR (400 MHz, CDCl$_3$): δ=8.28 (brs, 1H), 8.19 (brs, 1H), 8.07 (d, 1H, J=8.2 Hz), 8.0 (s, 1H), 7.47 (d, 1H, J=4.4 Hz), 7.30 (d, 1H, J=3.3 Hz), 7.24-7.17 (m, 1H, N—H), 7.07 (dd, 1H, J=4.7 Hz, 4.1 Hz), 5.81 (brs, 1H, N—H), 4.66-4.15 (m, 2H), 3.25 (q, 2H, J=5.7 Hz), 3.13-2.76 (m, 2H), 1.83-1.69 (m, 2H), 1.59-1.41 (m, 3H), 1.40-1.25 (m, 4H), 1.19 (q, 2H, J=12.2 Hz, 3.3 Hz); $^{13}$C NMR (100 MHz, CDCl$_3$): δ=163.8, 156.1, 142.8, 140.0, 137.0, 128.7, 128.6, 126.9, 125.8, 123.8, 47.5, 44.0, 39.8, 36.1, 36.0, 32.6, 31.9, 30.2, 23.8; HRMS (ESI) for C$_2$H$_{26}$N$_4$O$_2$S [M+H]$^+$ calcd: 387.1855, found: 387.1857.

1-(4-(1-(2,6-Dimethoxybenzoyl)piperidin-4-yl)butyl)-3-(pyridin-3-yl)urea (FEI-205)

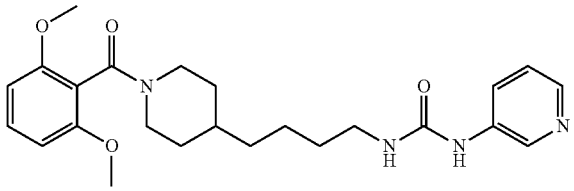 [SMILES: COc1cccc(OC)c1C(=O)N1CCC(CCCCNC(=O)Nc2cccnc2)CC1]

Obtained from amine 21d (48.0 mg, 0.15 mmol) and phenyl pyridin-3-ylcarbamate (32.2 mg, 0.15 mmol), according to the same procedure as that used to prepare FEI-154. Yield: 31.3 mg (47.4%, MW=440.2424), white foam. $^1$H NMR (400 MHz, CDCl$_3$): δ=8.29 (d, 1H, J=5.3 Hz), 8.23-8.04 (m, 2H), 8.0 (d, 1H, J=8.3 Hz), 7.27 (t, 1H, J=8.3 Hz), 7.14 (brs, 1H, N—H), 6.56 (dd, 2H, J=8.3 Hz, 5.4 Hz), 6.01 (t, 1H, J=5.4 Hz, N—H), 4.78 (d, 1H, J=13.0 Hz), 3.78 (s, 3H), 3.76 (s, 3H), 3.49 (d, 1H, J=13.3 Hz), 3.19 (q, 2H, J=5.8 Hz), 2.98 (t, 1H, J=12.8 Hz), 2.80 (td, 1H, J=12.5 Hz, 2.3 Hz), 1.88-1.78 (m, 1H), 1.63-1.55 (m, 1H), 1.50-1.42 (m, 3H), 1.36-1.25 (m, 4H), 1.22-1.08 (m, 2H); $^{13}$C NMR (100 MHz, CDCl$_3$): δ=165.9, 156.5, 156.2, 142.3, 139.9, 137.2, 130.7, 125.3, 123.5, 114.0, 103.9, 55.9, 47.3, 42.0, 39.7, 36.1, 36.0, 33.0, 31.7, 30.2, 23.9; HRMS (ESI) for C$_{24}$H$_{32}$N$_4$O$_4$ [M+H]$^+$ calcd: 441.2502, found: 441.2496.

1-(4-(1-Benzoylpiperidin-4-yl)butyl)-3-(pyridin-4-yl)urea (FEI-206)

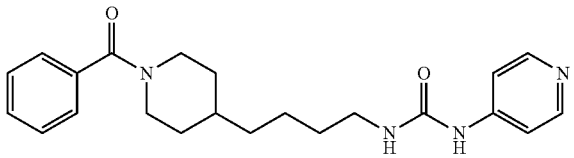 [SMILES: O=C(NCCCCC1CCN(C(=O)c2ccccc2)CC1)Nc1ccncc1]

Obtained from amine 21a (39.0 mg, 0.15 mmol) and phenyl pyridin-4-ylcarbamate (32.2 mg, 0.15 mmol) according to the same procedure as that used to prepare FEI-154. Yield: 48.2 mg (84.5%. MW=380.2212), white foam. $^1$H NMR (400 MHz, CDCl$_3$): δ=8.64 (brs, 1H, N—H), 8.38-8.03 (m, 2H), 7.40-7.32 (m, 3H), 7.31-7.28 (m, 2H), 7.19-7.05 (m, 2H), 5.92 (t, 1H, J=5.4 Hz, N—H), 4.60 (d, 1H, J=11.4 Hz), 3.67 (d, 1H, J=12.1 Hz), 2.80 (q, 2H, J=6.2 Hz), 2.93 (t, 1H, J=12.3 Hz), 2.70 (t, 1H, J=11.8 Hz), 1.73 (d, 1H, J=11.2 Hz), 1.55 (d, 1H, J=11.2 Hz), 1.48-1.30 (m, 3H), 1.27-1.14 (m, 4H), 1.12-0.95 (m, 2H); $^{13}$C NMR (100 MHz, CDCl$_3$): δ=170.1, 155.4, 149.8, 147.6, 135.9, 130.9, 128.7, 126.6, 112.5, 48.3, 42.8, 39.7, 36.0, 35.9, 33.0, 31.8, 30.2, 23.8; HRMS (ESI) for C$_{22}$H$_{28}$N$_4$O$_2$ [M+H]$^+$ calcd: 381.2291, found: 381.2295.

1-(4-(1-(Furan-2-carbonyl)piperidin-4-yl)butyl)-3-(pyridin-4-yl)urea (FEI-207)

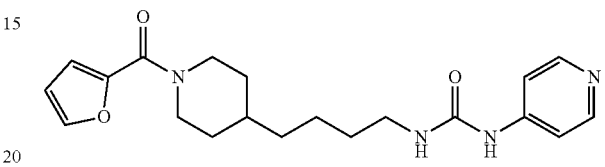

Obtained from amine 21b (37.5 mg, 0.15 mmol) and phenyl pyridin-4-ylcarbamate (32.2 mg, 0.15 mmol) according to the same procedure as that used to prepare FEI-154. Yield: 50.8 mg (91.5%, MW=370.2005), white foam. $^1$H NMR (400 MHz, CDCl$_3$): δ=8.64 (brs, 1H, N—H), 8.25 (brs, 2H), 7.42 (dd, 1H, J=1.7 Hz, 0.7 Hz), 7.27 (brs, 2H), 6.85 (dd, 1H, J=3.5 Hz, 0.7 Hz), 6.42 (dd, 1H, J=3.4 Hz, 1.7 Hz), 5.96 (t, 1H, J=5.5 Hz, N—H), 4.54-4.26 (m, 2H), 3.17 (q, 2H, J=6.0 Hz), 3.10-2.90 (m, 1H), 2.83-2.61 (m, 1H), 1.72-1.63 (m, 2H), 1.50-1.36 (m, 3H), 1.27-1.15 (m, 4H), 1.14-1.01 (m, 2H); $^{13}$C NMR (100 MHz, CDCl$_3$): δ=159.5, 155.4, 149.9, 147.7, 147.4, 144.0, 116.0, 112.5, 111.4, 47.3, 43.6, 39.7, 36.1, 36.0, 33.0, 31.9, 30.2, 23.8; HRMS (ESI) for C$_2$H$_{26}$N$_4$O$_3$ [M+H]$^+$ calcd: 371.2083, found: 371.2093.

1-(Pyridin-4-yl)-3-(4-(1-(thiophene-2-carbonyl)piperidin-4-yl)butyl)urea (FEI-208)

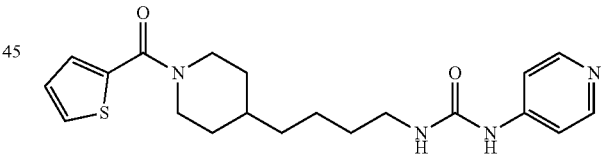

Obtained from amine 21c (40.0 mg, 0.15 mmol) and phenyl pyridin-4-ylcarbamate (32.2 mg, 0.15 mmol) according to the same procedure as that used to prepare FEI-154. Yield: 54.5 mg (94%, MW=386.1776), white foam. $^1$H NMR (400 MHz, CDCl$_3$): δ=8.75 (brs, 1H, N—H), 8.31 (brs, 2H), 7.46 (d, 1H, J=5.0 Hz), 7.34-7.29 (m, 2H), 7.28-7.26 (m, 1H), 7.07 (t, 1H, J=3.8 Hz), 6.10-6.0 (m, 1H, N—H), 4.63-4.23 (m, 2H), 3.22 (q, 2H, J=6.1 Hz), 3.11-2.84 (m, 2H), 1.80-1.68 (m, 2H), 1.58-1.42 (m, 3H), 1.35-1.23 (m, 4H), 1.16 (qd, 2H, J=12.4 Hz, 3.5 Hz); $^{13}$C NMR (100 MHz, CDCl$_3$): δ=163.8, 155.4, 149.8, 147.7, 136.0, 128.7, 128.6, 126.9, 112.5, 47.8, 44.0, 39.8, 36.0 (2C), 32.6, 31.9, 30.2, 23.8; HRMS (ESI) for C$_2$H$_{26}$N$_4$O$_2$S [M+H]$^+$ calcd: 387.1855, found: 387.1858.

1-(4-(1-(2,6-Dimethoxybenzoyl)piperidin-4-yl)butyl)-3-(pyridin-4-yl)urea (FEI-209)

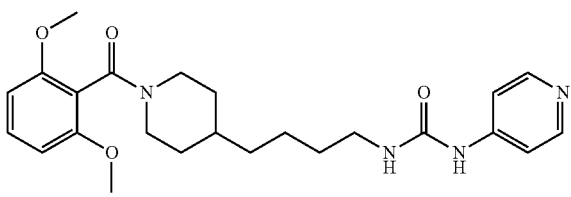 [SMILES: COc1cccc(OC)c1C(=O)N1CCC(CCCCNC(=O)Nc2ccncc2)CC1]

Obtained from amine 21d (48.0 mg, 0.15 mmol) and phenyl pyridin-4-ylcarbamate (32.2 mg, 0.15 mmol), according to the same procedure as that used to prepare FEI-154. Yield: 40.8 mg (61.8%, MW=440.2424), white foam. $^1$H NMR (400 MHz, CDCl$_3$): δ=8.60 (s, 1H, N—H), 8.40-7.92 (m, 2H), 7.21 (t, 1H, J=8.4 Hz), 7.14-7.04 (m, 2H), 6.48 (dd, 2H, J=8.3 Hz, 6.0 Hz), 5.99 (t, 1H, J=4.7 Hz, N—H), 4.69 (d, 1H, J=13.0 Hz), 3.70 (s, 3H), 3.67 (s, 3H), 3.42 (d, 1H, J=13.5 Hz), 3.12 (q, 2H, J=5.8 Hz), 2.91 (td, 1H, J=12.4 Hz, 1.8 Hz), 2.72 (td, 1H, J=12.5 Hz, 2.6 Hz), 1.80-1.71 (m, 1H), 1.56-1.47 (m, 1H), 1.46-1.35 (m, 3H), 1.30-1.19 (m, 4H), 1.10 (qd, 2H, J=12.0 Hz, 3.5 Hz); $^{13}$C NMR (100 MHz, CDCl$_3$): δ=166.0, 156.5, 155.4, 149.6, 147.7, 130.8, 113.9, 112.4, 103.8, 55.9, 47.3, 42.1, 39.7, 36.2, 36.1, 33.0, 31.6, 30.2, 23.9; HRMS (ESI) for C$_{24}$H$_{32}$N$_4$O$_4$ [M+H]$^+$ calcd: 441.2502, found: 441.2499.

General Procedure for the Synthesis of FEI 210-213

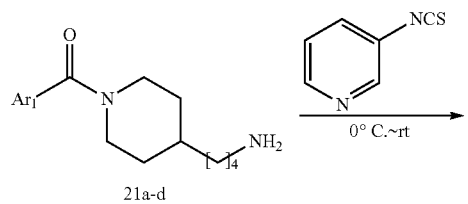

Ar$_1$ = Ph, 21a
= Fur-2-yl, 21b
= Thiophen-2-yl, 21c
= 2,6-(CH$_3$O)$_2$C$_6$H$_3$, 21d

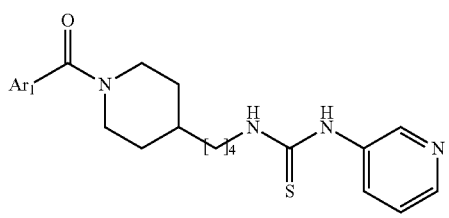

1-(4-(1-Benzoylpiperidin-4-yl)butyl)-3-(pyridin-3-yl)thiourea (FEI-210)

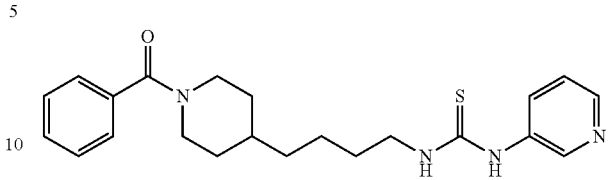

A solution of amine 21a (39.0 mg, 0.15 mmol) in CH$_2$Cl$_2$ (1.0 mL) was cooled to 0° C., 3-isothiocyanatopyridine (20.4 mg, 0.15 mmol) in CH$_2$Cl$_2$ (0.5 mL) was added drop-wise, then the mixture was stirred at 20° C. for 3 h. The solvent was evaporated in vacuo, and the resulting residue was purified by FC (1/12 MeOH/EtOAc) to give FEI-210.

Yield: 46.7 mg (78.6%, MW=396.1984), white foam. $^1$H NMR (400 MHz, CDCl$_3$): δ=8.91-8.65 (m, 1H, N—H), 8.38 (s, 2H), 7.94 (t, 1H, J=7.7 Hz), 7.45-7.34 (m, 5H), 7.29-7.23 (m, 1H), 7.05-6.86 (m, 1H, N—H), 4.67 (d, 1H, J=9.5 Hz), 3.74 (d, 1H, J=11.2 Hz), 3.62-3.52 (m, 2H), 3.01 (t, 1H, J=11.7 Hz), 2.78 (t, 1H, J=10.8 Hz), 1.87-1.77 (m, 1H), 1.69-1.60 (m, 1H), 1.59-1.48 (m 3H), 1.38-1.26 (m 4H), 1.23-1.05 (m 2H); $^{13}$C NMR (100 MHz, CDCl$_3$): δ=181.5, 170.6, 146.2, 145.3, 135.9, 135.4, 131.8, 129.8, 128.6, 126.6, 123.5, 48.3, 44.8, 42.7, 35.9 (2C), 32.9, 31.9, 29.0, 23.9; HRMS (ESI) for C$_{22}$H$_{28}$N$_4$OS [M+H]$^+$ calcd: 397.2062, found: 397.2062.

1-(4-(1-(Furan-2-carbonyl)piperidin-4-yl)butyl)-3-(pyridin-3-yl)thiourea (FEI-211)

Obtained from amine 21b (37.5 mg, 0.15 mmol) and 3-isothiocyanatopyridine (20.4 mg, 0.15 mmol) according to the same procedure as that used to prepare FEI-210. Yield: 56.3 mg (97.2%, MW=386.1776), white foam. $^1$H NMR (400 MHz, CDCl$_3$): δ=8.64 (brs, 1H, N—H), 8.49 (d, 1H, J=2.1 Hz), 8.42 (dd, 1H, J=4.7 Hz. 1.2 Hz), 8.0-7.95 (m, 1H), 7.48-7.46 (m, 1H), 7.32 (dd, 1H, J=8.2 Hz, 4.8 Hz), 6.94-6.89 (m, 1H), 6.84 (t, 1H, J=5.3 Hz, N—H), 6.49 (dd, 1H, J=3.4 Hz, 1.8 Hz), 4.62-4.38 (m, 2H), 3.64 (q, 2H, J=5.9 Hz), 3.24-2.96 (m, 1H), 2.95-2.67 (m, 1H), 1.83-1.74 (m, 2H), 1.66-1.51 (m, 3H), 1.44-1.26 (m, 4H), 1.25-1.14 (m, 2H); $^{13}$C NMR (100 MHz, CDCl$_3$): δ=181.5, 159.4, 147.5, 146.6, 145.6, 143.9, 135.0, 132.1, 123.7, 115.8, 111.3, 47.2, 45.0, 43.5, 36.1, 36.0, 32.8, 32.0, 29.1, 23.9; HRMS (ESI) for C$_{20}$H$_{26}$N$_4$O$_2$S [M+H]$^+$ calcd: 387.1855, found: 387.1856.

49
1-(Pyridin-3-yl)-3-(4-(1-(thiophene-2-carbonyl)piperidin-4-yl)butyl)thiourea (FEI-212)

50
1-(4-(1-(2,6-Dimethoxybenzoyl)piperidin-4-yl)butyl)-3-(pyridin-3-yl)thiourea (FEI-213)

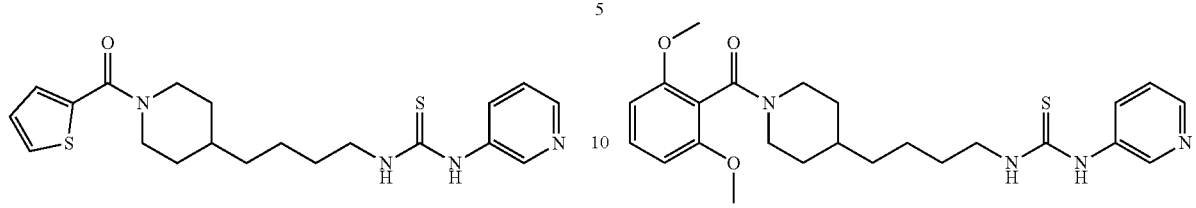

Obtained from amine 21c (40.0 mg, 0.15 mmol) and 3-isothiocyanatopyridine (20.4 mg, 0.15 mmol) according to the same procedure as that used to prepare FEI-210. Yield: 58.4 mg (96.8%, MW=402.1548), white foam. $^1$H NMR (400 MHz, CDCl$_3$): δ=8.63 (brs, 1H, N—H), 8.44 (d, 1H, J=2.2 Hz), 8.40 (dd, 1H, J=4.6 Hz, 1.2 Hz), 7.95 (dt, 1H, J=8.2 Hz, 1.4 Hz), 7.45 (dd, 1H, J=5.0 Hz, 0.9 Hz), 7.30 (dd, 1H, J=8.3 Hz, 4.7 Hz), 7.28 (dd, 1H, J=3.6 Hz, 0.9 Hz), 7.05 (dd, 1H, J=5.0 Hz, 3.7 Hz), 6.85 (t, 1H, J=5.4 Hz, N—H), 4.61-4.23 (m, 2H), 3.62 (q, 2H, J=5.2 Hz), 3.11-2.83 (m, 2H), 1.83-1.72 (m, 2H), 1.63-1.55 (m, 3H), 1.42-1.29 (m, 4H), 1.19 (qd, 2H, J=12.4 Hz, 3.7 Hz); $^{13}$C NMR (100 MHz, CDCl$_3$): δ=181.5, 163.7, 146.5, 145.5, 137.0, 135.1, 132.0, 128.7, 128.6, 126.9, 123.7, 47.4, 44.9, 43.6, 36.1, 36.0, 32.7, 32.2, 29.1, 23.9; HRMS (ESI) for C$_2$H$_{26}$N$_4$OS$_2$ [M+H]$^+$ calcd: 403.1626, found: 403.1627.

Obtained from amine 21d (48.0 mg, 0.15 mmol) and 3-isothiocyanatopyridine (20.4 mg, 0.15 mmol) according to the same procedure as that used to prepare FEI-210. Yield: 65.8 mg (96.2%, MW=456.2195), white foam. $^1$H NMR (400 MHz, CDCl$_3$): δ=9.02-8.87 (m, 1H, N—H), 8.32 (d, 1H, J=2.9 Hz), 8.24 (brs, 1H), 8.09 (d, 1H, J=7.3 Hz), 7.32-7.20 (m, 3H), 6.54 (t, 2H, J=9.2 Hz), 4.79 (d, 1H, J=12.7 Hz), 3.78 (s, 3H), 3.72 (s, 3H), 3.59 (q, 2H, J=4.3 Hz), 3.50 (d, 1H, J=13.2 Hz), 2.99 (t, 1H, J=12.8 Hz), 2.82 (t, 1H, J=12.8 Hz), 1.92-1.83 (m, 1H), 1.63-1.49 (m, 4H), 1.45-1.26 (m, 4H), 1.19 (q, 2H, J=12.9 Hz); $^{13}$C NMR (100 MHz, CDCl$_3$): δ=181.6, 166.0, 156.5, 145.5, 144.8, 136.0, 131.1, 130.7, 123.1, 113.9, 103.9, 55.8, 47.3, 44.6, 42.0, 36.2, 36.0, 33.0, 31.7, 29.1, 24.0; HRMS (ESI) for C$_{24}$H$_{32}$N$_4$O$_3$S [M+H]$^+$ calcd: 457.2273, found: 457.2277.

Alternative Synthesis of aryl- and heteroaryl[4-(4-aminobutyl)piperidine-1-yl]methanones

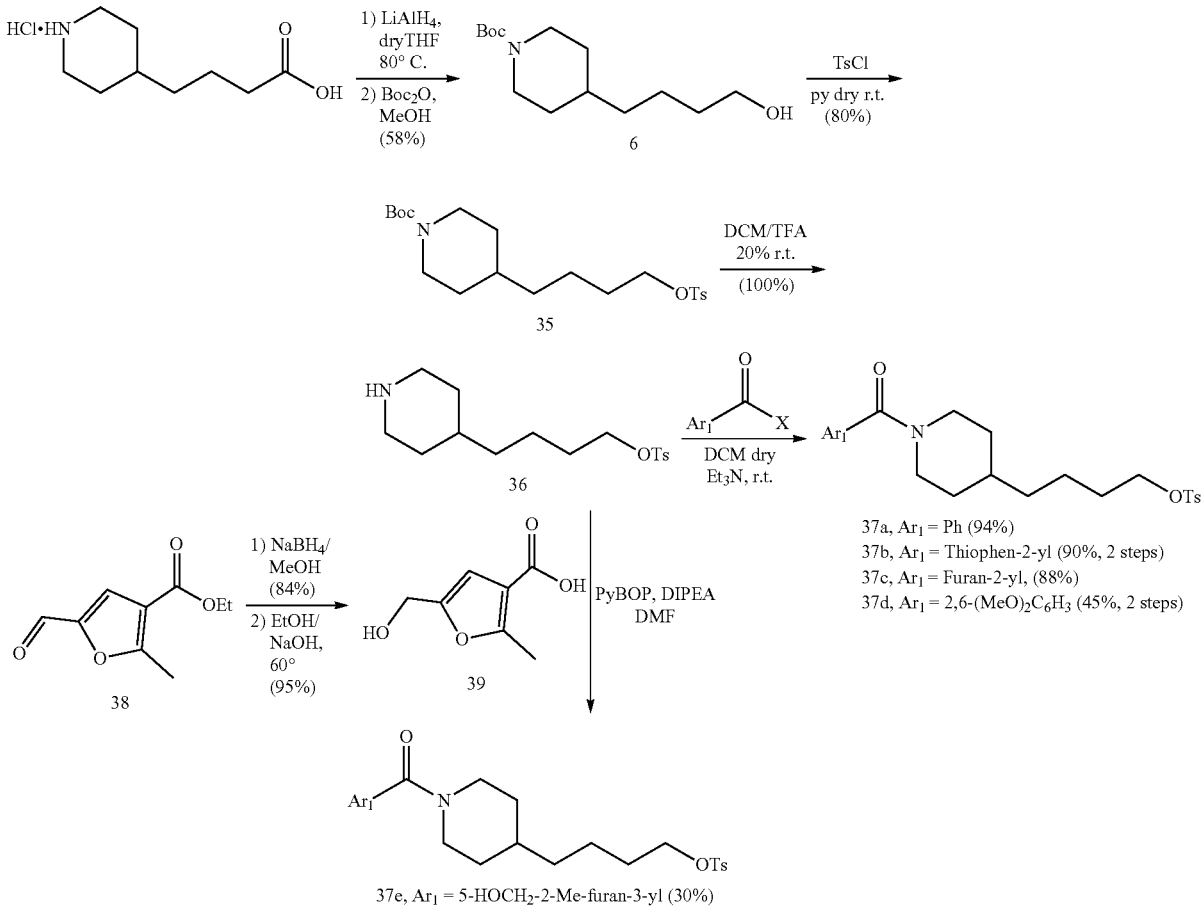

-continued

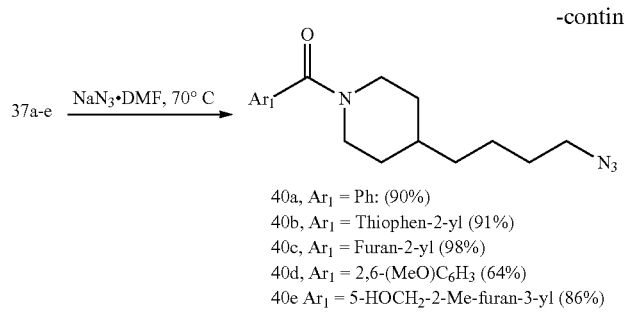 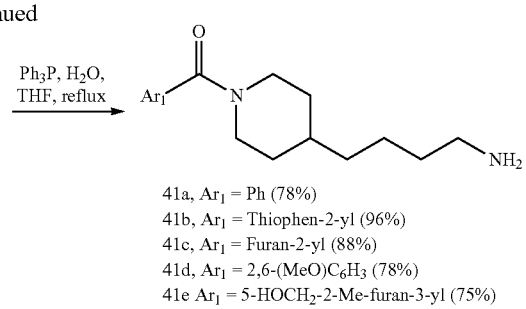

40a, Ar₁ = Ph: (90%)
40b, Ar₁ = Thiophen-2-yl (91%)
40c, Ar₁ = Furan-2-yl (98%)
40d, Ar₁ = 2,6-(MeO)C₆H₃ (64%)
40e Ar₁ = 5-HOCH₂-2-Me-furan-3-yl (86%)

41a, Ar₁ = Ph (78%)
41b, Ar₁ = Thiophen-2-yl (96%)
41c, Ar₁ = Furan-2-yl (88%)
41d, Ar₁ = 2,6-(MeO)C₆H₃ (78%)
41e Ar₁ = 5-HOCH₂-2-Me-furan-3-yl (75%)

Reduction of commercial 4-(piperidin-4-yl)butanoic acid using LiAlH$_4$ as a reducing agent in dry THF, followed by N-protection of the free amino group with Boc$_2$O gave alcohol 6. Subsequent tosylation with TsCl in dry pyridine followed by N-deprotection by acid treatment with 20% CF$_3$COOH in CH$_2$Cl$_2$ furnished 4-(piperidin-4-yl)butyl 4-methylbenzenesulfonate 36 in quantitative yield. This compound was N-acylated with benzoyl, thiophene-2-carbonyl, 2-furoyl and 2,6-dimethoxybenzoyl chloride in the presence of Et$_3$N to give compounds 37a-d. In the case of the 5-hydroxymethyl-2-methyl-3.furoyl derivative the N-acylation was performed with the corresponding carboxylic acid 39 and PyBOP/DIPEA as coupling agents. On its side, 39 was prepared from 2-methyl-5-(D-arabino-tetrahydroxybutyl), ethyl ester, by glycol oxidation with NaIO$_4$, followed by aldehyde reduction and hydrolysis of the ethyl ester. Problems with the purification of these compounds lowered the yield of the coupling reaction. Finally, displacement of the tosyl group by azide and subsequent Staudinger reduction gave the compounds the primary amines 41a-e.

Procedures

Synthesis of tert-Butyl 4-(4-tosyloxybutyl)piperidine-1-carboxylate (35)

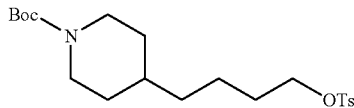 [SMILES: Cc1ccc(S(=O)(=O)OCCCCC2CCN(C(=O)OC(C)(C)C)CC2)cc1]

To a solution of compound 6 (148.5 mg, 0.58 mmol) in dry pyridine (3 mL) cooled to 0° C., TsCl (445 mg, 2.31 mmol) was slowly added. The reaction was stirred at room temperature for 3.5 h. Then, the mixture was cooled to 0° C. Water was added and the mixture was stirred at room temperature for 10 min. After evaporation of the solvent, the residue was dissolved in AcOEt and washed with sat. aq. sol. of NaHCO$_3$ and brine. The dried organic phase was evaporated to dryness. Purification by FC (1/4 EtOAc:cyclohexane), gave 35 Yield: (189.3 mg, 0.46 mmol, 80%, MW: 411.557) as a colorless oil. IR (v cm$^{-1}$) 1685 (C=O). $^1$H-NMR (300 MHz, CDCl$_3$, δ ppm, J Hz) δ 7.80-7.77 (m, 2H, H-arom.), 7.35-7.32 (m, 2H, H-arom.), 4.06-4.04 (m, 2H, H-6a, H-2a), 4.02 (t, 2H, J$_{4',3}$=6.6, H-4'), 2.63 (td, 2H, J$_{6b,5}$=J$_{2b,3}$=3, J$_{6b, 6a}$=J$_{2b, 2a}$=13.2, H-6b, H-2b), 2.44 (s, 3H, Me), 1.67-1.56 (m, 4H, H-5a, H-3a, H-3'), 1.45 (s, 9H, —C(CH$_3$)$_3$), 1.37-1.23 (m, 3H, H-4, H-2'), 1.20-1.12 (m, 2H, H-1'), 1.08-0.94 (m, 2H, H-5b, H-3b). $^{13}$C-NMR (75.4 MHz, CDCl$_3$, δ ppm) 155.0 (C=O), 144.8, 133.4, 129.9, 128.0 (C-arom.), 79.3 (—C(CH$_3$)$_3$), 70.6 (C-4'), 44.0 (C-6, C-2), 35.9 (C-4), 35.8 (C-1'), 32.1 (C-5, C-3), 29.1 (C-3'), 28.6 (—C(CH$_3$)$_3$), 22.6 (C-2'), 21.8 (Me). CIMS m/z 412 [10%, (M+H)$^+$], 338 [67%, (M-OC(CH$_3$)$_3$)$^+$]. HRCIMS m/z found 412.2155, calc. for C$_{21}$H$_{34}$O$_5$NS: 412.2158.

Synthesis of 1-benzoyl-4-(4-tosyloxybutyl)piperidine (37a)

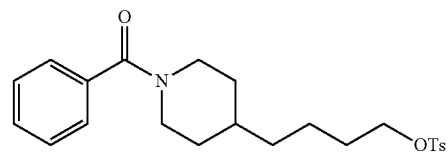 [SMILES: Cc1ccc(S(=O)(=O)OCCCCC2CCN(C(=O)c3ccccc3)CC2)cc1]

Compound 35 (877.3 mg, 2.13 mmol) was dissolved in 20% CF$_3$COOH/CH$_2$Cl$_2$ (15 mL) and the mixture was stirred at room temperature for 2.5 h and then the solvent was evaporated in vacuo. Triethyl amine (10. 67 mmol, 1.5 mL) and benzoyl chloride (2.77 mmol) were subsequently added under N$_2$ atmosphere, to a cooled (0° C.) solution of the residue in dry CH$_2$Cl$_2$ (9 mL). After 2.5 h, the reaction was worked up by dilution with saturated aqueous. NH$_4$Cl and extracted with CH$_2$Cl$_2$ (15 mL, 3 times). The organic phases were combined and washed with brine, dried (MgSO$_4$), filtered and concentrated in vacuo to dryness. The residue was purified by FC (EtOAc/cyclohexane, 1/2→1/1→2/1). Yield: (831.1 mg, 2.00 mmol, 94%, MW: 415.548) as a colourless oil. IR (v cm$^{-1}$) 1625 (C=O). $^1$H-NMR (300 MHz, CDCl$_3$, δ ppm, J Hz) δ 7.79-7.77 (m, 2H, H-arom. Ts), 7.38 (brs, 5H, H-arom. Ph), 7.35-7.32 (m, 2H, H-arom. Ts), 4.66 (brs, 1H, H-2a)*, 4.02 (t, 2H, J$_{4',3}$=6.6, H-4'), 3.75 (brs, 1H, H-6a)*, 2.85 (brs, 2H, H-6b, H-2b), 2.45 (s, 3H, Me), 1.74-1.59 (m, 4H, H-3', H-3a, H-5a), 1.47-1.1 (m, 7H, H-4, H-2', H-1', H-3b, H-5b). (These protons could be exchanged. $^{13}$C-NMR (75.4 MHz, CDCl$_3$, δ ppm) 170.4 (C=O), 144.8, 136.5, 133.3, 130.0, 129.7, 128.5, 128.0, 126.9 (C-arom.), 70.5 (C-4''), 47.7 (C-2 or C-6), 42.7 (C-6 or C-2), 36.1 (C-4), 35.8 (C-1'), 32.5 (C-3, C-5), 29.1 (C-3'), 22.6 (C-2'), 21.8 (Me). CIMS m/z 416 [100%, (M+H)$^+$], 417 [27%, (M+2H)$^+$]. HRCIMS m/z found 416.1887, calc. for C$_{23}$H$_{30}$O$_4$NS: 416.1896.

1-(thiophene-2-carbonyl)-4-(4-tosyloxybutyl)-2-yl)piperidine (37b)

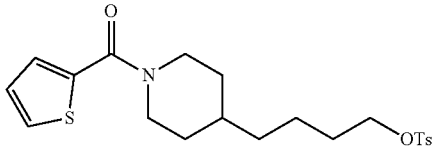

Same procedure as that applied for the preparation of 37a, starting with 35 and thiophene-2-carbonyl chloride. Yield: (763 mg, 1.81 mmol, 85%, MW: 421.570) as a yellow oil. IR (v cm$^{-1}$) 1608 (C=O). $^1$H-NMR (300 MHz, CDCl$_3$, δ ppm, J Hz) δ 7.80-7.77 (m, 2H, H-arom. Ts), 7.41 (dd, 1H, J$_{5'',4''}$=5.1, J$_{5'',3''}$=1.2, H-5''), 7.35-7.32 (m, 2H, H-arom. Ts), 7.25 (dd, 1H, J$_{3'',4''}$=3.6, H-3''), 7.02 (dd, 1H, H-4''), 4.40 (brs, 2H, H-6a, H-2a), 4.02 (t, 2H, J$_{4',3'}$=6.3, H-4'), 2.89 (m, 2H, H-6b, H-2b), 2.44 (s, 3H, Me), 1.75-1.59 (m, 4H, H-3', H-3a, H-5a), 1.51-1.28 (m, 3H, H-4, H-2'), 1.24-1.06 (m, 4H, H-1', H-3b, H-5b). $^{13}$C-NMR (75.4 MHz, CDCl$_3$, δ ppm) 163.6 (C=O), 144.8, 137.6, 133.3, 129.9, 128.5, 128.3, 128.0, 126.7 (C-arom.), 70.5 (C-4''), 45.8 (C-2, C-6), 36.1 (C-4), 35.7 (C-1'), 32.5 (C-3, C-5), 29.1 (C-3'), 22.6 (C-2'), 21.7 (Me). CIMS m/z 422 [100%, (M+H)$^+$], 423 [26%, (M+2H)$^+$]. HRCIMS m/z found 422.1456, calc. for C$_{21}$H$_{28}$O$_4$NS$_2$: 422.1460.

1-(2-furoyl)-4-(4-tosyloxybutyl)-2-yl)piperidine (37c)

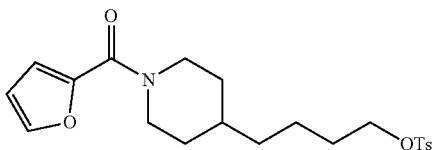 [SMILES: Cc1ccc(S(=O)(=O)OCCCCC2CCN(C(=O)c3ccco3)CC2)cc1]

Same procedure as that applied for the preparation of 37a, starting with 35 and 2-furoyl chloride. Yield: (758.3 mg, 1.87 mmol, 88%, MW: 405.509) as a pale yellow oil. IR (v cm$^{-1}$) 1616 (C=O). $^1$H-NMR (300 MHz, CDCl$_3$, δ ppm, J Hz) δ 7.78 (d, 2H, J$_{H,H}$=8.1, H-arom. Ts), 7.56 (d, 1H, J$_{5''4''}$=0.9, H-5''), 7.33 (d, 2H, J$_{H,H}$=8.4, H-arom.Ts), 6.91 (d, 1H, J$_{3'',4''}$=3.3, H-3''), 6.45 (dd, 1H, H-4''), 4.48 (brs, 2H, H-6a, H-2a), 4.02 (t, 2H, J$_{4',3'}$=6.3, H-4'), 2.87 (brs, 2H, H-6b, H-2b), 2.43 (s, 3H, Me), 1.73-1.59 (m, 4H, H-3', H-3a, H-5a), 1.51-1.27 (m, 3H, H-4, H-2'), 1.24-1.1 (m, 4H, H-1', H-3b, H-5b). $^{13}$C-NMR (75.4 MHz, CDCl$_3$, δ ppm) 159.3 (C=O), 148.2, 144.8, 143.5, 133.3, 129.9, 127.9, 115.7, 111.2 (C-arom.), 70.5 (C-4''), 49.5 (C-2, C-6), 36.1 (C-4), 35.7 (C-1'), 32.5 (C-3, C-5), 29.1 (C-3'), 22.6 (C-2'), 21.7 (Me). CIMS m/z 406 [100%, (M+H)$^+$], 234 [30%, (M+H-OTs)$^+$]. HRCIMS m/z found 406.1678, calc. for C$_{21}$H$_{28}$O$_5$NS: 406.1688.

1-(2,6-dimethoxybenzoyl)-4-(4-tosyloxybutyl)piperidine (37d)

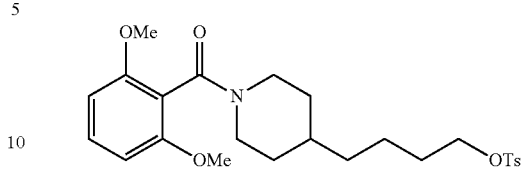

Same procedure as that applied for the preparation of 37a, starting with 35 and 2,6-dimethoxybenzoyl chloride. Yield: (435.6 mg, 0.916 mmol, 43%, MW: 475.600) as a pale yellow oil. $^1$H-NMR (300 MHz, CDCl$_3$, δ ppm, J Hz) δ 7.83 (d, 2H, J$_{H,H}$=8.3, H-arom. Ts), 7.39 (d, 2H, J$_{H,H}$=8.2, H-arom. Ts), 7.29 (t, 1H, J$_{H,H}$=6.8, H-arom.), 6.61 (d, 1H, H-arom.), 6.58 (d, 1H, H-arom.), 4.86-4.77 (m, 1H, H-6a or H-2a), 4.07 (t, 2H, J$_{4',3}$=6.4, H-4'), 3.84 (s, 3H, OCH$_3$), 3.83 (s, 3H, OCH$_3$), 3.52-3.46 (m, 1H, H-6a or H-2a), 2.94 (td, 1H, J$_{H,H}$=13.2, J$_{H,H}$=3.2, H-6b or H-2b), 2.76 (td, 1H, J$_{H,H}$=12.7, J$_{H,H}$=2.9, H-6b or H-2b), 2.49 (s, 3H, CH$_3$), 1.68-0.90 (m, 11H, H-3, H-4, H-5, H-1', H-2', H-3'). $^{13}$C-NMR (75.4 MHz, CDCl$_3$, δ ppm) δ 165.3 (C=O), 156.8, 156.7, 144.9, 133.3, 130.1, 130.0, 128.0, 115.2, 104.1 (C-arom.), 70.6 (C-4'), 56.0 (OCH$_3$), 55.9 (OCH$_3$), 47.0, 41.7 (C-2, C-6), 36.2, 35.6, 32.8, 32.0, 29.1, 22.7 (C-3, C-5, C-4, C-3', C-2', C-1'), 21.8 (CH$_3$).

Ethyl 5-formyl-2-methylfuran-3-carboxylate (38)

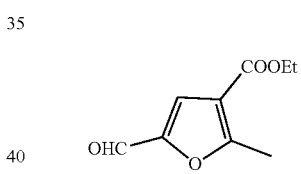

To a solution of ethyl 2-methyl-5-(D-arabino-tetrahydroxybutyl)furan-3-carboxylate (2.91 g, 10.61 mmol) [a) Robina, I.; Moreno-Vargas, A. J.; Fernandez-Bolanos, J. G.; F., Jose; Demange, R.; Vogel, P. *Bioorg. & Med. Chem. Lett.* 2001, 11,2555-2559. b) Bartoli, G.; Fernandez-Bolanos, J. G.; Di Antonio, G.; Foglia, G.; Giuli, S.; Gunnella, R.; Mancinelli, M.; Marcantoni, E.; Paoletti, M. *J. Org. Chem.* 2007, 72, 6029-6036] in MeOH (40 mL) at 0° C. was added slowly a solution of NaIO$_4$ (5.22 g, 24.40 mmol) in water (30 mL). The mixture was stirred at room temperature for 40 min. After evaporation of the solvent, the residue was diluted with CH$_2$Cl$_2$ and washed with water and brine. The organic phases were dried, filtered and concentrated. The residue was purified by FC (1/3 EtOAc/cyclohexane) to give 38 (1.66 g, 9.14 mmol, 86%, MW: 182.18) as white solid. IR (v cm$^{-1}$) 1710 (C=O), 1684, 1590 (C=C). $^1$H NMR (300 MHz, CDCl$_3$, δ ppm, J Hz) δ 9.54 (s, 1H, CHO), 7.46 (s, 1H, H-3), 4.31 (q, 2H, 2J$_{H,H}$=7.2, —CH$_2$CH$_3$), 2.67 (s, 3H, Me), 1.35 (t, 3H, —CH$_2$CH$_3$). $^{13}$C NMR (75.4 MHz, CDCl$_3$, δ ppm) δ 177.2 (CHO), 164.8 (COOEt), 162.7 (C-5), 150.4 (C-2), 122.6 (C-3), 116.6 (C-4), 61.0 (—CH$_2$CH$_3$), 14.4 (Me), 14.4 (—CH$_2$CH$_3$). CIMS m/z 183 [100%, (M+H)$^+$], 182 [32%, (M)$^+$]. HRCIMS m/z found 183.0653, calc. for C$_9$H$_{11}$O$_4$: 183.0657.

5-Hydroxymethyl-2-methylfuran-3-carboxylic acid (39)

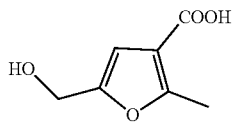

To a solution of 38 (1.64 g, 9.01 mmol) in MeOH, NaBH$_4$ (682 mg, 18.02 mmol) was added. The mixture was stirred at room temperature for 30 min. The mixture was neutralized with citric acid. After evaporation of solvent, the residue was diluted with CH$_2$Cl$_2$ and washed with water. The organic phases were dried, filtered and concentrated to give ethyl 5-hydroxymethyl-2-methylfuran-3-carboxylic ester (1.39 g, 7.54 mmol, 84%, MW: 184.191) as a white solid. IR (ν cm$^{-1}$) 3423 (OH), 1710 (C=O). $^1$H NMR (300 MHz, CDCl$_3$, δ ppm, J Hz) δ 6.52 (s, 1H, H-3), 4.53 (s, 1H, H-1'), 4.26 (q, 2H, $^2$J$_{H,H}$=6.9, —CH$_2$CH$_3$), 2.55 (s, 3H, Me), 1.33 (t, 3H, —CH$_2$CH$_3$). $^{13}$C NMR (75.4 MHz, CDCl$_3$, δ ppm) δ 177.2 (CHO), 164.8 (COOEt), 162.7 (C-5), 150.4 (C-2), 122.6 (C-3), 116.6 (C-4), 61.0 (—CH$_2$CH$_3$), 14.4 (Me), 14.4 (—CH$_2$CH$_3$). CIMS m/z 185 [46%, (M+H)$^+$], 184 [61%, (M)$^+$], 167 [100%, (M-OH+H)$^+$]. HRCIMS m/z found 184.0732, calc. for CH$_{12}$O$_4$: 184.0736. This ester (1.36 mg, 7.41 mmol) was dissolved in 1M NaOH/EtOH (30 mL) and the mixture was stirred at 60° C. for 5.5 h. The mixture was cooled to 0° C., neutralized with acid resin IR 120 (H+), filtered and concentrated to give 39 (1.10 g, 7.04 mmol, 95%, MW: 156.137) as a white solid. IR (ν cm$^{-1}$) 3330 (OH), 1665 (C=O). $^1$H NMR (300 MHz, MeOD, δ ppm, J Hz) δ 6.50 (s, 1H, H-3), 4.45 (s, 1H, H-1'), 2.54 (s, 3H, Me). $^{13}$C NMR (75.4 MHz, MeOD, δ ppm) δ 167.3 (—COOH), 160.4 (C-5), 154.1 (C-2), 115.4 (C-4), 109.4 (C-3), 57.1 (C-1'), 13.7 (Me). CIMS m/z 158 [63%, (M+2H)$^+$], 157 [65%, (M+H)$^+$], 139 [100%, (M-OH+H)$^+$]. HRCIMS m/z found 157.0501, calc. for C$_7$H$_9$O$_4$: 157.0501.

1-(5-Hydroxymethyl-2-methyl-3-furoyl)-4-(4-tosyloxybutyl)piperidine (37e)

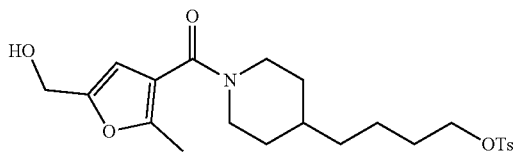 [SMILES: Cc1ccc(S(=O)(=O)OCCCCC2CCN(C(=O)c3cc(CO)oc3C)CC2)cc1]

Compound 35 (879.5 mg, 2.14 mmol) was dissolved in 20% CF$_3$COOH:CH$_2$Cl$_2$ (15 mL) and the mixture was stirred at room temperature for 2 h. The solvent was evaporated. DIPEA (1.9 mL, 10.69 mmol), carboxylic acid 39 (440 mg, 2.78 mmol) and PyBOP (1.93 g, 3.64 mmol) were added in succession to a solution of the residue in DMF (7 mL). The mixture was stirred overnight at 20° C. The solvent was evaporated in vacuo and the residue was dissolved in EtOAc and washed with aqueous HCl (1M), then with a saturated aqueous. Solution of NaHCO$_3$ and, finally with water. After drying (MgSO$_4$) the solvent was evaporated in vacuo. FC (19/1 diethyl ether/acetone), gave 37e (292 mg, 0.65 mmol, 30%, MW: 449.562) as a pale yellow oil. IR (ν cm$^{-1}$) 3330 (OH), 1596 (C=O). $^1$H NMR (300 MHz, CDCl$_3$, ppm, J Hz) δ 7.78 (d, 2H, J$_{H,H}$=8.4, H-arom. Ts), 7.34 (d, 2H, J$_{H,H}$=7.8, H-arom. Ts), 6.21 (s, 1H, H-1"), 4.54-4.09 (m, 4H, —CH$_2$OH, H-6a, H-2a), 4.02 (t, 2H, J$_{4',3'}$=6.3, H-4'), 2.82 (brs, 2H, H-6b, H-2b), 2.45 (s, 3H, Me), 2.35 (s, 3H, Me), 1.90 (br. s, 1H, OH), 1.70-1.59 (m, 4H, H-3', H-3a, H-5a), 1.49-1.0 (m, 7H, H-4, H-2', H-1', H-3b, H-5b). $^{13}$C-NMR (75.4 MHz, CDCl$_3$, δ ppm) 165.0 (C=O), 153.1, 151.9, 144.9, 133.3, 130.0, 128.0, 120.4, 116.8, 108.4 (C-arom.), 70.5 (C-4"), 57.4 (—CH$_2$OH), 45.2 (C-2, C-6), 36.1 (C-4), 35.8 (C-1'), 32.5 (C-3, C-5), 29.1 (C-3'), 22.6 (C-2'), 21.8 (CH$_3$), 13.1 (CH$_3$). LSIMS m/z 472 [64%, (M+Na)$^+$]. HRLSIMS m/z found 472.1765, calc. for C$_{23}$H$_{31}$O$_6$NSNa: 472.1770.

4-(4-Azidobutyl)-1-benzoylpiperidine (40a)

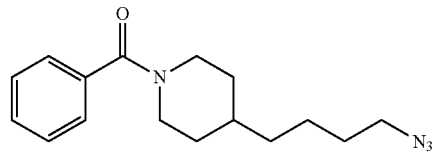 [SMILES: [N-]=[N+]=NCCCCC1CCN(C(=O)c2ccccc2)CC1]

To a solution of 37a (326 mg, 0.785 mmol) in DMF (4 mL), NaN$_3$ (153 mg, 2.355 mmol) was added. The reaction was stirred at 70° C. for 3 to 4 h (TLC monitoring). After cooling to room temperature the solvent was evaporated and the residue was dissolved in CH$_2$Cl$_2$ and washed with water and brine. The dried organic phase was evaporated and the residue was purified by FC (EtOAc/cyclohexane, 1/3→1/2), to give 40a. Yield: (202.3 mg, 0.71 mmol, 90%, MW: 286.379) as a pale yellow oil. The NMR data were in accordance with date from the literature given for this compound [Galli, U.; Ercolano, E.; Carraro, L.; Roman, C. R. B.; Sorba, G.; Canonico, P. L.; Genazzani, A. A.; Tron, G. C.; Billington, R. A. *Chem Med Chem*, 2008, 3, 771-779].

4-(4-Azidobutyl)-1-(thiophene-2-carbonyl)piperidine (40b)

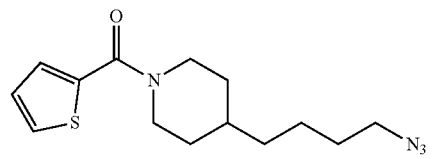 [SMILES: [N-]=[N+]=NCCCCC1CCN(C(=O)c2cccs2)CC1]

Same procedure as for the preparation of 40a starting with 37b (331 mg, 0.785 mmol). Yield: (208.8 mg, 0.714 mmol, 91%, MW: 292.401) as a pale yellow oil. IR (ν cm$^{-1}$) 2090 (N$_3$), 1610 (C=O). $^1$H-NMR (300 MHz, CDCl$_3$, δ ppm, J Hz) δ 7.41 (dd, 1H, J$_{5",4"}$=4.8, J$_{5",3"}$=1.2, H-5"), 7.26 (dd, 1H, J$_{3",4"}$=3.3, H-3"), 7.02 (dd, 1H, H-4"), 4.41 (m, 2H, H-2a, H-6a), 3.27 (t, 2H, J$_{4',3'}$=6.6, H-4'), 2.91 (m, 2H, H-2b, H-6b), 1.76 (br d, 2H, H-3a, H-5a), 1.64-1.50 (m, 3H, H-4, H-3'), 1.46-1.38 (m, 4H, H-2', H-1'), 1.26-1.13 (m, 2H, H-3b, H-5b). $^{13}$C-NMR (75.4 MHz, CDCl$_3$, δ ppm) 163.6 (C=O), 137.7 (C-2"), 128.5 (C-5"), 128.3 (C-3"), 126.7 (C-4"), 51.5 (C-4'), 46.7 (C-6, C-2), 36.2 (C-4), 36.0 (C-2), 32.6 (C-5, C-3), 29.1 (C-3'), 23.9 (C-1'). CIMS m/z 293 [83%, (M+H)$^+$], 292 [19%, (M)$^+$]. HRCIMS m/z found 293.1431, calc. for C$_{14}$H$_{21}$ON$_4$S: 293.1436.

4-(4-Azidobutyl)-1-(2-furoyl)piperidine (40c)

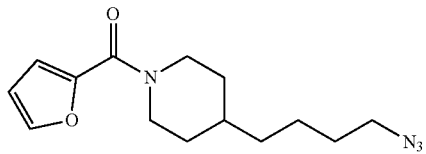

Same procedure as for the preparation of 40a starting with 37c. (318.3 mg, 0.785 mmol). Yield: (212.6 mg, 0.769 mmol, 98%, MW: 276.340) as a pale yellow oil. IR (v cm$^{-1}$) 2091 (N$_3$), 1618 (C=O). $^1$H-NMR (300 MHz, CDCl$_3$, δ ppm, J Hz) δ 7.45 (dd, 1H, J$_{5''-4''}$=1.5, J$_{5''-3''}$=0.6, H-5''), 6.91 (dd, 1H, J$_{3''-4''}$=3.3, H-3''), 6.44 (dd, 1H, H-4''), 4.49 (m, 2H, H-2a, H-6a), 3.26 (t, 2H, J$_{4'-3'}$=6.9, H-4'), 2.89 (m, 2H, H-2b, H-6b), 1.76 (br d, 2H, H-3a, H-5a), 1.63-1.50 (m, 1H, H-4), 1.45-1.39 (m, 4H, H-3', H-1'), 1.37-1.27 (m, 2H, H-2'), 1.25-1.13 (m, 2H, H-3b, H-5b). $^{13}$C-NMR (75.4 MHz, CDCl$_3$, δ ppm) 159.3 (C=O), 148.3 (C-2''), 143.5 (C-5''), 115.7 (C-3''), 111.2 (C-4''), 51.5 (C-4'), 44.9 (C-6, C-2), 36.2 (C-4), 36.0 (C-2), 32.6 (C-5, C-3), 29.1 (C-3'), 23.9 (C-1). CIMS m/z 277 [59%, (M+H)$^+$]. HRCIMS m/z found 277.1670, calc. for C$_{14}$H$_{21}$O$_2$N$_4$: 277.1665.

4-(4-Azidobutyl)-1-(2,6-dimethoxybenzoyl)piperidine (40d)

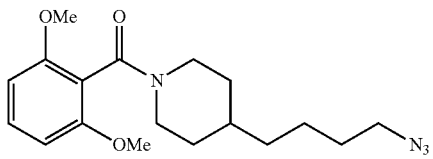 [SMILES: COc1cccc(OC)c1C(=O)N1CCC(CCCCN=[N+]=[N-])CC1]

Same procedure as for the preparation of 40a starting with 37d. (373.3 mg, 0.785 mmol). Yield: (174.0 mg, 0.502 mmol, 64%, MW: 346.431) as a pale yellow oil. IR (v cm$^{-1}$) 2092 (N$_3$), 1633 (C=O). $^1$H-NMR (300 MHz, CDCl$_3$, δ ppm, J Hz) δ 7.29 (t, 1H, J$_{H,H}$=8.3, H-arom.), 6.60 (d, 1H, H-arom.), 6.59 (d, 1H, H-arom.), 4.88-4.80 (m, 1H, H-6a or H-2a), 3.85 (s, 3H, OCH$_3$), 3.83 (s, 3H, OCH$_3$), 3.55-3.46 (m, 1H, H-6a or H-2a), 3.31 (t, 2H, J$_{4',3'}$=6.8, H-4'), 2.96 (td, 1H, J$_{H,H}$=12.8, J$_{H,H}$=2.6, H-6b or H-2b), 2.78 (td, 1H, J$_{H,H}$=12.8, J$_{H,H}$=2.9, H-6b or H-2b), 1.84-1.08 (m, 11H, H-3, H-4, H-5, H-1', H-2', H-3'). $^{13}$C-NMR (75.4 MHz, CDCl$_3$, δ ppm) δ 165.2 (C=O), 156.8, 156.7, 130.0, 115.2, 104.1 (C-arom.), 56.0 (OCH$_3$), 55.9 (OCH$_3$), 51.5 (C-4'), 47.0, 41.8 (C-2, C-6), 36.3, 36.1, 32.9, 32.1, 29.2, 24.0 (C-3, C-5, C-4, C-3', C-2', C-1'). HRESIMS m/z found 347.2073 calc. for C$_{18}$H$_{27}$O$_3$N$_4$: 347.2078.

4-(4-Azidobutyl)-1-[5-(hydroxymethyl)-2-methyl-3-furoyl]piperidine (40e)

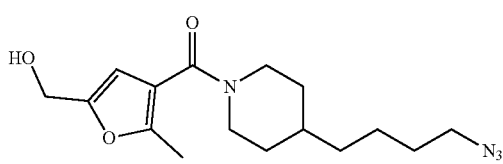 [SMILES: Cc1oc(CO)cc1C(=O)N1CCC(CCCCN=[N+]=[N-])CC1]

Same procedure as for the preparation of 40a starting with 37e (352.9 mg, 0.785 mmol). Yield: (216.3 mg, 0.675 mmol, 86%, MW: 320.393) as a pale yellow oil. IR (v cm$^{-1}$) 3369 (OH), 2091 (N$_3$), 1600 (C=O). $^1$H NMR (300 MHz, CDCl$_3$, δ ppm, J Hz) δ 6.20 (s, 1H, H-1''), 4.74-3.73 (m, 4H, —CH$_2$OH, H-2a, H-6a), 4.02 (t, 2H, J$_{4',3'}$=6.9, H-4'), 2.80 (br.s, 2H, H-2b, H-6b), 2.34 (s, 3H, Me), 1.74-1.71 (m, 2H, H-3a, H-5a), 1.63-1.56 (m, 1H, H-3'), 1.52-1.34 (m, 3H, H-4, H-2'), 1.31-1.24 (m, 2H, H-1'), 1.13-1.09 (m, 2H, H-3b, H-5b). $^{13}$C-NMR (75.4 MHz, CDCl$_3$, δ ppm) 165.1 (C=O), 153.0, 152.0, 116.7, 108.3, (C-arom.), 57.3 (—CH$_2$OH), 51.4 (C-4'), 42.7 (C-2, C-6), 36.2 (C-4), 35.9 (C-1'), 32.6 (C-3, C-5), 29.1 (C-3'), 23.9 (C-2'), 13.1 (CH$_3$). CIMS m/z 321 [100%, (M+H)$^+$]. HRCIMS m/z found 321.1931, calc. for C$_{16}$H$_{25}$O$_3$N$_4$: 321.1927.

4-(4-Aminobutyl)-1-benzoylpiperidine (41a≡21a)

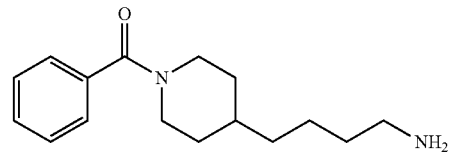 [SMILES: NCCCCC1CCN(C(=O)c2ccccc2)CC1]

Water (40 μL, 2.18 mmol) and triphenylphosphine (143 mg, 0.55 mmol) were added to a solution of compounds 40a (104.1 mg, 0.36 mmol) in THF (1.5 mL). The resulting mixture was heated at reflux for 6 to 8 h. The solvent was evaporated in vacuo and the residue was purified by FC (10/1/0.1 CH$_2$Cl$_2$/MeOH/NH$_4$OH). Yield: (91.1 mg, 0.35 mmol, 97%, MW: 260.381) as a pale yellow oil. The NMR data were in accordance to the previously described compound.

4-(4-Aminobutyl)-1-(thiophene-2-carbonyl)piperidine (41b≡21c)

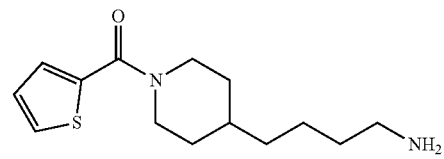

Same procedure as for the preparation of 41a starting with 40b. Yield: (92.2 mg, 0.346 mmol, 96%, MW: 266.403) as a pale yellow oil. IR (v cm$^{-1}$) 3364 (NH), 1604 (C=O). $^1$H-NMR (300 MHz, CDC$_3$, δ ppm, J Hz) δ 7.40 (dd, 1H, J$_{5'',4''}$=4.8, J$_{5'',3''}$=0.9, H-5''), 7.25 (dd, 1H, J$_{3'',4''}$=3.6, H-3''), 7.01 (dd, 1H, H-4''), 4.40 (m, 2H, H-2a, H-6a), 2.91 (m, 2H, H-2b, H-6b), 2.69 (t, 2H, J$_{4',3}$=5.7, H-4'), 1.75 (br d, 2H, H-3a, H-5a), 1.56-1.1 (m, 11H, H-4, H-3', H-2', H-1', NH$_2$, H-3b, H-5b). $^{13}$C-NMR (75.4 MHz, CDCl$_3$, δ ppm) 163.5 (C=O), 137.7 (C-2''), 128.5 (C-3''), 128.2 (C-5''), 126.7 (C-4''), 46.5 (C-6, C-2), 42.2 (C-4'), 36.3 (C-4), 36.3 (C-2'), 33.9 (C-3'), 32.6 (C-5, C-3), 24.0 (C-1'). CIMS m/z 266 [100%, (M+H)$^+$]. HRCIMS m/z found 267.1539, calc. for C$_{14}$H$_{23}$ON$_2$S: 267.1531. This compound is identical to 21c.

4-(4-Aminobutyl)-1-(2-furoyl)piperidine (41c≡21b)

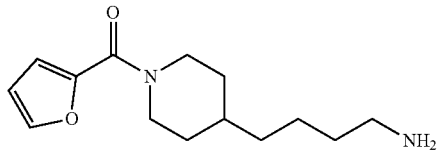

Same procedure as for the preparation of 41a starting with 40c. Yield: (79.3 mg, 0.317 mmol, 88%, MW: 250.342). IR (v cm$^{-1}$) 3359 (NH), 2927, 1612 (C=O). $^1$H-NMR (300 MHz, CDCl$_3$, δ ppm, J Hz) δ 7.43 (dd, 1H, $J_{5'',4''}$=1.8, $J_{5'',3''}$=0.9, H-5''), 6.88 (dd, 1H, $J_{3'',4''}$=3.3, H-3''), 6.42 (dd, 1H, H-4''), 4.45 (brs, 2H, H-2a, H-6a), 2.88 (brs, 2H, H-2b, H-6b), 2.66 (t, 2H, $J_{4',3'}$=6.6, H-4'), 1.94 (brs, 2H, NH$_2$), 1.73 (br d, 2H, H-3a, H-5a), 1.55-1.37 (m, 3H, H-4, H-3'), 1.35-1.09 (m, 6H, H-2', H-1', H-3b, H-5b). $^{13}$C-NMR (75.4 MHz, CDCl$_3$, δ ppm) 159.2 (C=O), 148.2 (C-2''), 143.5 (C-5''), 115.6 (C-3''), 111.1 (C-4''), 46.5 (C-6, C-2), 41.9 (C-4'), 36.3 (C-2'), 36.2 (C-4), 33.5 (C-3'), 32.6 (C-5, C-3), 23.9 (C-1'). CIMS m/z 251 [100%, (M+H)$^+$]. HRCIMS m/z found 251.1764, calc. for C$_{14}$H$_{23}$O$_2$N$_2$: 251.1760. This compound is identical to 21b.

4-(4-Aminobutyl)-N-(2,6-dimethoxybenzoyl)-piperidine (41d 21d)

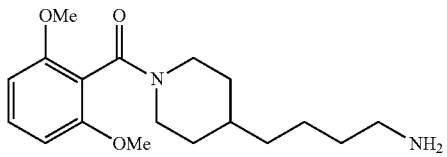 [SMILES: COc1cccc(OC)c1C(=O)N1CCC(CCCCN)CC1]

Same procedure as for the preparation of 41a starting with 40d. Yield: (89.9 mg, 0.28 mmol, 78%, MW: 320.433) as a pale yellow oil. $^1$H-NMR (300 MHz, CDCl$_3$, δ ppm, J Hz) δ 7.30 (t, 1H, $J_{H,H}$=8.3, H-arom.), 6.60 (d, 1H, H-arom.), 6.59 (d, 1H, H-arom.), 4.88-4.78 (m, 1H, H-6a or H-2a), 3.85 (s, 3H, OCH$_3$), 3.83 (s, 3H, OCH$_3$), 3.54-3.45 (m, 1H, H-6a or H-2a), 2.96 (td, 1H, $J_{H,H}$=12.9, $J_{H,H}$=2.6, H-6b or H-2b), 2.83-2.72 (m, 1H, H-6b or H-2b, H-4'), 1.87-1.07 (m, 11H, H-3, H-4, H-5, H-1', H-2', H-3'). $^{13}$C-NMR (75.4 MHz, CDCl$_3$, δ ppm) δ 165.2 (C=O), 156.8, 156.7, 130.0, 115.2, 104.0 (C-arom.), 56.0 (OCH$_3$), 55.9 (OCH$_3$), 47.1 (C-2, C-6), 42.2 (C-4'), 41.8 (C-2, C-6), 36.4, 36.3, 33.8, 32.0, 32.1, 24.0 (C-3, C-5, C-4, C-3', C-2', C-1'). HRESIMS m/z found 321.2168 calc. for C$_{18}$H$_{29}$O$_3$N$_2$: 321.2173.

4-(4-Aminobutyl)-1-(5-hydroxymethyl-2-methyl-3-furoyl)piperidine (41e)

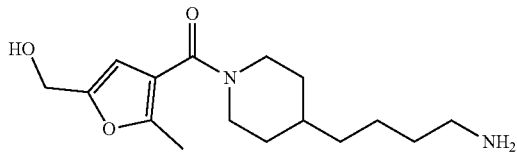 [SMILES: Cc1oc(CO)cc1C(=O)N1CCC(CCCCN)CC1]

Same procedure as for the preparation of 41a starting with 40e. Yield: (79.5 mg, 0.27 mmol, 75%, MW: 294.395). IR (v cm$^{-1}$) 3359 (OH, NH), 1600 (C=O). $^1$H NMR (300 MHz, CDCl$_3$, δ ppm, J Hz) δ 6.18 (s, 1H, H-1''), 4.52 (s, 2H, —CH$_2$OH), 3.97 (br. s, 2H, H-2a or H-6a), 2.90 (br. s, 2H, H-2a or H-6a), 2.67 (t, 2H, $J_{4',3'}$=6.9, H-4'), 2.33 (s, 3H, Me), 2.23 (br.s, 4H, NH$_2$, H-2b, H-6b), 1.72-1.69 (m, 2H, H-3a, H-5a), 1.50-1.37 (m, 3H, H-3', H-4), 1.35-1.24 (m, 4H, H-2', H-1'), 1.11-1.07 (m, 2H, H-3b, H-5b). $^{13}$C-NMR (75.4 MHz, CDC$_3$, δ ppm) 165.1 (C=O), 152.8, 152.4, 116.7, 108.1, (C-arom.), 57.0 (—CH$_2$OH), 47.7 (C-2, C-6), 42.0 (C-4'), 36.3 (C-4 or C-2), 36.2 (C-4 or C-2), 33.5 (C-3'), 32 (C-5, C-3), 24.0 (C-1'), 13.1 (CH$_3$). CIMS m/z 295 [100%, (M+H)$^+$]. HRCIMS m/z found 295.2024, calc. for C$_{16}$H$_{27}$O$_3$N$_2$: 295.2022.

Synthesis of 2,6-Difluoro Pyridine Derivatives

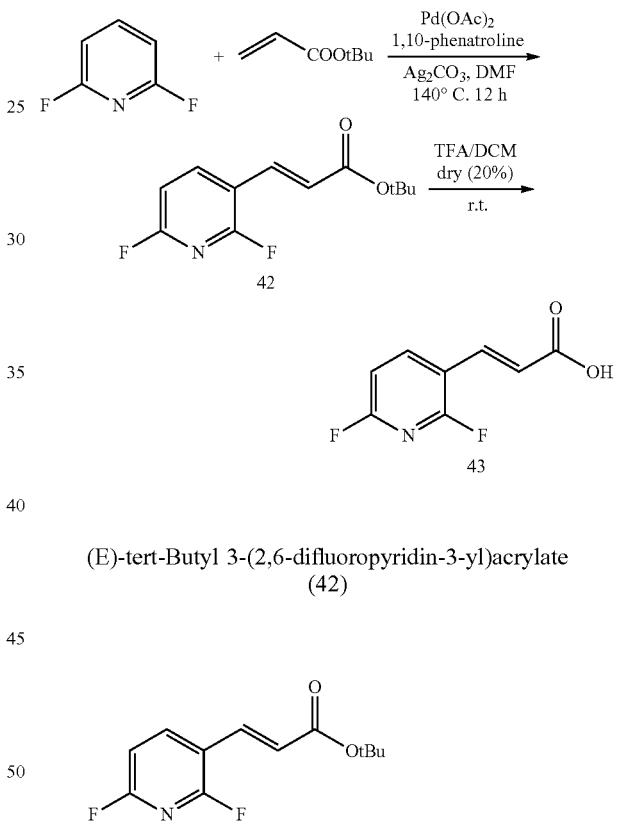

(E)-tert-Butyl 3-(2,6-difluoropyridin-3-yl)acrylate (42)

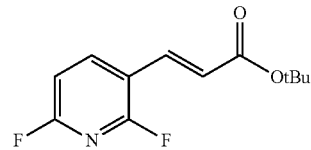 [SMILES: CC(C)(C)OC(=O)/C=C/c1ccc(F)nc1F]

To a 20 mL sealed tube, Pd(OAc)$_2$ (11.4 mg, 0.05 mmol), 1,10-phenanthroline (12 mg, 0.065 mmol), Ag$_2$CO$_3$ (69.6 mg, 0.25 mmol), tert-butylacrylate (75 μL, 0.5 mmol) and 2,6-difluoropyridine (0.73 mL, 8 mmol) and DMF (1 mL) were added. The tube was capped and stirred at 140° C. for 12 h. The reaction mixture was cooled to room temperature and diluted with EtOAc, filtered through a short pad of Cellite, washed with EtOAc and concentrated in vacuo. The residue was purified by FC (1/10 EtOAc/cyclohexane) to give 42 (53 mg, 0.22 mmol, 44%, MW: 241.238) as yellow solid. IR (v cm$^{-1}$) 1698 (C=O). $^1$H NMR (300 MHz, CDCl$_3$, δ ppm, J Hz) δ 8.01-7.98 (m, 1H, H-arom.), 7.57 (d, 1H, $J_{H,H}$=16.2, CH=CH), 6.87 (dd, 1H, $J_{H,H}$=8.4, $J_{H,H}$=3.3, H-arom.), 6.44 (d, 1H, CH=CH. $^{13}$C NMR (75.4

MHz, CDCl$_3$, δ ppm) δ 165.5 (C=O), 161.7 (dd, J$_{C-F}$=250.1, J$_{C-F}$=14.4, C—F), 159.3 (dd, J$_{C-F}$=252.5, J$_{C-F}$=14.4, C—F), 143.5 (dd, J$_{C-F}$=8.1, J$_{C-F}$=3.9, C-arom.), 133.3 (d, J$_{C-F}$=2.5, CH=CH), 124.6 (dd, J$_{C-F}$=5.7, J$_{C-F}$=2.3, CH=CH), 114.9 (dd, J$_{C-F}$=24.3, J$_{C-F}$=6.1, C-arom.), 1087.1 (dd, J$_{C-F}$=34.8, J$_{C-F}$=5.7, C-arom.), 81.4 (—C(CH$_3$)$_3$), 28.2 (—C(CH$_3$)$_3$). HRCIMS m/z obsd. 242.0988, calc. for C$_{12}$H$_{14}$O$_2$NF$_2$: 242.0993.

(E)-3-(2, 6-difluoropyridin-3-yl)acrylic acid (43)

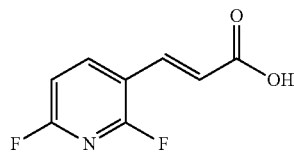 [SMILES: O=C(O)/C=C/c1ccc(F)nc1F]

Trifluoroacetic acid (2 mL) was added to 42 (263.9 mg, 1.09 mmol) dissolved in CH$_2$Cl$_2$ (8 mL) and the mixture was stirred at 20° C. for 3 h under Ar atmosphere. Solvent evaporation in vacuo gave 43 (201.8 mg, 1.09 mmol, quant. MW: 185.130) as a yellow solid. IR (vcm$^{-1}$) 2927 (OH), 1682 (C=O), 1464, 1218, 996, 732. $^1$H NMR (300 MHz, MeOD, δ ppm, J Hz) δ 8.36 (m, 1H, H-arom.), 7.67 (d, 1H, J$_{H,H}$=15.9, CH=CH), 7.05 (dd, 1H, J$_{H,H}$=8.4, J$_{H,H}$=2.7, H-arom.), 6.60 (d, 1H, CH=CH). $^{13}$C NMR (75.4 MHz, MeOD, δ ppm) δ 164.9 (C=O), 163.1 (dd, J$_{C-F}$=248.5, J$_{C-F}$=14.6, C—F), 160.4 (dd, J$_{C-F}$=250.1, J$_{C-F}$=14.5, C—F), 145.7 (dd, J$_{C-F}$=8.4, J$_{C-F}$=3.7, C-arom.), 135.5 (d, J$_{C-F}$=1.7, CH=CH), 123.8 (dd, J$_{C-F}$=5.1, J$_{C-F}$=2.1, CH=CH), 115.9 (dd, J$_{C-F}$=24.1, J$_{C-F}$=6.0, C-arom.), 108.3 (dd, J$_{C-F}$=35.2, J$_{C-F}$=5.7, C-arom.). HRCIMS m/z obsd. 186.0367, calc. for C$_8$H$_6$O$_2$NF$_2$: 186.0367.

General Procedure for the Synthesis of PER-201, PER-202, PER-203, MPM-09

Amide coupling reactions between carboxylic acid 43 and amines 41a-d and, were carried out using PyBOP and DIPEA as coupling agents giving in good yields the following difluorinated compounds: PER-201 (MW=427.496), PER-202 (MW=433.518), PER-203 (MW=417.457) and MPM-09 (MW=487.548), respectively.

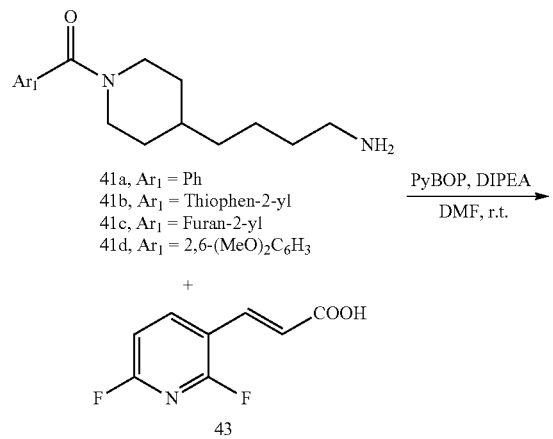

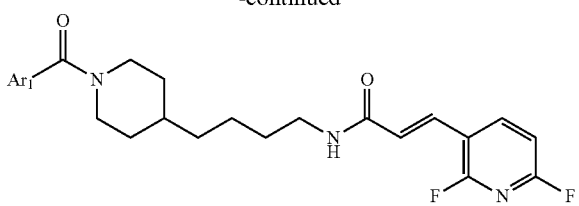

PER-201: Ar$_1$ = Ph (88%)
PER-202:, Ar$_1$ = Thiophen-2-yl (80%)
PER-203: Ar$_1$ = Furan-2-yl: (55%)
MPM-09: Ar$_1$ = 2,6-(MeO)$_2$C$_6$H$_3$ (74%)

(E)-N-(4-(1-benzoylpiperidin-4-yl)butyl)-3-(2,6-difluoropyridin-3-yl)acrylamide (PER-201)

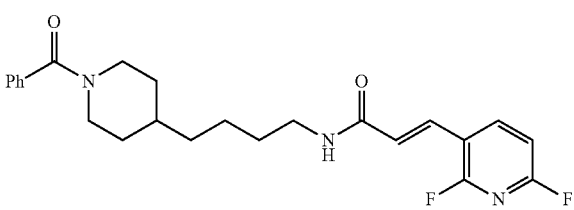 [SMILES: O=C(/C=C/c1ccc(F)nc1F)NCCCCC1CCN(C(=O)c2ccccc2)CC1]

To a solution of 41a (0.19 mmol) in DMF (1 mL), DIPEA (0.13 mL, 0.76 mmol), 43 (52.5 mg, 0.28 mmol) and PyBOP (151 mg, 0.28 mmol) were added. The reaction mixture was stirred at 20° C. for 15 h. The solvent was evaporated and the resulting crude was dissolved in EtOAc. The organic phase was washed with 1 M aqueous HCl, then with a saturated aqueous solution of NaHCO$_3$ and water. After drying (MgSO$_4$) the solvent was evaporated in vacuo and the residue purified by FC (6/1 diethyl ether/acetone) to give PER-201. Yield: (71.4 mg, 0.167 mmol, 88%, MW: 427.496), pale yellow oil. IR (v cm$^{-1}$) 3276 (NH), 1605 (C=O). $^1$H NMR (300 MHz, CDCl$_3$, δ ppm, J Hz) δ 7.98-7.90 (m, 1H, H-arom.), 7.54 (d, 1H, J$_{H,H}$=15.9, CH=CH), 7.51 (s, 5H, H-arom.), 6.85 (dd, 1H, J$_{H,H}$=8.1, J$_{H,H}$=2.7, H-arom.), 6.55 (d, 1H, CH=CH), 6.22 (brt, 1H, J$_{NH,4'}$=6.22, NH), 4.67 (brs, 1H, H-2a or H-6a), 3.70 (brs, 1H, H-2a or H-6a), 3.38-3.32 (m, 1H, H-4'), 2.97-2.74 (m, 2H, H-2b, H-6b), 1.79-0.99 (m, 11H, H-3, H-5, H-4, H-1', H-2', H-3'). $^{13}$C-NMR (75.4 MHz, CDCl$_3$, δ ppm) 170.5 (C=O), 165.2 (C=O), 161.2 (dd, J$_{C-F}$=250.2, J$_{C-F}$=15.0, C—F.), 159.2 (dd, J$_{C-F}$=252.4, J$_{C-F}$=14.6, C—F.), 144.6-144.4 (m, C-arom.), 136.4 (C-arom.), 131.1 (d, J$_{C-F}$=3.5, C-arom.), 129.6 (CH=CH), 128.6 (C-arom.), 126.9 (C-arom.), 125.6 (d, J$_{C-F}$=7.6, CH=CH), 115.2 (dd, J$_{C-F}$=23.4, J$_{C-F}$=6.6, C-arom.), 106.7 (dd, J$_{C-F}$=34.3, J$_{C-F}$=6.2, C-arom.), 48.2, 42.7 (C-2, C-6), 39.9 (C-4'), 36.2, 36.1, 33.0, 32.0, 29.9, 24.0 (C-3', C-2', C-4, C-1', C-3, C-5). HRLSIMS m/z found 450.1971, calc. for C$_{24}$H$_{27}$O$_2$N$_3$F$_2$Na: 450.1969.

(E)-3-(2,6-difluoropyridin-3-yl)-N-4-(1-(thiophene-2-carbonyl)piperidin-4-yl)butyl) acrylamide (PER-202)

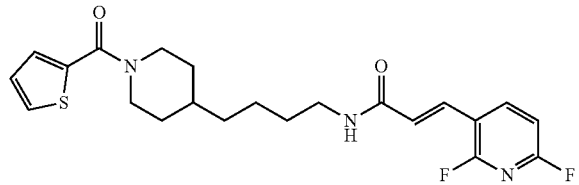

Same procedure as that used for the preparation of PER-201 starting with 41b. Yield: (65.9 mg, 0.152 mmol, 80%, MW: 433.518) as a pale yellow oil. IR (v cm$^{-1}$) 3276 (NH), 1602 (C=O). $^1$H NMR (300 MHz, CDCl$_3$, δ ppm, J Hz) δ 8.00-7.91 (m, 1H, H-arom.), 7.55 (d, 1H, $J_{H,H}$=15.6, CH=CH), 7.41 (dd, 1H, $J_{H,H}$=5.1, $J_{H,H}$=1.2, H-arom.), 7.25 (dd, 1H, $J_{H,H}$=4.2, $J_{H,H}$=1.8, H-arom.), 7.02 (dd, 1H, $J_{H,H}$=5.0, $J_{H,H}$=3.7, H-arom.), 6.85 (dd, 1H, $J_{H,H}$=8.1, $J_{H,H}$=3.0, H-arom.), 6.60 (d, 1H, CH=CH), 6.22 (brt, 1H, $J_{NH,4'}$=5.90, NH), 4.40 (brs, 2H, H-2a, H-6a), 3.41-3.34 (m, 1H, H-4'), 2.91 (brs, 2H, H-2b, H-6b), 1.77-1.73 (m, 2H, H-3a, H-5a), 1.59-1.52 (m, 3H, H-3', H-4), 1.38-1.23 (m, 4H, H-2', H-1'), 1.21-1.11 (m, 2H, H-3b, H-5b). $^{13}$C-NMR (75.4 MHz, CDCl$_3$, δ ppm) 165.2 (C=O), 163.6 (C=O), 161.2 (dd, $J_{C-F}$=251.2, $J_{C-F}$=16.0, C—F), 159.2 (dd, $J_{C-F}$=251.3, $J_{C-F}$=14.9, C—F), 144.5 (dd, $J_{C-F}$=8.1, $J_{C-F}$=4.4, C-arom.), 137.6 (C-arom.), 131.3 (d, $J_{C-F}$=3.9, CH=CH), 128.5 (C-arom.), 128.3 (C-arom.), 126.7 (C-arom.), 125.6 (dd, $J_{C-F}$=8, $J_{C-F}$=2.2, CH=CH), 115.2 (dd, $J_{C-F}$=24, $J_{C-F}$=6.2, C-arom.), 107.0 (dd, $J_{C-F}$=34.6, $J_{C-F}$=5.8, C-arom.), 46.5 (C-2, C-6), 39.9 (C-4'), 36.2, 36.1, 32.6, 29.9, 24.1 (C-3', C-2', C-4, C-1', C-3, C-5). HRLSIMS m/z found 456.1538, calc. for C$_{22}$H$_{25}$O$_2$N$_3$F$_2$NaS: 456.1533.

(E)-3-(2,6-difluoropyridin-3-yl)-N-4-(1-(furan-2-carbonyl)piperidin-4-yl)butyl) acrylamide (PER-203)

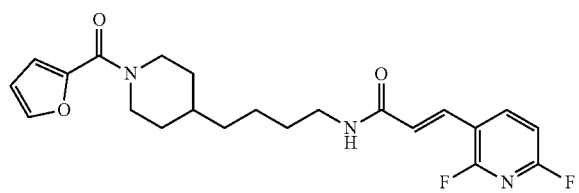 [SMILES: O=C(/C=C/c1ccc(F)nc1F)NCCCCC1CCN(C(=O)c2ccco2)CC1]

Same procedure as that used for the preparation of PER-201 starting with 41c. Yield: (43.4 mg, 0.104 mmol, 55%, MW: 417.457) as a pale yellow oil. IR (v cm$^{-1}$) 3272 (NH), 1605 (C=O). 1H NMR (300 MHz, CDCl$_3$, δ ppm, J Hz) δ 8.02-7.93 (m, 1H, H-arom.), 7.56 (d, 1H, $J_{H,H}$=15.9, CH=CH), 7.46 (dd, 1H, $J_{H,H}$=1.8, $J_{H,H}$=0.9, H-arom.), 6.92 (dd, 1H, $J_{H,H}$=3.3, $J_{H,H}$=0.6, H-arom.), 6.86 (dd, 1H, $J_{H,H}$=10.2, $J_{H,H}$=2.1, H-arom.), 6.58 (d, 1H, CH=CH), 6.45 (dd, 1H, $J_{H,H}$=3.3, $J_{H,H}$=1.8, H-arom.), 6.23 (brt, 1H, $J_{NH,4'}$=1.6, NH), 4.48 (brs, 2H, H-2a, H-6a), 3.42-3.35 (m, 1H, H-4'), 2.91 (brs, 2H, H-2b, H-6b), 1.78-1.74, 1.59-1.50, 1.39-1.12 (m, H-3, H-5, H-4, H-1', H-2', H-3'). $^{13}$C-NMR (75.4 MHz, CDCl$_3$, δ ppm) 165.4 (C=O), 161.2 (dd, $J_{C-F}$=249.9, $J_{C-F}$=15.2, C—F.), 159.3 (dd, $J_{C-F}$=253.0, $J_{C-F}$=15.2, C—F.), 159.4 (C=O), 144.6-144.4 (m, C-arom.), 143.7 (C-arom.), 132.5-132.1 (m, C-arom.), 131.4 (brs, CH=CH), 128.9 (d, $J_{C-F}$=12.4, C-arom.), 125.4-125.3 (m, CH=CH), 115.9 (C-arom.), 111.3 (C-arom.), 107.0 (d, $J_{C-F}$=40.6), 46.6 (C-2, C-6), 40.0 (C-4'), 36.2, 36.1, 32.6, 29.9, 24.1 (C-1', C-2', C-3', C-4, C-3, C-5). HRLSIMS m/z found 440.1749, calc. for C$_{22}$H$_{25}$O$_3$N$_3$F$_2$Na: 440.1762.

(E)-3-(2,6-difluoropyridin-3-yl)-N-(4-1-(2,6-dimethoxybenzoyl)piperidin-4-yl)butyl) acrylamide (MPM-09)

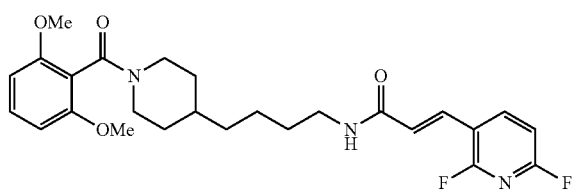 [SMILES: COc1cccc(OC)c1C(=O)N1CCC(CCCCNC(=O)/C=C/c2ccc(F)nc2F)CC1]

Same procedure as that used for the preparation of PER-201 starting with 41d. Yield: (68.3 mg, 0.14 mmol, 74%, MW: 487.548) as a pale yellow oil. $^1$H NMR (300 MHz, CDC$_3$, δ ppm, J Hz) 7.94 (q, 1 $J_{H,H}$=7.8, H-arom.), 7.54 (d, 1 $J_{H,H}$=15.8, CH=CH), 7.22 (t, 1H, $J_{H,H}$=8.4, H-arom.), 6.84 (dd, 1H, $J_{H,H}$=8.1, $J_{H,H}$=2.9, H-arom.), 6.56-6.51 (m, 3H, CH=CH, H-arom.), 6.08 (brt, 1H, $J_{NH,4'}$=5.0, NH), 4.79-4.74 (m, 1H, H-2a or H-6a), 3.78 (s, 3H, OCH$_3$), 3.76 (s, 3H, OCH$_3$), 3.46-3.41 (m, 1H, H-2a or H-6a), 3.35 (q., 1 $J_{H,H}$=6.8, H-4'), 2.90 (td, 1H, $J_{H,H}$=13.0, $J_{H,H}$=2.5, H-6b or H-2b), 2.70 (td, 1H, $J_{H,H}$=13.0, $J_{H,H}$=3.1, H-6b or H-2b), 2.17-0.85 (m, 11H, H-3, H-5, H-4, H-1', H-2', H-3'). $^{13}$C-NMR (75.4 MHz, CDCl$_3$, δ ppm) δ 165.3 (C=O), 165.2 (C=O), 161.2 (dd, $J_{C-F}$=245.8, $J_{C-F}$=13.5, C—F), 159.3 (dd, $J_{C-F}$=249.1, $J_{C-F}$=13.5, C—F), 156.8 (C-arom.), 156.7 (C-arom.), 144.5-144.3 (m, C-arom.), 131.1 (d, $J_{C-F}$=3.7, CH=CH), 130. (C-arom.), 125.6 (d, $J_{C-F}$=7.5, $J_{C-F}$=2.3, C-arom.), 115.1 (C-arom.), 107.2 (d, $J_{C-F}$=6.1, C-arom.), 106.7 (d, $J_{C-F}$=6.0, C-arom.), 104.1 (CH=CH), 56.0 (OCH$_3$), 55.9 (OCH$_3$), 47.1 (C-2 or C-6), 41.8 (C-2 or C-6), 39.9 (C-4'), 36.3, 36.2, 32.9, 32.1, 29.9, 24.1 (C-3', C-2', C-4, C-1', C-3, C-5).

Synthesis of 2-Fluoro Pyridine Derivatives

This compound was obtained through Heck reaction starting from commercial 2-fluoro-2-iodopyridine followed by acidic deprotection.

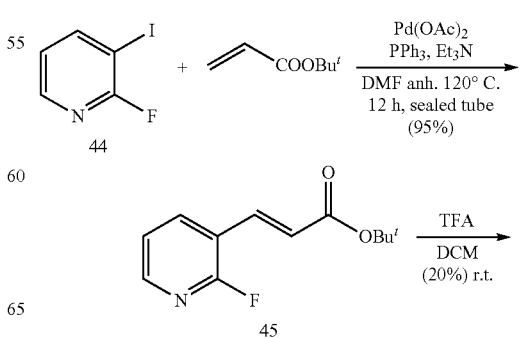

-continued

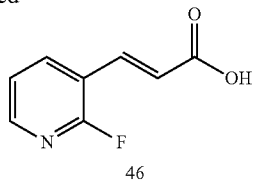

(E)-tert-Butyl 3-(2-fluoropyridin-3-yl)acrylate (45)

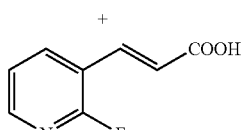

Tert-butylacrylate (1.3 mL, 8.7 mmol), Pd(OAc)$_2$ (19.53 mg, 0.09 mmol), PPh (46 mg, 0.17 mmol), EtN$_3$ (0.62 mL, 4.35 mmol) were added under argon atmosphere to a solution of 2-fluoro-3-iodo-pyridine (44, 200 mg, 0.87 mmol) in dry DMF (2.2 mL) in a 20 mL sealed tube. The reaction mixture was stirred at 120° C. for 18 h. Water (20 mL) was then added and the aqueous layer was extracted with EtOAc (20 mL, 3 times). The combined organic phases were dried, filtered and concentrated in vacuo. The residue was purified by FC (1/8 EtOAc/cyclohexane) to give 45 Yield: (185.2 mg, 0.83 mmol, 95%, MW: 223.247) as a white solid. $^1$H NMR (300 MHz, CDCl$_3$, δ ppm, J Hz) δ 8.19 (br. d, 1H, $J_{H,H}$=4.8, H-arom.), 7.91 (m 1H, H-arom.), 7.60 (d, 1H, $J_{H,H}$=16.2, CH=CH), 7.22 (m 1H, H-arom.), 6.51 (d, 1H, CH=CH), 1.53 (s, 9H, —C(CH$_3$)$_3$). $^{13}$C-NMR (75.4 MHz, CDCl$_3$, δ ppm) 165.5 (C=O), 161.2 (d, $J_{C-F}$=244.5, C—F.), 148.2 (d, $J_{C-F}$=15.2, C-arom.), 139.2 (d, $J_{C-F}$=3.9, C-arom.), 134.5 (d, $J_{C-F}$=2.9, CH=CH), 125.0 (d, $J_{C-F}$=5.9, CH=CH), 121.8 (d, $J_{C-F}$=4.4, C-arom.), 117.9 (d, $J_{C-F}$=26.8, C-arom.), 81.1 (—C(CH$_3$)$_3$), 28.1 (—C(CH$_3$)$_3$). HRESIMS m/z obsd. 224.1077, calc. for C$_{12}$H$_{15}$O$_2$NF: 224.1081.

(E)-3-(2-Fluoropyridin-3-yl)acrylic acid (46)

Trifluoroacetic acid (1.3 mL) was added to a solution of 45 (160 mg, 0.72 mmol) in dry CH$_2$Cl$_2$ (5.2 mL) and stirred at r.t. for 2.5 h. The reaction mixture was then concentrated to dryness to give 46 (119.8 mg, 0.72 mmol, quant.) as a white solid, that was used without purification in the next step.

General procedure for the synthesis of MPM-07, MPM-08 and VAL-22-2. Strategy 1 Amide coupling reactions between carboxylic acid 46 and amines 41a, 41b and 41d and, were carried out using PyBOP and DIPEA as coupling agents giving in good yields the following fluorinated compounds: VAL-22-2 (MW: 409.505), MPM-07 (MW: 415.527) and MPM-08 (MW: 469.557)

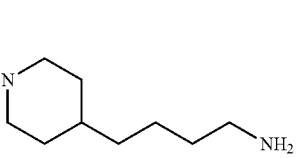

41a, R = Ph
41b, R = Tioph
41d, R = 2,6-diOMe-Ph

PyBOP, DIPEA
DMF, r.t.

+

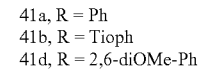

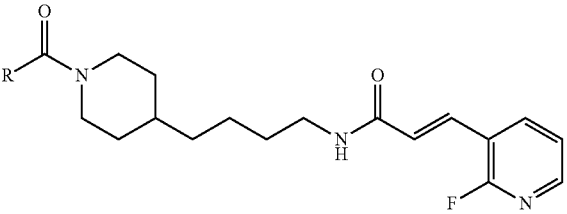

(VAL22-2) 47a, R = Ph (84%)
(MPM-07) 47b, R = Tioph: (80%)
(MPM-08) 47d, R = 2,6-diOMe-Ph: (45%)

(E)-N-(4-(1-benzoylpiperidin-4-yl)butyl)-3-(2-fluo-ropyridin-3-yl)acrylamide (VAL22-2))

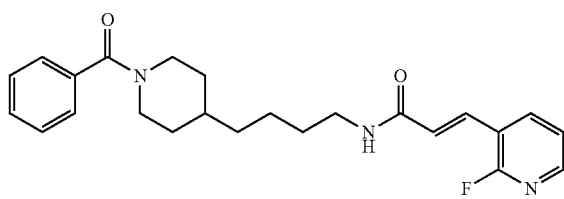 [SMILES: O=C(/C=C/c1cccnc1F)NCCCCC1CCN(C(=O)c2ccccc2)CC1]

To a solution of 41a (0.15 mmol) in DMF (0.8 mL), DIPEA (0.10 mL, 0.59 mmol), 46 (37.5 mg, 0.22 mmol) and PyBOP (120 mg, 0.22 mmol) were added. The reaction mixture was stirred at 20° C. for 19 h. The solvent was evaporated in vacuo and the resulting crude product was dissolved in EtOAc. The organic phase was washed with 1M aqueous HCl, then with a saturated aqueous solution of NaHCO$_3$ and water. After drying (MgSO$_4$), the solvent was evaporated in vacuo and the residue purified by FC (5/1 CH$_2$Cl$_2$/acetone). Yield: (51.6 mg, 0.126 mmol, 84%) as a white solid. $^1$H NMR (300 MHz, CDCl$_3$, δ ppm, J Hz) δ 8.16 (m, 1H, H-arom.), 7.79 (m, 1H, H-arom.), 7.55 (d, 1H, $J_{H,H}$=15.9, CH=CH), 7.36 (m, 5H, H-arom.), 7.19 (m, 1H, H-arom.), 6.62 (d, 1H, CH=CH), 6.34 (brt, 1H, $J_{NH,4'}$=5.4, NH), 4.65 (m, 1H, H-2a or H-6a), 3.68 (m, 1H, H-2a or H-6a), 3.34 (m, 1H, H-4'), 2.94 (m, 1H, H-6b or H-2b), 2.72 (m, 1H, H-6b or H-2b), 1.90-1.26 (m, 11H, H-3, H-5, H-4, H-1', H-2', H-3'). $^{13}$C-NMR (75.4 MHz, CDCl$_3$, δ ppm) δ 170.4 (C=O), 165.3 (C=O), 162.9 (d, $J_{C-F}$=244.3, C—F), 147.6 (d, $J_{C-F}$=15.4, C-arom.), 140.4 (d, $J_{C-F}$=4.2, C-arom.), 136.4 (C-arom.), 132.3 (d, $J_{C-F}$=4.1, CH=CH), 129.5 (C-arom.), 128.5 (C-arom.), 126.8 (C-arom.), 126.1 (d, $J_{C-F}$=8.0, CH=CH.), 121.9 (d, $J_{C-F}$=4.4, C-arom.), 118.3 (d, $J_{C-F}$=26.4, C-arom.), 46.9 (C-2 or C-6), 42.1 (C-2 or C-6), 39.8 (C-4'), 36.1, 36.0, 33.0, 31.9, 29.8, 24.0 (C-3', C-2', C-4, C-1', C-3, C-5). HRMS (ESI) m/z found 432.22054 for [M+Na]$^+$, calc. for $C_{24}H_{28}O_2N_3FNa$: 432.2054.

(E)-3-(2-fluoropyridin-3-yl)-N-4-(1-(thiophene-2-carbonyl)piperidin-4-yl)butyl) acrylamide (MPM-07)

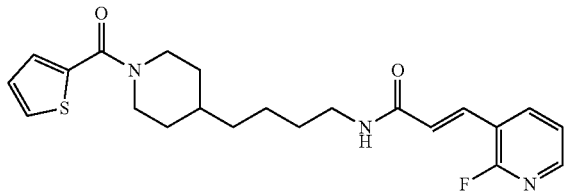 [SMILES: O=C(/C=C/c1cccnc1F)NCCCCC1CCN(C(=O)c2cccs2)CC1]

Same procedure as that used for the preparation of VAL22-2 starting from 41b. Yield: (49.03 mg, 0.118 mmol, 79%, MW: 415.527) as a pale yellow oil. $^1$H NMR (300 MHz, CDCl$_3$, δ ppm, J Hz) δ 8.16-8.14 (m, 1H, H-arom.), 7.86-7.82 (m, 1H, H-arom.), 7.57 (d, 1H, $J_{H,H}$=15.8, CH=CH), 7.41 (dd, 1 $J_{H,H}$=5.0, $J_{H,H}$=1.0, H-arom.), 7.26-7.19 (m, 2H, H-arom.), 7.02 (dd, 1 $J_{H,H}$=5.0, $J_{H,H}$=3.7, H-arom.), 6.62 (d, 1H, CH=CH), 6.08 (brt, 1H, $J_{NH,4'}$=5.5, NH), 4.40 (brs, 2H, H-2a, H-6a), 3.38 (q., 1H, $J_{H,H}$=6.8, H-4'), 3.01-2.79 (m, 2H, H-2b, H-6b), 1.82-1.73 (m, 2H, H-3a, H-5a), 1.61-1.52 (m, 3H, H-3', H-4), 1.43-1.11 (m, 6H, H-2', H-1', H-3b, H-5b). $^{13}$C-NMR (75.4 MHz, CDCl$_3$, δ ppm) δ 165.2 (C=O), 163.5 (C=O), 161.3 (dd, $J_{C-F}$=229, C—F), 147.5 (dd, $J_{C-F}$=15.3, C-arom.), 140.4 (dd, $J_{C-F}$=4.3, C-arom.), 137.5 (C-arom.), 132.5 (d, $J_{C-F}$=4.5, CH=CH), 128.4 (C-arom.), 128.2 (C-arom.), 126.6 (C-arom.), 126.0 (dd, $J_{C-F}$=8.4, CH=CH), 121.8 (dd, $J_{C-F}$=4.4, C-arom.), 118.2 (dd, $J_{C-F}$=26.5, C-arom.), 45.6 (C-2, C-6), 39.8 (C-4'), 36.1, 36.0, 32.5, 30.3, 30.0, 23.9 (C-3', C-2', C-4, C-1', C-3, C-5). HRMS (ESI) m/z found 438.1617, calc. for $C_{22}H_{26}O_2N_{32}NaS$: 438.1622.

(E)-N-(4-1-(2,6-dimethoxybenzoyl)piperidin-4-yl)butyl)-3-(2-fluoropyridin-3-yl)acrylamide (MPM-08)

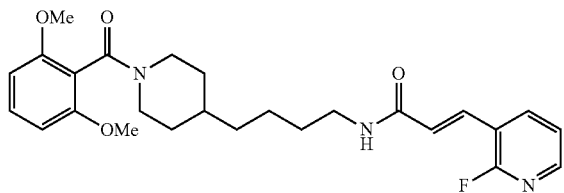 [SMILES: COc1cccc(OC)c1C(=O)N1CCC(CCCCNC(=O)/C=C/c2cccnc2F)CC1]

Same procedure as that used for the preparation of VAL-22-2 starting from 41d. Yield: (32.9 mg, 0.07 mmol, 45%, MW: 469.557) as a pale yellow oil. $^1$H NMR (300 MHz, CDCl$_3$, δ ppm, J Hz) δ 8.16-8.14 (m, 1H, H-arom.), 7.89-7.81 (m, 1H, H-arom.), 7.56 (d, 1 $J_{H,H}$=15.8, CH=CH), 7.25-7.18 (m, 2H, H-arom.), 6.60 (d, 1H, CH=CH), 6.54 (d, 1 $J_{H,H}$=8.4, H-arom.), 6.53 (d, 1H, $J_{H,H}$=8.4, H-arom.), 6.02 (brt, 1H, $J_{NH,4'}$=5.6, NH), 4.81-4.73 (m, 1H, H-2a or H-6a), 3.78 (s, 3H, OCH$_3$), 3.77 (s, 3H, OCH$_3$), 3.48-3.40 (m, 1H, H-2a or H-6a), 3.36 (q., 1H, $J_{H,H}$=6.9, H-4'), 2.90 (td, 1H, $J_{H,H}$=13.1, $J_{H,H}$=2.6, H-6b or H-2b), 2.73 (td, 1H, $J_{H,H}$=12.8, $J_{H,H}$=2.9, H-6b or H-2b), 1.73-1.03 (m, 11H, H-3, H-5, H-4, H-1', H-2', H-3'). $^{13}$C-NMR (75.4 MHz, CDCl$_3$, δ ppm) δ 165.2 (C=O), 161.2 (d, $J_{C-F}$=244.3, C—F), 156.6 (C-arom.), 156.5 (C-arom.), 147.5 (d, $J_{C-F}$=15.4, C-arom.), 140.3 (dd, $J_{C-F}$=4.1, C-arom.), 132.3 (d, $J_{C-F}$=4.1, CH=CH), 130.0 (C-arom.), 126.1 (d, $J_{C-F}$=8, C-arom.), 121.8 (d, $J_{C-F}$=4.4, C-arom.), 118.2 (d, $J_{C-F}$=26.4, C-arom.), 115.0 (C-arom.), 103.9 (CH=CH), 55.8 (OCH$_3$), 55.7 (OCH$_3$), 46.9 (C-2 or C-6), 41.7 (C-2 or C-6), 39.8 (C-4'), 36.2, 36.1, 32.8, 31.9, 29.8, 24.0 (C-3', C-2', C-4, C-1', C-3, C-5). HRMS (ESI) m/z found 470.2442, calc. for $C_{26}H_{33}O_4N_3F$: 470.2450.

General Procedure for the Synthesis of MPM-10, MPM-11, MPM-12, MPM-13 and MPM-14. Strategy 2

For the synthesis of the above derivatives another strategy was followed as outlined in the scheme. Reaction of amine 8 with 2-fluoroacrylic acid 46 under standard amide coupling conditions afforded Boc-protected derivative 48 in 90% yield. Acidic deprotection, quantitatively gave free amine 49 which was coupled with hydroxymethyl carboxylic acids 39 and 50 furnishing derivatives MPM-10 (MW: 443.519) and MPM-12 (MW: 499.583), respectively. Dess-Martin oxidation gave, respectively, the corresponding carbaldehydes MPM-11 (MW: 441.503), and MPM-13 (MW: 497.567), in excellent yields. On its side, reaction of pyrrole carboxylic acid 55 with 49, under the same conditions, gave derivative MPM-14 (MW: 482.600) in 76% yield.

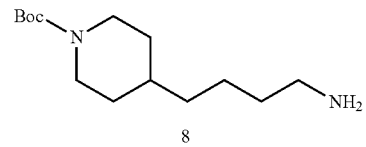

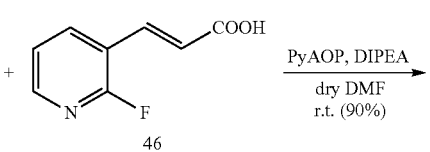

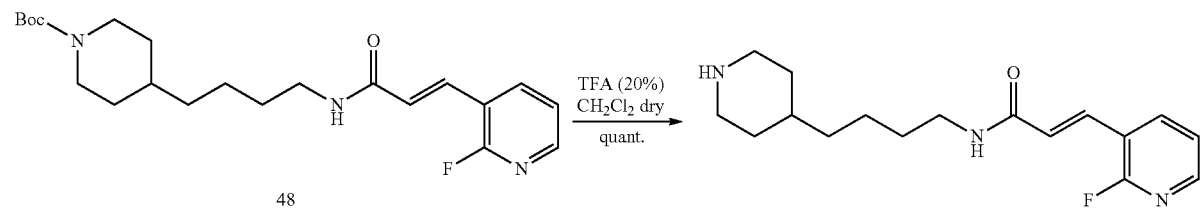

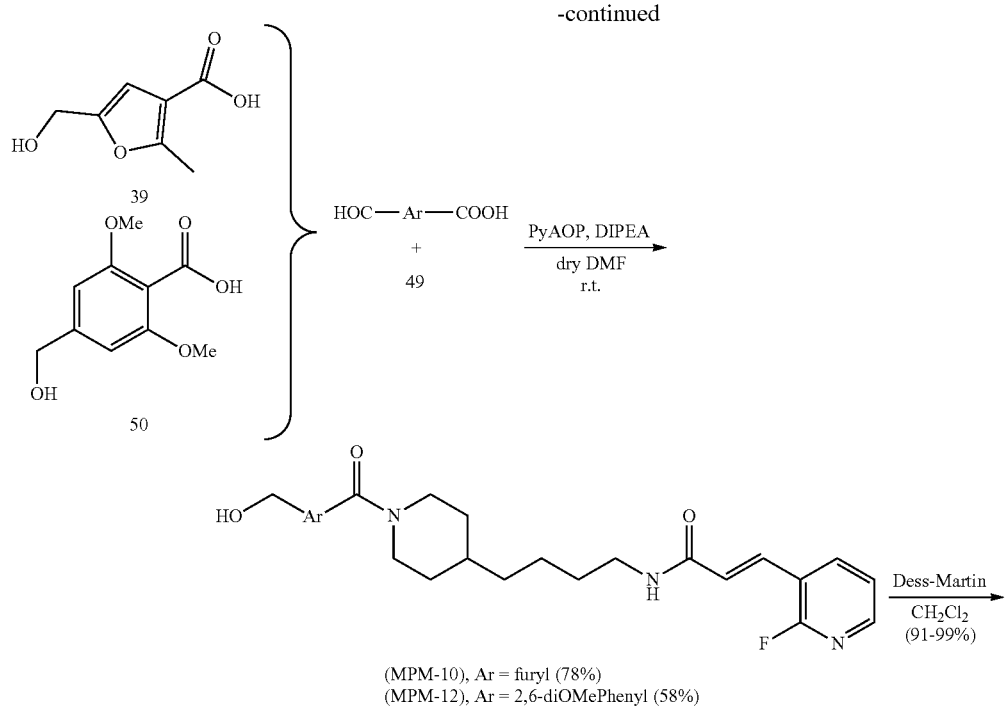

(MPM-10), Ar = furyl (78%)
(MPM-12), Ar = 2,6-diOMePhenyl (58%)

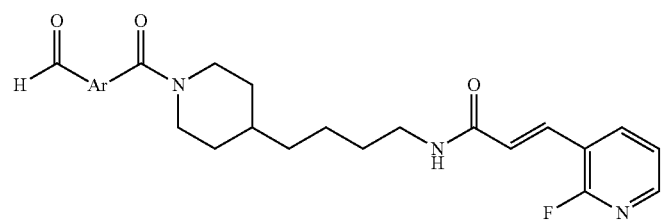

(MPM-11), Ar = furyl (91%)
(MPM-13), Ar = 2,6-diOMePhenyl (99%)

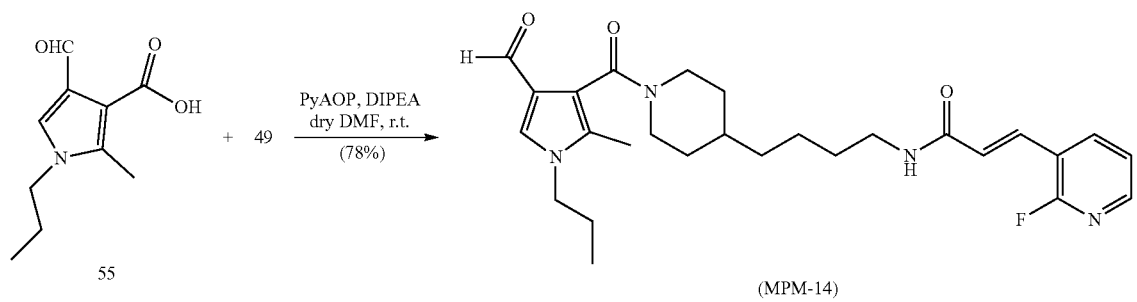

(MPM-14)

Hydroxymethyl benzoic acid 50 was prepared according to the reported procedure [Ishii, H.; Sugiura, T.; Akiyama, Y.; Ichikawa, Y.; Watanabe, T.; Murakami, Y. *Chem. Pharm. Bull.* 1990, 38, 2118]. Pyrrole carboxylic acid 55 was prepared by basic hydrolysis of the known ethyl ester [Garcia Gonzalez, F.; Fernandez-Bolanos, J.; Martin Jimenez de la Plata, G.; Lopez Partida, N.; Robina Ramirez, I. *An. Quim.* 1978, 74, 1281-1284] in 88% yield.

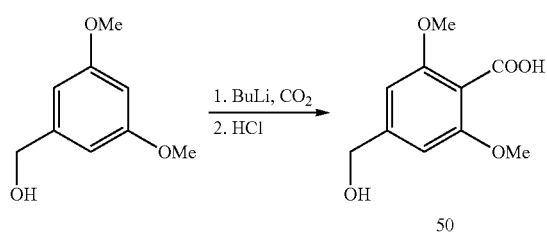

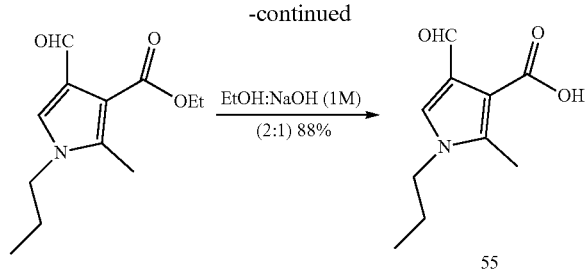

(E)-3-(2-Fluoropyridin-3-yl)-N-(tert-butyloxycarbonylpiperidin-4-yl)butyl)acrylamide (48)

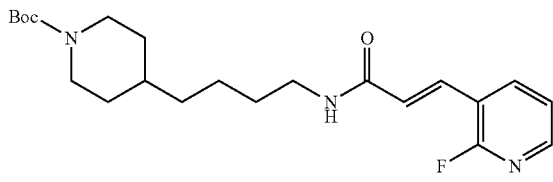 [SMILES: CC(C)(C)OC(=O)N1CCC(CCCCNC(=O)/C=C/c2cccnc2F)CC1]

To a solution of amine 8 (288 mg, 1.12 mmol) in dry DMF (15 ml) is dissolved, DIPEA (0.8 mL, 4.49 mmol), 2-fluroacrylic acid 46 (225 mg, 1.348 mmol) and PyBOP (716 mg, 1.35 mmol) are added. The reaction mixture is left to stand at r.t. for 5 h and then concentrated to dryness. The obtained crude product was dissolved in AcOEt (60 mL) and washed successively with HCl (1M) (3×15 mL), NaHCO$_3$ (3×15 ml) and H$_2$O (3×15 mL). The organic phase is dried over Na$_2$SO$_4$, filtered and concentrated to dryness. Purification by column chromatography on silica gel (ether:acetone, 20:1) gave 48. Yield: (405.5 mg, 1.00 mmol, 90%, MW: 405.514) as a colourless oil. $^1$H NMR (300 MHz, CDC$_3$, δ ppm, J Hz) δ 8.17-8.15 (m, 1H, H-arom.), 7.90-7.83 (m, 1H, H-arom.), 7.58 (d, 1 $J_{H,H}$=15.8, CH=CH), 7.26-7.21 (m, 1H, H-arom.), 6.61 (d, 1H, CH=CH), 5.88 (brt, 1H, $J_{NH,4'}$=5.9, NH), 4.10-4.03 (m, 2H, H-2a, H-6a), 3.39 (q, 1 $J_{H,H}$=6.8, H-4'), 2.65 (td, 2H, $J_{H,H}$=13.1, $J_{H,H}$=2.5, H-2b, H-6b), 1.65-0.98 (m, 11H, H-3, H-5, H-4, H-1', H-2', H-3'), 1.44 (s, 9H, —C(CH$_3$)$_3$). HRESIMS m/z found 428.2315, calc. for C$_{22}$H$_{32}$O$_3$N$_3$FNa: 428.2320.

(E)-3-(2-fluoropyridin-3-yl)-N-(4-1-(5-(hydroxymethyl-2-methylfuro-3-yl)piperidin-4-yl)butyl)acrylamide (MPM-10)

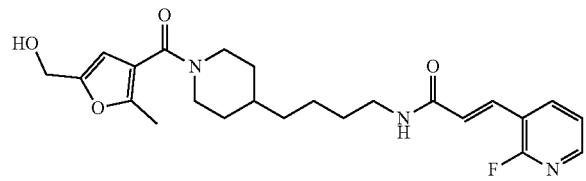 [SMILES: Cc1oc(CO)cc1C(=O)N1CCC(CCCCNC(=O)/C=C/c2cccnc2F)CC1]

Compound 48 (265 mg, 0.654 mmol) is dissolved in a solution of 20% TFA in CH$_2$Cl$_2$ (6 mL) at 0° C. and left to stand at this temperature for 1 h, and then concentrated to dryness giving 49 in quantitavily yield. To a solution of the crude product 49 in dry DMF (7 mL), DIPEA (685 □l, 3.921 mmol) is added and stirred for 5 min. Then the carboxylic acid 39 (133 mg, 0.850 mmol) and PyBOP (590 mg, 1.111 mmol) are added. The reaction mixture was allowed to stand at r.t. under nitrogen for 14 h and then concentrated to dryness. The residue was dissolved in AcOEt (90 mL) and washed with HCl (1M) (3×20 mL), saturated NaHCO$_3$ (3×20 mL) and NaCl aqueous solution (3×20 mL). The organic phase is dried over Na$_2$SO$_4$, filtered and concentrated to dryness. Purification by column chromatography of the residue on silica gel (CH$_2$Cl$_2$:MeOH, 30:1→20:1→10:1) afforded MPMN-10 (226.3 mg, 0.510 mmol, 78%, MW: 443.519) as a white solid. IR (v cm$^{-1}$) 3280 (NH, OH), 1597 (C=O). $^1$H NMR (300 MHz, CDCl$_3$, δ ppm, J Hz) δ 8.16-8.14 (m, 1H, H-arom.), 7.89-7.83 (m, 1H, H-arom.), 7.56 (d, 1 $J_{H,H}$=15.8, CH=CH), 7.24-7.19 (m, 1H, H-arom.), 6.62 (d, 1H, CH=CH), 6.20 (s, 1H, H-arom.), 6.11 (brt, 1H, $J_{NH,4'}$=5.6, NH), 4.66-4.41 (m, 3H, —CH$_2$OH, H-2a or H-6a), 3.92 (brs, 1H, H-2a or H-6a), 3.24 (q, $J_{H,H}$=6.8, H-4'), 2.84, (brs, 2H, H-2b, H-6b), 1.83-1.09 (m, 11H, H-3, H-5, H-4, H-1', H-2', H-3'). $^{13}$C-NMR (75.4 MHz, CDCl$_3$, δ ppm) δ 165.4 (C=O), 165.1 (C=O), 161.4 (d, $J_{C-F}$=243.0, C—F), 153.0 (C-arom.), 152.1 (C-arom.), 147.7 (d, $J_{C-F}$=15.3, C-arom.), 140.6 (d, $J_{C-F}$=4.3, C-arom.), 132.6 (d, $J_{C-F}$=5.1, CH=CH), 126.2 (d, $J_{C-F}$=8.3, CH=CH), 122.0 (d, $J_{C-F}$=4.3, C-arom.), 118.3 (d, $J_{C-F}$=26.8, C-arom.), 116.8 (C-arom.), 108.3 (C-arom.), 57.3 (CH$_2$OH), 48.0, 42.3 (C-2, C-6), 39.9 (C-4'), 36.2, 36.1, 32.9, 29.9, 24.1 (C-1', C-2', C-3', C-4, C-3, C-5), 13.1 (CH$_3$). HRESIMS m/z found 466.2114, calc. for C$_{24}$H$_{30}$O$_4$N$_3$FNa: 466.2113.

(E)-3-(2-fluoropyridin-3-yl)-N-(4-(1-(4-(hydroxymethyl)-2,6-dimethoxybenzoyl))piperidin-4-yl)butyl)acrylamide (MPM-12)

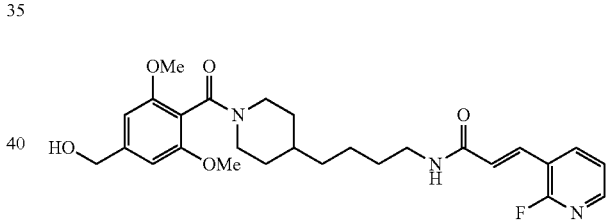

Same procedure as described above starting from 48 and carboxylic acid 50 gave MPM-12 Yield: (189.3 mg, 0.379 mmol, 58%, MW: 499.583) as a white solid. IR (v cm$^{-1}$) 3278 (NH, OH), 2935, 2854, 1603 (C=O), 1417, 11243, 978, 765. $^1$H NMR (300 MHz, CDCl$_3$, δ ppm, J Hz) δ 8.14-8.12 (m, 1H, H-arom.), 7.86-7.80 (m, 1H, H-arom.), 7.54 (d, 1H, $J_{H,H}$=15.8, CH=CH), 7.21-7.17 (m, 1H, H-arom.), 6.62 (d, 1H, CH=CH), 6.51-6.44 (m, 3H, NH, H-arom.), 4.74-4.70 (m, 1H, H-2a or H-6a), 4.61 (s, 2H, CH$_2$OH), 3.74 (s, 3H, OCH$_3$), 3.72 (s, 3H, OCH$_3$), 3.43-3.29 (m, 3H, H-4', H-2a or H-6a), 2.91-2.83 (m, 1H, H-2b or H-6b), 2.74-2.65 (m, 1H, H-2b or H-6b), 1.75-0.98 (m, 11H, H-3, H-5, H-4, H-1', H-2', H-3'). $^{13}$C-NMR (75.4 MHz, CDCl$_3$, δ ppm) δ 165.5 (C=O), 165.4 (C=O), 161.3 (d, $J_{C-F}$=249.0, C—F), 156.6 (C-arom.), 156.5 (C-arom.), 147.6 (d, $J_{C-F}$=15.2, C-arom.), 144.5 (C-arom.), 140.3 (d, $J_{C-F}$=4.0, C-arom.), 132.1 (d, $J_{C-F}$=4.0, CH=CH), 126.3 (d, $J_{C-F}$=7.4, CH=CH), 122.0 (d, $J_{C-F}$=4.3, C-arom.), 118.4 (d, $J_{C-F}$=26.4, C-arom.), 113.5 (C-arom.), 102.0 (C-arom.), 64.9 (CH$_2$OH), 55.9 (OCH$_3$), 55.8 (OCH$_3$), 47.1 (C-2 or C-6), 41.9 (C-2 or C-6), 39.9 (C-4'), 36.2, 32.9, 32.0, 29.8, 24.1 (C-3, C-4, C-5, C-1', C-2', C-3'). HRESIMS m/z found 522.2369, calc. for C$_{27}$H$_{34}$O$_5$N$_3$FNa: 522.2375.

(E)-3-(2-fluoropyridin-3-yl)-N-(4-(1-(4-formyl-2-methyl-1-propyl-1H-pyrrole-3-carbonyl)piperidin-4-yl)butyl)acrylamide (MPM-14)

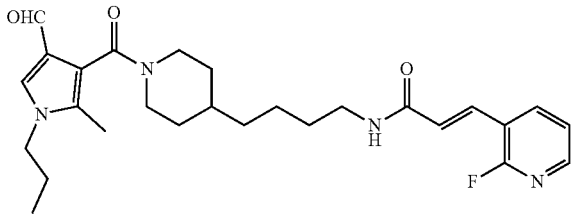 [SMILES: CCCn1cc(C=O)c(C(=O)N2CCC(CCCCNC(=O)/C=C/c3cccnc3F)CC2)c1C]

Same procedure as described above starting from 48 and carboxylic acid 55 gave MPM-14. Yield: (239.9 mg, 0.497 mmol, 76%, MW: 482.600) as a white solid. IR (v cm$^{-1}$) 3283 (NH), 1674 (C=O), 1662, 1599 (C=O). $^1$H NMR (300 MHz, CDCl$_3$, δ ppm, J Hz, mixture of rotamers) δ 9.67, 9.61 (2s, 1H, CHO), 8.15-8.13 (m, 1H, H-arom.), 7.90-7.84 (m, 1H, H-arom.), 7.57, 7.56 (2d, 1H, J$_{H,H}$=15.8, CH=CH), 7.23-7.17 (m, 2H, H-arom.), 6.64, 6.63 (2d, 1H, CH=CH), 6.35, 6.28 (2brt, 1H, J$_{NH,4'}$=5.6, NH), 4.70 (brs, 1H, H-2a or H-6a), 3.76 (t, 1H, J$_{1'',2''}$=6.7, H-1"), 3.61 (brs, 1H, H-2a or H-6a), 3.35 (q, J$_{H,H}$=6.8, H-4'), 2.98-2.74, (brs, 2H, H-2b, H-6b), 2.20, 2.14 (2s, 3H, CH$_3$), 1.85-1.24 (m, 13H, H-3, H-5, H-4, H-1', H-2', H-3', H-2"), 0.95 (t, 3H, H-3"). $^{13}$C-NMR (75.4 MHz, CDCl$_3$, δ ppm, mixture of rotamers) δ 184.4, 184.2 (CHO), 165.8 (C=O), 165.3 (C=O), 161.3 (d, J$_{C-F}$=244.0, C—F), 147.7 (d, J$_{C-F}$=15.5, C-arom.), 140.4-140.2 (m, C-arom.), 132.4-132.2 (m, CH=CH), 130.3 (C-arom.), 128.2 (C-arom.), 128.6 (C-arom.), 126.3-126.2 (m, C-arom.), 122.7 (C-arom.), 122.0 (d, J$_{C-F}$=4.3, CH=CH), 118.2 (C-arom.), 49.2 (C-1"), 47.3, 42.2 (C-2, C-6), 39.8 (C-4'), 36.1, 35.9, 32.2, 29.9, 29.4, 24.1, 24.0, 24.1 (C-1', C-2', C-3', C-4, C-3, C-5, C-2"), 11.2 (C-3"), 10.4 (CH$_3$). HRESIMS m/z found 505.2576, calc. for C$_{27}$H$_{35}$O$_3$N$_4$FNa: 505.2585.

(E)-3-(2-fluoropyridin-3-yl)-N-(4-(1-(5-formyl-2-methylfuro-3-yl)piperidin-4-yl)butyl) acrylamide (MPM-11)

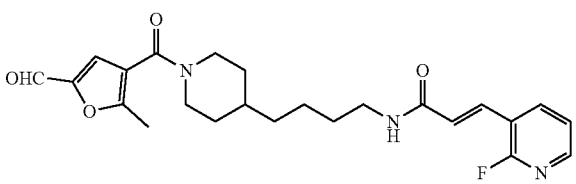 [SMILES: Cc1oc(C=O)cc1C(=O)N1CCC(CCCCNC(=O)/C=C/c2cccnc2F)CC1]

To a solution of compound MPM-10 (0.159 mmol) in CH$_2$Cl$_2$, Dess-Martin reagent (108 mg, 0.254 mmol) is added. The reaction mixture is left to stand at r.t. for 2 h. Then CH$_2$Cl$_2$ (18 mL), saturated aqueous solution (10 mL) of NaHCO$_3$ and Na$_2$S$_2$O$_3$.5H$_2$O (217 mg, 0.875 mmol) is added and the mixture stirred for 5 min is added. Then the phases are separated. The organic phase is washed with saturated aqueous NaHCO$_3$ solution (2×15 mL) and brine (2×15 mL), dried over Na$_2$SO$_4$, filtered and concentrated to dryness.

Purification by column chromatography of the residue on silica gel (CH$_2$Cl$_2$:MeOH, 30:1) gave compound MPM-11. Yield: (64 mg, 0.145 mmol, 91%. MW: 441.503) as a white solid. IR (v cm$^{-1}$) 3286 (NH), 1674 (C=O), 1615 (C=O). $^1$H NMR (300 MHz, CDCl$_3$, δ ppm, J Hz) δ 9.55 (s, 1H, CHO), 8.17-8.15 (m, 1H, H-arom.), 7.89-7.83 (m, 1H, H-arom.), 7.57 (d, 1H, J$_{H,H}$=15.8, CH=CH), 7.24-7.20 (m, 1H, H-arom.), 7.15 (s, 1H, H-arom.), 6.61 (d, 1H, CH=CH), 5.86 (brt, 1H, J$_{NH,4'}$=5.6, NH), 4.54 (brs, 1H, H-2a or H-6a), 3.80 (brs, 1H, H-2a or H-6a), 3.49 (q, J$_{H,H}$=6.8, H-4'), 2.97, (brs, 1H, H-2b or H-6b), 2.70, (brs, 1H, H-2b or H-6b), 2.48 (s, 3H, CH$_3$), 1.78-1.11 (m, 11H, H-3, H-5, H-4, H-1', H-2', H-3'). $^{13}$C-NMR (75.4 MHz, CDCl$_3$, δ ppm) δ 177.3 (CHO), 165.3 (C=O), 163.1 (C=O), 161.3 (d, J$_{C-F}$=253.6, C—F), 159.7 (C-arom.), 150.7 (C-arom.), 147.7 (d, J$_{C-F}$=15.3, C-arom.), 140.6 (d, J$_{C-F}$=4.2, C-arom.), 132.8 (d, J$_{C-F}$=4.6, CH=CH), 126.0 (d, J$_{C-F}$=8.7, CH=CH), 122.0 (d, J$_{C-F}$=4.5, C-arom.), 121.3 (C-arom.), 119.5 (C-arom.), 118.2 (d, J$_{C-F}$=26.3, C-arom.), 47.7, 42.8 (C-2, C-6), 39.9 (C-4'), 36.1, 36.0, 32.0, 30.0, 24.1 (C-1', C-2', C-3', C-4, C-3, C-5), 13.7 (CH$_3$). HRESIMS m/z found 464.1958, calc. for C$_{24}$H$_{28}$O$_4$N$_3$FNa: 464.1956.

(E)-3-(2-fluoropyridin-3-yl)-N-(4-(1-(4-formyl-2,6-dimethoxybenzoyl))piperidin-4-yl)butyl)acrylamide (MPM-13)

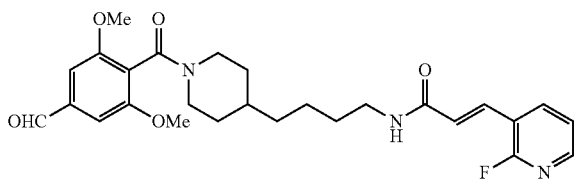 [SMILES: COc1cc(C=O)cc(OC)c1C(=O)N1CCC(CCCCNC(=O)/C=C/c2cccnc2F)CC1]

Same procedure as above but staring from MPM-12 (0.159 mmol) gave MPM-13. Yield: (44.8 mg, 0.09 mmol, 58%, MW: 497.567) as a white solid. IR (v cm$^{-1}$) 3291 (NH), 1617, 1600 (C=O). $^1$H NMR (300 MHz, CDCl$_3$, δ ppm, J Hz) δ 9.93 (s, 1H, CHO), 8.17-8.15 (m, 1H, H-arom.), 7.89-7.82 (m, 1H,H-arom.), 7.57 (d, 1H, J$_{H,H}$=15.8, CH=CH), 7.24-7.19 (m, 1H, H-arom.), 7.08 (s, 1H, H-arom.), 7.07 (s, 1H, H-arom.), 6.60 (d, 1H, CH=CH), 5.89 (brt, 1H, J$_{NH,4'}$=5.6, NH), 4.78-4.74 (m, 1H, H-2a or H-6a), 3.88 (s, 3H, OCH$_3$), 3.86 (s, 3H, OCH$_3$), 3.41-3.34 (m, 3H, H-4', H-2a or H-6a), 2.94 (td, 1H, J$_{H,H}$=12.8, J$_{H,H}$=2.7, H-2b or H-6b), 2.75 (td, 1H, J$_{H,H}$=12.9, J$_{H,H}$=3, H-2b or H-6b), 1.81-1.06 (m, 11H, H-3, H-5, H-4, H-1', H-2', H-3'). $^{13}$C-NMR (75.4 MHz, CDCl$_3$, δ ppm) δ 191.5 (CHO), 165.3 (C=O), 163.9 (C=O), 161.4 (d, J$_{C-F}$=244.0, C—F), 157.3 (C-arom.), 157.2 (C-arom.), 147.8 (d, J$_{C-F}$=15.2, C-arom.), 140.6 (d, J$_{C-F}$=4.2, C-arom.), 138.0 (C-arom.), 132.7 (d, J$_{C-F}$=4.2, CH=CH), 126.1 (d, J$_{C-F}$=8.2, C-arom.), 122.0 (d, J$_{C-F}$=4.4, C-arom.), 121.0 (C-arom.), 118.4 (d, J$_{C-F}$=27, C-arom.), 105.4 (C-arom.), 105.3 (C-arom.), 56.3 (OCH$_3$), 56.2 (OCH$_3$), 47.0 (C-2 or C-6), 41.8 (C-2 or C-6), 39.9 (C-4'), 36.3, 36.2, 32.9, 32.0, 30.0, 24.1 (C-3, C-4, C-5, C-1', C-2', C-3'). HRESIMS m/z found 520.2215, calc. for C$_{27}$H$_{32}$O$_5$N$_3$FNa: 520.2218.

Evaluation of the Anticancer Activity

The compounds according to the present invention were evaluated for their anti-tumor activities on pancreatic ductal adenocarcinoma (Panc-1). To this end, 0.5×10$^6$ human malignant cells were treated with various concentrations (0.001-1000 nM) for 96 hours of FK866 or the compounds according to the present invention. Subsequently cell viability was determined using either sulforhodamine assays as described in Caffa I, et al. (Oncotarget. 2015 May 20; 6(14):11820-32) or MTT assays. Sulforhodamine B is a dye able that binds to cellular proteins. Thus, the amount of this dye, as revealed by dissolving it and by subsequent plate reading with a spectrophotometer, is directly proportional to the number of living cells in each well. For MTT assays, human malignant cells were plated in triplicate on 96-well plates and treated as mentioned above. After 96 hours of incubation, 15 μL of dye solution was added to each well and cells were incubated for an additional 4 hours. Stop solution (100 μL/well) was added for 1 hour and the absorbance was read at 570 nm on a spectrophotometer. To confirm whether the cytotoxicity exerted by these compounds involves programmed cell death, drug-induced cell death was evaluated using annexin V and 7AAD double staining as described by the manufacturer for assessing apoptosis or autophagic-cell death using a Beckman Coulter Cytomics Gallios flow cytometer. Dead cells were identified as annexinV+ and/or 7AAD+. GraphPad Prism version 7.00 (GraphPad Software, San Diego, Calif.) was used for $IC_{50}$ calculation. Table 1 shows $IC_{50}$ of exemplified compounds of the present invention

TABLE 1

| Compound | $IC_{50}$ on Panc-1 (nM) |
|---|---|
| FK866 | 18.4 |
| MPM-07 | 1.5 |
| MPM-08 | 6.0 |
| MPM-09 | 2.0 |
| MPM-13 | 15.5 |
| MPM-14 | 7.54 |
| PER-201 | 14.0 |
| PER-202 | 5.0 |
| FEI-56 | 3.0 |
| FEI-58 | 0.6 |
| FEI-62 | 1.0 |
| FEI-71 | 7.0 |
| FEI-74 | 5.0 |
| FEI-75 | 2.0 |
| FEI-80 | 9.0 |
| FEI-81 | 2.3 |
| FEI-82 | 0.4 |
| FEI-83 | 15.0 |
| FEI-85 | 2.0 |
| FEI-154 | 3.9 |
| FEI-158 | 6.8 |
| FEI-170 | 18.0 |
| FEI-171 | 12.0 |
| FEI-190 | 2.6 |
| FEI-191 | 1.9 |
| FEI-192 | 2.3 |
| FEI-193 | 4.8 |
| FEI-194 | 5.0 |
| FEI-195 | 4.6 |
| FEI-196 | 5.9 |
| FEI-198 | 5.0 |
| FEI-199 | 2.6 |
| FEI-200 | 2.4 |
| FEI-209 | 8.2 |

Pharmacokinetics Parameters

The pharmacokinetics parameters of FK866, FEI199, VAL22-2 and MPM07 were determined following intraperitoneal administration (IP) in female SCID mice.

Material and Methods
SCID (Severe Combined ImmunoDeficiency) mice female total 144
25 mM in DMSO (dimethylsulfoxyde) of each test drug
Saline solution (0.9%)

Test drugs were dissolved in saline solution at 20 mg/ml. All dosing solutions were controlled by HPLC (High-Performance Liquid Chromatography) analysis. Mouse weight is estimated around 20 g.

Dose administration information is presented in Table 2.

TABLE 2

| Number of animals | Group number | Tested drug | Dose level (mg/kg) | Drug route |
|---|---|---|---|---|
| 24 | 1 | FK866 | 20 | IP |
| 24 | 2 | MPM07 | 20 | IP |
| 24 | 4 | VAL22-2 | 20 | IP |
| 24 | 6 | FEI199 | 20 | IP |

Three mice per time point were used in each group.

Blood samples were collected on citrate at 10 min, 30 min, 1 h, 2 h, 4 h, 6 h, 8 h and 24 hours after drug administration. Following centrifugation, resulting plasma was stored at 80° C. pending bioanalysis. Samples were analyzed by LC-MS/MS (Liquid chromatography tandem-mass spectrometry); the lower limit of quantification achieved was between 3 and 12 nM depending on drug. Non compartmental pharmacokinetic analysis was performed on plasma concentration data.

Results

No obvious abnormalities were observed on dosed animals. The pharmacokinetics parameters for each group are summarized in Table 3.

TABLE 3

| | FK866 | MPM07 | FEI-199 | VAL22-2 |
|---|---|---|---|---|
| $C_{max}$ (ng/mL) | 28147 | 13181 | 12108 | 16894 |
| $T_{max}$ (h) | 0.16667 | 0.16667 | 0.16667 | 0.16667 |
| $T_{1/2}\alpha$ (h) | 0.46 | 0.36 | 0.31 | 0.46 |
| $T_{1/2}\beta$ (h) | 3.81 | 25.59 | 10.11 | 8.58 |
| $AUC_{0-inf}$ (ng*h/mL) | 20764 | 5196 | 5228 | 8472 |
| Percentage of extrapolated AUC from $T_{6\,h}$ to infinity | 1.2% | 2.0% | 0.5% | 1.4% |
| $AUC_{0-8\,h}$ (ng*h/mL) | 20654 | 5107 | 5205 | 8405 |
| CL(mL/h) | 9.6 | 38.5 | 38.3 | 23.6 |

AUC: Area under the curve;
t½α (0 -> 6 h);
t½β (6 -> 24 h)

Pharmacokinetic Study—Estimation of the Parameters
Calculations carried out by using time points from 10 min to 24 h and non-compartmental approaches;
Terminal slope estimated with the 3 last concentrations measurements;
$AUC_{0-inf}$ calculated using the log-trapezoidal rule, extrapolated to infinity;
$AUC_{6-inf}$ calculated using the log-trapezoidal rule form time 6 h to infinity;
CL calculated as dose/AUC;
The ratio of $AUC_{6-24\,h}/AUC_{0-inf}$ quantifies the proportion of the AUC in the terminal phase of the concentration time curve relative to $AUC_{0-inf}$; it corresponds to the "Percentage of extrapolated AUC from $T_{6\,h}$ to infinity»

The molecules according to the present invention (FE199, VAL22-2 and MPM07) have improved and longer half-lives in the second phase (long $t_{1/2\beta}$ with low concentrations; 6 h→24 h) than FK866.

The invention claimed is:

1. A compound of Formula I

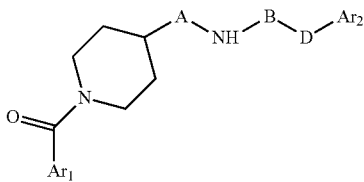

wherein

Ar₁ is aryl or heteroaryl, which are optionally substituted by one, two or three substituents selected from lower alkyl; lower alkoxy; formyl; hydroxyl; lower alkyl substituted by lower alkoxy or hydroxyl;

A is $C_nH_{2n}$, $C_nH_{2n-2}$, $C_nH_{2n-4}$, wherein n=4,5,6,7;

B is C=N—CN;

D is NH;

Ar₂ is aryl or heteroaryl which are optionally substituted by one, two or three halogen substituents or a pharmaceutically acceptable salt, a racemic mixture or its corresponding enantiomers and/or optical isomers.

2. The compound of formula I according to claim 1 wherein Ar₁ is phenyl; thiophen; furan; oxazole; pyrrol; which are optionally substituted by one, two or three substituents selected from lower alkyl; lower alkoxy; formyl; hydroxyl; lower alkyl substituted by one, two or three lower alkoxy or hydroxyl.

3. The compound of formula I according to claim 1, wherein Ar₂ is pyridine; pyridazin; diazin; which are optionally substituted by one, two or three halogen substituents.

4. The compounds of formula I according to claim 1, wherein the halogen substituent is fluorine.

5. The compound according to claim 1, wherein Ar₁ is phenyl; thiophen-2-yl; 2,4-dimethoxyphenyl; 2,6-dimethoxyphenyl; 2,4,6-trimethoxyphenyl; 3-methoxyfuran-2-yl; furan-2-yl; 1,2-oxazole-5-yl; 4-formyl-2,6-dimethoxyphenyl; 4-(dimethoxymethyl)-2,6-dimethoxyphenyl; 5-hydroxy-2-methylfuro-2-yl; 5-formyl-2-methylfuro-3-yl; 4-hydroxymethyl-2,6-dimethoxyphenyl; 4-formyl-2,6-dimethoxyphenyl; 4-formyl-2-methyl-1-propyl-pyrrol-3-yl.

6. The compound of formula I according to claim 1, wherein Ar₁ is 2,4-dimethoxyphenyl; 2,6-dimethoxyphenyl; 2,4,6-trimethoxyphenyl.

7. The compound of formula I according to claim 1, wherein Ar₂ is pyridazi-3-yl; 2-fluoropyridin-3-yl; 4-fluoropyridin-3-yl; 5-fluoropyridin-3-yl; 2,4-difluoropyridin-3-yl; 2,6-difluoropyridin-3-yl; pyridazi-4-yl; 2-fluoropyridin-4-yl; 3-fluoropyridin-4-yl; 6-fluoropyridin-4-yl; 2,3-difluoropyridin-4-yl; 2,5-difluoropyridin-4-yl; 3,5-difluoropyridin-4-yl; 2,4,5-trifluoropyridin-4-yl; pyridazine-5-yl; 1,2-diazin-4-yl.

8. The compound of formula I according to claim 1, wherein Ar₂ is 2-fluoropyridin-4-yl; 3-fluoropyridin-4-yl; 6-fluoropyridin-4-yl; 2,3-difluoropyridin-4-yl; 2,5-difluoropyridin-4-yl; 3,5-difluoropyridin-4-yl; 2,4,5-trifluoropyridin-4-yl.

9. The compound of formula I according to claim 1, wherein A is $C_nH_{2n}$, $C_nH_{2n-2}$ or $C_nH_{2n}$ and n is 4.

10. The compound of formula I according to claim 9 wherein A is $C_4H_8$.

11. The compound of formula I according to claim 1, wherein A is $C_nH_{2n}$, $C_nH_{2n-2}$ or $C_nH_{2n-4}$ and n is 5.

12. The compound of formula I according to claim 11, wherein A is $C_5H_{10}$.

13. The compound of formula I according to claim 1, wherein

A is $C_4H_8$ or $CH_{10}$;

B is C=N—CN;

D is NH;

Ar₁ is 2,4-dimethoxyphenyl; 2,6-dimethoxyphenyl; 2,4,6-trimethoxyphenyl;

Ar₂ is 2-fluoropyridin-4-yl; 3-fluoropyridin-4-yl; 6-fluoropyridin-4-yl; 2,3-difluoropyridin-4-yl; 2,5-difluoropyridin-4-yl; 3,5-difluoropyridin-4-yl; 2,4,5-trifluoropyridin-4-yl.

14. The compound of formula I according to claim 1 which is (E)-1-(4-(1-Benzoylpiperidin-4-yl)butyl)-2-cyano-3-(pyridin-4-yl)guanidine;

(E)-2-Cyano-1-(4-(1-(2,6-dimethoxybenzoyl)piperidin-4-yl)butyl)-3-(pyridin-4-yl)guanidine;

(E)-2-Cyano-1-(4-(1-(furan-2-carbonyl)piperidin-4-yl)butyl)-3-(pyridin-4-yl)guanidine;

(E)-2-Cyano-1-(pyridin-4-yl)-3-(4-(1-(thiophene-2-carbonyl)piperidin-4-yl)butyl)guanidine;

(E)-2-cyano-1-(4-(1-(4-(dimethoxymethyl)-2,6-dimethoxybenzoyl)piperidin-4-yl)butyl)-3-(pyridazin-4-yl)guanidine;

(E)-2-Cyano-1-(4-(1-(furan-2-carbonyl)piperidin-4-yl)butyl)-3-(pyridazin-4-yl)guanidine;

(E)-1-(4-(1-Benzoylpiperidin-4-yl)butyl)-2-cyano-3-(6-fluoropyridin-3-yl)guanidine;

(E)-2-Cyano-1-(4-(1-(2,6-dimethoxybenzoyl)piperidin-4-yl)butyl)-3-(6-fluoropyridin-3-yl)guanidine;

(E)-2-cyano-1-(4-(1-(4-(dimethoxymethyl)-2,6-dimethoxybenzoyl)piperidin-4-yl)butyl)-3-(6-fluoropyridin-3-yl)guanidine;

(E)-2-Cyano-1-(6-fluoropyridin-3-yl)-3-(4-(1-(furan-2-carbonyl)piperidin-4-yl)butyl)guanidine;

(E)-2-Cyano-1-(6-fluoropyridin-3-yl)-3-(4-(1-(thiophene-2-carbonyl)piperidin-4-yl)butyl)guanidine;

(E)-1-(5-(1-Benzoylpiperidin-4-yl)pentyl)-2-cyano-3-(pyridin-3-yl)guanidine;

(E)-2-Cyano-1-(5-(1-(furan-2-carbonyl)piperidin-4-yl)pentyl)-3-(pyridin-3-yl)guanidine;

(E)-2-Cyano-1-(pyridin-3-yl)-3-(5-(1-(thiophene-2-carbonyl)piperidin-4-yl)pentyl)guanidine;

(E)-1-(5-(1-Benzoylpiperidin-4-yl)pentyl)-2-cyano-3-(pyridin-4-yl)guanidine;

(E)-2-Cyano-1-(5-(1-(furan-2-carbonyl)piperidin-4-yl)pentyl)-3-(pyridin-4-yl)guanidine;

(E)-2-Cyano-1-(pyridin-4-yl)-3-(5-(1-(thiophene-2-carbonyl)piperidin-4-yl)pentyl)guanidine;

(E)-2-Cyano-1-(5-(1-(2,6-dimethoxybenzoyl)piperidin-4-yl)pentyl)-3-(pyridin-4-yl)guanidine;

(E)-1-((E)-5-(1-Benzoylpiperidin-4-yl)pent-2-en-1-yl)-2-cyano-3-(pyridin-3-yl)guanidine;

(E)-2-Cyano-1-((E)-5-(1-(furan-2-carbonyl)piperidin-4-yl)pent-2-en-1-yl)-3-(pyridin-3-yl)guanidine;

(E)-2-Cyano-1-(pyridin-3-yl)-3-((E)-5-(1-(thiophene-2-carbonyl)piperidin-4-yl)pent-2-en-1-yl)guanidine;

(E)-2-Cyano-1-((E)-5-(1-(2,6-dimethoxybenzoyl)piperidin-4-yl)pent-2-en-1-yl)-3-(pyridin-3-yl)guanidine;

(E)-1-((E)-5-(1-Benzoylpiperidin-4-yl)pent-2-en-1-yl)-2-cyano-3-(pyridin-4-yl)guanidine;
(E)-2-Cyano-1-((E)-5-(1-(furan-2-carbonyl)piperidin-4-yl)pent-2-en-1-yl)-3-(pyridin-4-yl)guanidine;
(E)-2-Cyano-1-(pyridin-4-yl)-3-((E)-5-(1-(thiophene-2-carbonyl)piperidin-4-yl)pent-2-en-1-yl)guanidine;
(E)-2-Cyano-1-((E)-5-(1-(2,6-dimethoxybenzoyl)piperidin-4-yl)pent-2-en-1-yl)-3-(pyridin-4-yl)guanidine.

15. A therapeutically active substance comprising a compound of formula I according to claim 1.

16. A method for treating pancreatic cancer, the method comprising administering a medicament comprising a compound of formula I according to claim 1 to a subject in need of such treatment.

17. A pharmaceutical composition comprising a compound of formula I as claimed in claim 1 and pharmaceutically acceptable excipients.

18. A process for the manufacture of a compound of formula I according to claim 1, which process comprises:
reacting a compound of formula 3

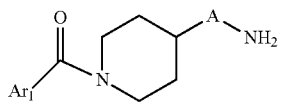

with a compound of formula 4

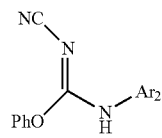

to produce a compound of formula I

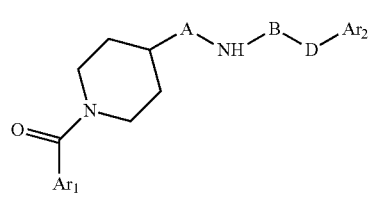

(I)

wherein
A is $C_nH_{2n}$, $C_nH_{2n-2}$, $C_nH_{2n-4}$ wherein n=4,5,6,7;
B is C=N—CN;
D is NH;
$Ar_1$ and $Ar_2$ are as defined in claim 1.

* * * * *